US012193832B2

(12) United States Patent
Ogawa et al.

(10) Patent No.: US 12,193,832 B2
(45) Date of Patent: Jan. 14, 2025

(54) GAME PROGRAM, METHOD, AND INFORMATION PROCESSING DEVICE

(71) Applicant: The Pokemon Company, Tokyo (JP)

(72) Inventors: Satoshi Ogawa, Tokyo (JP); Takuya Hashimoto, Tokyo (JP); Satoki Nakamura, Tokyo (JP)

(73) Assignee: THE POKEMON COMPANY, Tokyo (JP)

( * ) Notice: Subject to any disclaimer, the term of this patent is extended or adjusted under 35 U.S.C. 154(b) by 446 days.

(21) Appl. No.: 17/696,866

(22) Filed: Mar. 17, 2022

(65) Prior Publication Data

US 2022/0202357 A1 Jun. 30, 2022

Related U.S. Application Data

(63) Continuation of application No. PCT/JP2020/035572, filed on Sep. 18, 2020.

(30) Foreign Application Priority Data

Sep. 20, 2019 (JP) .................................. 2019-171960

(51) Int. Cl.
*A61B 5/00* (2006.01)
*A63F 13/212* (2014.01)
(Continued)

(52) U.S. Cl.
CPC .......... *A61B 5/4809* (2013.01); *A61B 5/4815* (2013.01); *A63F 13/212* (2014.09); *A63F 13/45* (2014.09); *A63F 13/5375* (2014.09)

(58) Field of Classification Search
None
See application file for complete search history.

(56) References Cited

U.S. PATENT DOCUMENTS

| 2014/0058703 A1* | 2/2014 | Kimishima | .......... G06Q 10/109 |
| | | | 702/177 |
| 2016/0213309 A1* | 7/2016 | Sannholm | ............ A61B 5/7271 |

(Continued)

FOREIGN PATENT DOCUMENTS

| JP | 3048489 U | 5/1998 |
| JP | 2012-81063 A | 4/2012 |

(Continued)

OTHER PUBLICATIONS

Written Opinion of the International Searching Authority mailed on Nov. 10, 2020, received for PCT Application PCT/JP2020/035572, Filed on Sep. 18, 2020, 4 pages. (Previously filed; submitting English translation only.).

(Continued)

*Primary Examiner* — Jason T Yen
(74) *Attorney, Agent, or Firm* — XSENSUS LLP

(57) ABSTRACT

A game system encouraging a user to have an appropriate sleep habit is provided. For example, a game program causes a processor to execute: a first step of accepting designation of a first time frame that is a target for taking sleep from a user; a second step of setting a second time frame not coinciding with the first time frame in relation with the designated first time frame; a third step of acquiring first information about sleep taken by the user; and a fourth step of performing game control on the basis of the first information, in which, in the fourth step, the game control is performed in accordance with whether or not sleep is taken in the second time frame regardless of whether a result of sleep of the user is appropriate for the first time frame on the basis of the first information.

16 Claims, 23 Drawing Sheets

(51) Int. Cl.
   *A63F 13/45*     (2014.01)
   *A63F 13/5375*   (2014.01)

(56) References Cited

U.S. PATENT DOCUMENTS

| | | | |
|---|---|---|---|
| 2017/0136361 | A1 | 5/2017 | Hamaguchi et al. |
| 2018/0028111 | A1* | 2/2018 | Waris ................. A61B 5/165 |
| 2019/0381396 | A1* | 12/2019 | Nishimura ........... A63F 13/212 |
| 2020/0038621 | A1* | 2/2020 | Vukovic ............... G04G 21/06 |
| 2021/0031000 | A1* | 2/2021 | Lee ..................... A61B 5/6892 |

FOREIGN PATENT DOCUMENTS

| | | | |
|---|---|---|---|
| JP | 2016-49237 | A | 4/2016 |
| JP | 2017-158005 | A | 9/2017 |
| JP | 2019-58418 | A | 4/2019 |
| JP | 2019-79100 | A | 5/2019 |
| JP | 2019-111181 | A | 7/2019 |

OTHER PUBLICATIONS

Office Action issued Mar. 13, 2023 in Japanese Patent Application No. 2023-007260, 8 pages.
Japan's First "Sleep Reward System"—Company Rewards for Sleeping 6 Hours or More, AMP News, Oct. 9, 2018, URL:<https://ampmedia.jp/2018/10/09/sleep-system/> [Date of search: Feb. 27, 2023] (Copy Not Submitted—See English Translation of Japanese Office Action dated Mar. 13, 2023 for Statement of Relevancy.).
International Search Report and Written Opinion mailed on Nov. 10, 2020, received for PCT Application PCT/JP2020/035572, Filed on Sep. 18, 2020, 9 pages including English Translation.

\* cited by examiner

Fig. 4

STORAGE UNIT (202)

USER INFORMATION DATABASE (281)

| USER ID | USER NAME | USER LEVEL | STAMINA CURRENT VALUE | STAMINA MAXIMUM VALUE | OWNED GAME OBJECT | USER ATTRIBUTE SETTING | RESTRICTION ACCORDING TO SLEEP EVALUATION |
|---|---|---|---|---|---|---|---|
| #11AA22BB | ASX123 | 66 | 11 | 120 | ... | FAMILY "FFF" | SPECIFIC GAME ACTION "MM" IS PERMITTED, EVENT PARTICIPATION PERIOD SETTING "2", ... |
| #6D7E8F99 | KKLLMM | 22 | 70 | 80 | ... | ... | ... |
| ... | ... | ... | ... | ... | ... | ... | ... |

FRIEND LIST (282)

| USER 1 | USER 2 | FRIEND REGISTRATION DATE | DISCLOSURE/NON-DISCLOSURE OF SLEEP INFORMATION | COMMON ATTRIBUTE | COMMON SLEEP TIME |
|---|---|---|---|---|---|
| #11AA22BB | #6D7E8F99 | JULY 7, 2019 | MUTUAL DISCLOSURE | FAMILY | 23:30 - 06:00 |
| #6D7E8F99 | #RRTT5566 | AUGUST 8, 2019 | NON-DISCLOSURE | NONE | 00:30 - 05:00 |
| ... | ... | ... | ... | ... | ... |

SLEEP RESULT INFORMATION (283)

| USER ID | DATE AND TIME | SLEEP OBJECT | SLEEP RESULT | EVALUATION PARAMETER OF SLEEP | SLEEP MEASURING DEVICE | QUALITY OF MEASUREMENT | SLEEP LOCATION |
|---|---|---|---|---|---|---|---|
| #11AA22BB | SEP. 9, 2019 | GOING-TO-BED "23:00", GETTING-UP "06:00" | GOING-TO-BED "23:00", GETTING-UP "06:00" | 95 | #22EDC5B3 | GOOD | PREFECTURE A CITY B |
| #11AA22BB | SEP. 9, 2019 | GOING-TO-BED "23:00", GETTING-UP "06:00" | GOING-TO-BED "23:05", GETTING-UP "05:55" | 75 | #33E41AC3 | BAD | ... |
| ... | ... | ... | ... | ... | ... | ... | ... |

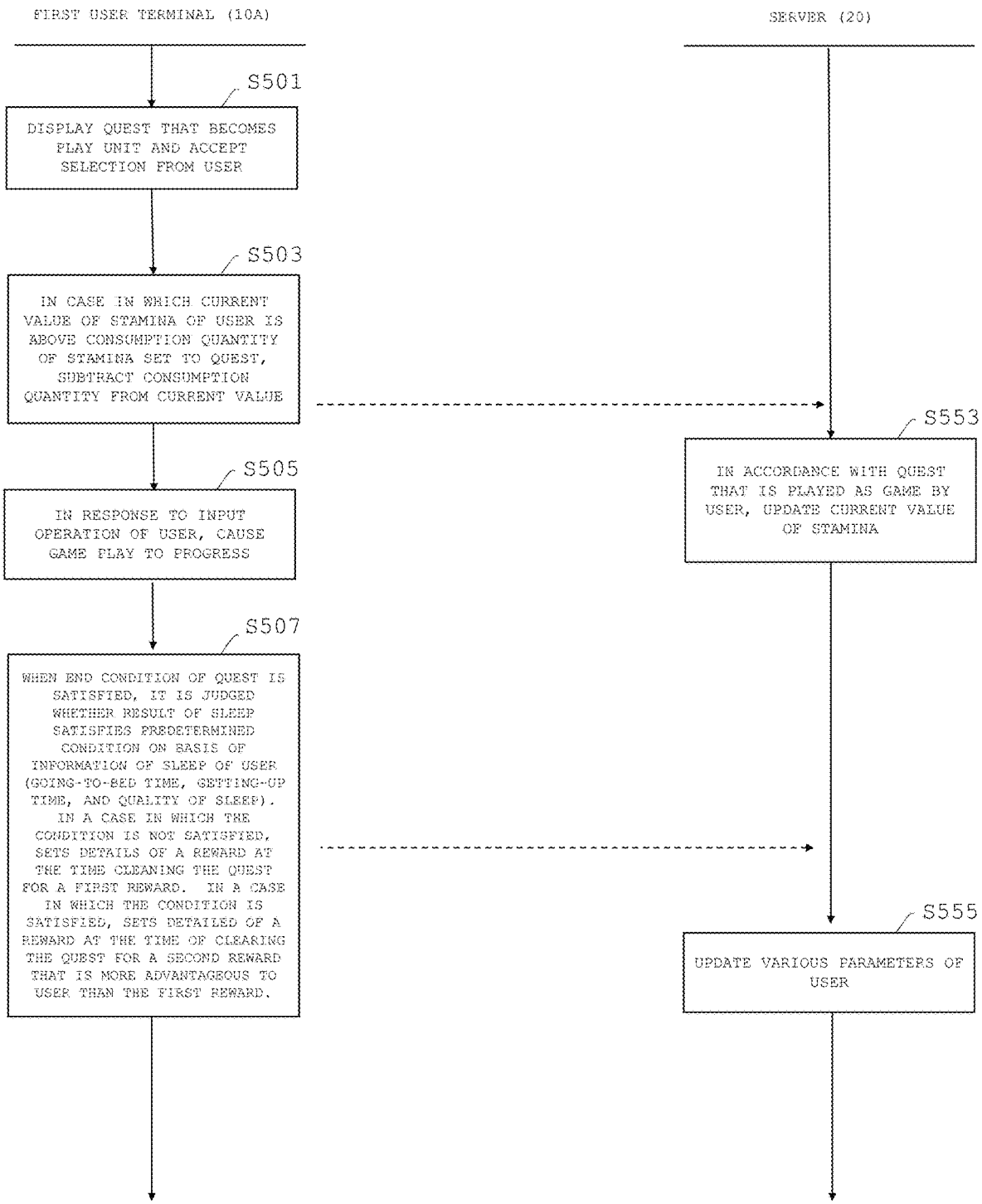

Fig. 16

| | | 202 |
|---|---|---|
| STORAGE UNIT | | |

| SLEEP MEASURING DEVICE SETTING 284 | | | | |
|---|---|---|---|---|
| SLEEP MEASURING DEVICE ID | DEVICE NAME | DEVICE PROVISION PERIOD | SENSING SPECIFICATION | EFFECT AT TIME OF GAME PLAY |
| #3C4D5F6F | S_Device01 | SALE ON OCT. 10, 2019 | QUALITY OF SLEEP, SLEEP TIME, ACCURACY A, BIOLOGICAL INFORMATION, ... | • APPLY SETTING "G" OF PROBABILITY FOR OBTAINMENT OF GAME OBJECT ... |
| #22EDC5B3 | S_Watch_02 | SALE ON APR. 2, 2019 (ON SALE NOW) | QUALITY OF SLEEP, SLEEP TIME, ACCURACY B, ... | GRANT PRIVILEGE "B" AT TIME OF STARTING GAME |
| ... | ... | ... | ... | ... |

Fig. 21

| | | | | SLEEP RESULT INFORMATION | | | | 6283 |
|---|---|---|---|---|---|---|---|---|
| USER ID | DATE AND TIME | SLEEP OBJECT | CORE TIME | SLEEP RESULT | EVALUATION PARAMETER OF SLEEP | SLEEP MEASURING DEVICE | QUALITY OF MEASUREMENT | SLEEP LOCATION |
| #11AA22BB | SEP. 7, 2019 | GOING-TO-BED "23:00", GETTING-UP "06:00" | 01:00-05:00 | GOING-TO-BED "22:50", GETTING-UP "05:50" | 90 | #22EDC5B3 | GOOD | A PREFECTURE B CITY |
| #11AA22BB | SEP. 9, 2019 | GOING-TO-BED "23:00", GETTING-UP "06:00" | 01:00-05:00 | GOING-TO-BED "24:00", GETTING-UP "05:50" | 90 | #22EDC5B3 | GOOD | ... |
| #6D7E8F99 | MAY 3, 2019 | GOING-TO-BED "24:00", GETTING-UP "06:00" | 01:30-05:00 | GOING-TO-BED "02:00", GETTING-UP "07:00" | 65 | #33E41AC3 | BAD | ... |
| ... | ... | ... | ... | ... | ... | ... | ... | ... |

GAME PROGRAM, METHOD, AND INFORMATION PROCESSING DEVICE

CROSS-REFERENCE TO RELATED APPLICATIONS

This is a Bypass Continuation of National Stage Application based on PCT/JP2020/035572, filed Sep. 18, 2020, which claims priority to JP 2019-171960, filed Sep. 20, 2019, the entire contents of each are incorporated herein by its reference.

TECHNICAL FIELD

The present disclosure relates to a game program, a method, and an information processing device.

BACKGROUND

Technologies for measuring sleep are known. For example, by allowing a user to wear a wrist-watch type device, a stage of the user's sleep that is one of light sleep, deep sleep, and REM sleep is identified in accordance with an output result of a motion sensor mounted in the device. In accordance with this, changes in each stage of sleep over time can be recorded.

In such a device used for measuring sleep, a reminder for notifying a user that a sleeping time is approaching may be set. This is on the basis of research results indicating that the quality of sleep is improved by maintaining a constant bedtime and getting-up time.

Reflecting data measured during a user's sleep in a game program is also performed. In Japanese Patent Application Publication No. 2012-81063 (PTL 1), it is described that the quality of sleep of a player is reflected in a game on the basis of pulse wave information during sleep.

[PTL 1] Japanese Patent Application Publication No. 2012-81063

SUMMARY

Technical Problems

However, even when a user tries to foam a regular sleep habit, lifestyle habits of the user may vary from day to day. For example, a time frame in which a user can sleep may vary in accordance with work of the user and the user's degree of pleasure.

In a case in which a game according to a user's sleep state is provided, the user continuously executes the game every day. For this reason, in a case in which a user's lifestyle habits vary, it becomes difficult for the user to continuously maintain a regular sleep habit, and there may be a psychological burden. As a result, there is concern that enjoyment of a game according to a sleep state may not be sufficiently exhibited.

Solutions to Problems

For this reason, a technology for further improving enjoyment of a game according to a sleep state even in a case in which there is a variation in a user's lifestyle habits has become necessary. Thus, an object of the present disclosure is to provide a game system that encourages a user to have an appropriate user's sleep habit.

According to one embodiment, a game program for being executed by a computer including a processor and a memory is provided. The game program causes the processor to execute: a first step of accepting designation of a first time frame from a user; a second step of setting a second time frame not coinciding with the first time frame in relation with the designated first time frame; a third step of acquiring first information about sleep taken by the user; and a fourth step of performing game control on the basis of the first information, in which, in the fourth step, the game control is performed in accordance with whether or not sleep is taken in the second time frame regardless of whether a result of sleep of the user is appropriate for the first time frame on the basis of the first information.

According to one embodiment, a method executed by a computer including: a processor; and a memory is provided. The method includes, by causing the processor to read and execute a game program stored in the memory: a first step of accepting designation of a first time frame that is a target for taking sleep from a user; a second step of setting a second time frame not coinciding with the first time frame in relation with the designated first time frame; a third step of acquiring first information about sleep taken by the user; and a fourth step of performing game control on the basis of the first information, in which, in the fourth step, the game control is performed in accordance with whether or not sleep is taken in the second time frame regardless of whether a result of sleep of the user is appropriate for the first time frame on the basis of the first information.

According to one embodiment, an information processing device including: a control unit; and a storage unit is provided. The control unit, by operating on the basis of a game program stored in the storage unit, executes: a first step of accepting designation of a first time frame that is a target for taking sleep from a user; a second step of setting a second time frame not coinciding with the first time frame in relation with the designated first time frame; a third step of acquiring first information about sleep taken by the user; and a fourth step of performing game control on the basis of the first information, in which, in the fourth step, the game control is performed in accordance with whether or not sleep is taken in the second time frame regardless of whether a result of sleep of the user is appropriate for the first time frame on the basis of the first information.

According to the present disclosure, enjoyment of a game according to a sleep state can be further improved while encouraging a user to have an appropriate user's sleep habit in accordance with a user's lifestyle habit.

BRIEF DESCRIPTION OF DRAWINGS

FIG. 4 is a diagram illustrating a data structure of a user information database 281, a friend list 282, and a sleep result information 283 stored by the server 20.

FIG. 5 is a flowchart illustrating a process in which a user performs game play by consuming a consumption quantity set in a game unit from a current value of a stamina value by designating the game unit, and a reward at the time of clearing the game unit is set as details according to a result of sleep of the user.

FIG. 14 is a flowchart illustrating a process of granting a privilege to a user in accordance with the user taking sleep at a specific location such as an accommodation facility or the like.

FIG. 15 is a block diagram illustrating a configuration of a sleep measuring device 11B and the like.

FIG. 16 is a diagram illustrating a data structure of a sleep measuring device setting 284 stored by the server 20.

FIG. 21 is a diagram illustrating a data structure of sleep result information 6283 according to Embodiment 6.

DETAILED DESCRIPTION

Hereinafter, embodiments of the present disclosure will be described with reference to the drawings. In description presented below, the same reference signs are assigned to the same components. Names and functions thereof are the same as well. Thus, detailed description thereof will not be repeated.

First Embodiment

<1 Configuration Diagram of Entire Game System>

Figure 1:
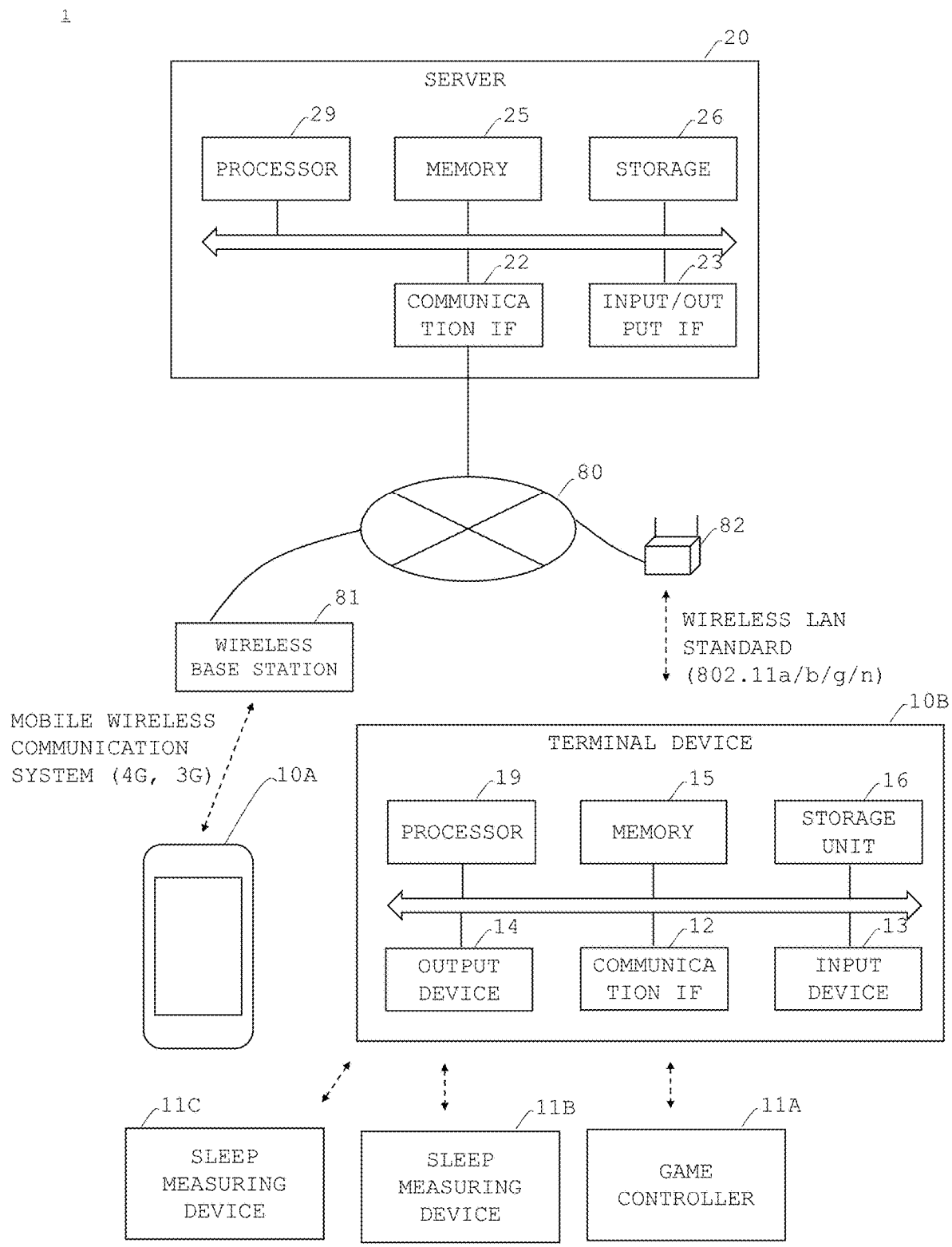
FIG. 1 is a diagram illustrating the entire configuration of a game system 1.

FIG. 1 is a diagram illustrating the entire configuration of a game system 1.

As illustrated in FIG. 1, the game system 1 includes a plurality of terminal devices (a terminal device 10A and a terminal device 10B are illustrated in FIG. 1; hereinafter they may be collectively referred to as a "terminal device 10") and a server 20. The terminal device 10 and the server 20 are communicatively connected through a network 80.

The terminal device 10 is a device that is operated by each user. The terminal device 10 is realized by a portable terminal such as a smartphone, a tablet, or the like corresponding to a mobile communication system. Other than that, the terminal device 10, for example, may be a stationary-type personal computer (PC), a laptop PC, or a game machine. In addition, the terminal device 10 may be configured to function as a head mounted display and, for example, may be configured to function as a head mounted display of a transmissive type, a non-transmissive type, or a see-through type. For example, the terminal device 10 may be configured to function as a portable terminal in the case of not functioning as a head mounted display and function as a head mounted display by being mounted in a goggle-type device. In such a case, the terminal device 10 can perform switching between a mode in which the terminal device functions as a portable terminal and a mode in which the terminal device functions as a head mounted display. In the case of the mode in which the terminal device functions as a head mounted display, the terminal device 10 detects a motion of a user's head part using a motion sensor built in the terminal device 10 and updates a displayed image of the display in accordance with a motion of the user's head part.

As represented as a terminal device 10B in FIG. 1, the terminal device 10 includes a communication interface (IF) 12, an input device 13, an output device 14, a memory 15, a storage unit 16, and a processor 19. The server 20 includes a communication IF 22, an input/output IF 23, a memory 25, a storage 26, and a processor 29.

The terminal device 10 is communicatively connected to the server 20 through the network 80. The terminal device 10 is connected to the network 80 by communicating with a communication device such as a radio base station device 81 compliant with a communication standard such as 5G, Long Term Evolution (LTE), or the like, a wireless LAN router 82 compliant with a wireless local area network (LAN) standard such as Institute of Electrical and Electronics Engineers (IEEE) 802.11 or the like.

The communication IF 12 is an interface for inputting/outputting signals for enabling the terminal device 10 to communicate with external devices. The input device 13 is an input device (for example, a pointing device such as a touch panel, a touch pad, a mouse, or the like, a keyboard, and the like) for accepting an input operation from a user. The output device 14 is an output device (a display, a speaker, or the like) used for presenting information to a user. The memory 15 is for temporarily storing a program, data processed by a program or the like, and the like and, for example, is a volatile memory such as a dynamic random access memory (DRAM). The storage unit 16 is a storage device for storing data and, for example, is a flash memory or a hard disc drive (HDD). The processor 19 is hardware used for executing a command set described in a program and is configured using an arithmetic operation device, a register, a peripheral circuit, and the like.

As illustrated in the drawing, the terminal device 10 is connected to a game controller 11A in a wired manner or a wireless manner. A user can play a game by operating the game controller 11A. The terminal device 10 may be configured to be able to communicate with a plurality of game controllers 11A. For example, a plurality of users can play a game using one terminal device 10. In addition, the game controller 11 may have a structure of being able to be detachably attached to the terminal device 10. The game controller 11 may be one device that can be gripped by both hands of a user or may be configured using two devices respectively gripped by both hands of a user. For example, the game controller 11 may include a gyro sensor, an infrared sensor, or the like and detect a motion of a body (for example, a motion of a hand) of a user in a case in which the user grips the game controller 11.

In addition, as illustrated in the drawing, the terminal device 10 is connected to one or a plurality of sleep measuring devices in a wired manner or a wireless manner. Sleep measuring devices 11B and 11C are devices used for acquiring information about sleep of a user of the terminal device 10. FIG. 1 illustrates two sleep measuring devices including the sleep measuring device 11B and the sleep measuring device 11C. Hereinafter, a plurality of sleep measuring devices may be collectively referred to as "the sleep measuring device 11B and the like." The sleep measuring devices 11B and 11C, for example, are wearable devices of a wrist watch type, a ring type, an eye-mask type, or the like worn on a body of a user and include motion sensors such as gyro sensors or the like. In addition, the sleep measuring devices 11B and 11C may be devices that are placed in a mattress on which a user is sleeping, a headboard, or the like. Furthermore, the terminal device 10 and the sleep measuring device 11B or the sleep measuring device 11C may be the same device. In other words, the terminal device 10 may be configured to function also as a sleep measuring device.

In addition, there are cases in which a user uses two or more sleep measuring devices at the same time. For example, a user may wear two sleep measuring devices of a wrist watch type or may use a smartphone as a sleep measuring device while wearing a sleep measuring device of a wrist watch type. In accordance with this, a motion of a body of a user during sleep can be detected using a gyro sensor or the like. By accumulating sensing results (sensing data 182B) that have been sensed using various sensors during sleep of a user, it can be identified whether the user is during sleep, in a light sleep state, a deep sleep state, a REM sleep, a non-REM sleep, or the like. In this way, by identifying the waveform of a REM sleep or a non-REM sleep and the like, the quality of sleep of a user can be evaluated. For example, cycles of a REM sleep and a non-REM sleep in the case of a sleep of a good quality are set in advance, and the quality of a sleep of a user can be evaluated by comparing the waveform thereof with the waveforms of the REM sleep and the non-RM sleep at the time of the user sleeping.

In addition, the terminal device 10 detects that a user has gotten into bed (for example, has lied down horizontally on a bed) and has fell asleep after getting into bed on the basis of an output of a motion sensor of the sleep measuring device 11B and the like. Furthermore, the terminal device 10 can judge whether a user had performed an input operation on the terminal device 10, whether a user had viewed information displayed on the display 132 of the terminal device 10, and the like before the user fell asleep after getting into bed. In other words, it can be judged whether or not a user going to go to bed has operated the terminal device 10 before falling asleep.

In addition, sleep measuring devices assumed to be used in the game system 1 in advance are managed in the foam of a so-called white list. Furthermore, in a case in which reception of data has been detected from the sleep measuring device 11B that is not managed by the game system 1, sleep information may be configured not to be received from the sleep measuring device 11B from which the server 20 cannot be identified, or a subsequent process may be performed using parameters used for the sleep measuring device 11B that cannot be identified or the like.

Differences in types of sleep measuring devices do not necessarily need to be difference in devices. In other words, even sleep measuring devices of the same device configuration may be managed as different sleep measuring devices in the game system 1 in accordance with types of software or applications used until transmission of sleep information to the server 20. For example, even in a case in which sleep information is detected using the same sleep measuring device 11B, in a case in which a sleep measuring application A is used for processing sleep information and a case in which a sleep measuring application B different from the sleep measuring application A is used for processing sleep information, the sleep measuring device can be managed as different "sleep measuring device IDs." In this way, by managing the sleep measuring device as different "sleep measuring device IDs" in accordance with a combination of a type of device as a device configuration and a used application, sleep information can be generated more flexibly, and as a result, enjoyment of a game according to a sleep state can be sufficiently exhibited.

The server 20 manages information of each user. The server 20 manages game characters, game items, a holding amount of virtual currency (including virtual currency given to a user for free and virtual currency given to a user for a fee) owned by each user, a current value and a maximum value (an upper limit value) of a parameter (also referred to as a "stamina value") of an action quantity consumed for each user to play a game unit (also referred to as a quest), information of other users registered as friends by each user, and the like as information of users.

In addition, the server 20 collects sensing results sensed by the sleep measuring device 11B and sleep information of each user generated from the sensing results and accumulates the sensing results and the information that have been collected in a database. For example, the terminal device 10 acquires sensing results of the sleep measuring device 11B and transmits the acquired sensing results to the server 20.

More specifically, as a process for encouraging interchange among users, the server 20 performs user matching and the like for supporting multi-play for playing a game among a plurality of users. In addition, the server 20 performs transmission/reception of messages among users and the like.

The server 20 manages a current value and a maximum value of a stamina value of each user and recovers the current value to the maximum value in accordance with elapse of a time. For example, the server 20 increases the current value of the stamina value for every predetermined time such as every three minutes. The server 20 sets a timer of a predetermined time in response to a decrease of the stamina value from the maximum value of the stamina value according to a user starting game play in a game unit. The server 20 detects elapse of a predetermined time using the timer and increases the stamina value by a predetermined quantity. The server 20 sets the timer again in a case in which the current value has not reached the upper limit of the stamina value as a result of recovery of the stamina value.

In addition, when there is also a case in which the quantity of the action parameter consumed in a game play in a game unit has the same value also for any game unit (the stamina consumption quantity is fixed), the quantity of the action parameter consumed at the time of the game play may be set for each game unit.

The communication IF 22 is an interface for inputting/outputting signals for the server 20 to communicate with an external device. The input/output IF 23 functions as an interface between an input device for accepting an input operation from a user and an output device for presenting information to a user. The memory 25 is used for temporarily storing programs, data processed by the programs, and the like and, for example, is a volatile memory such as a dynamic random access memory (DRAM). The storage 26 is a storage device used for storing data and, for example, is a flash memory, a hard disc drive (HDD), or the like. The processor 29 is hardware used for executing a command set described in a program and is composed of an arithmetic operation device, a register, a peripheral circuit, and the like.

In addition, in the illustrated example, although the terminal devices 10 are configured to communicate with each other through the server 20, a plurality of terminal devices 10 may directly communicate with each other using short-range radio communication not through the server 20. For example, a battle play or the like may be configured to be able to be performed through local communication not through the Internet using two terminal devices 10. In addition, in this embodiment, each device (the terminal device, the server, the sleep measuring device, or the like) may be perceived as an information processing device. In other words, an aggregation of such devices can be perceived as one "information processing device," and the game system 1 may be foamed as an aggregation of a plurality of devices. A method for distributing a plurality of functions required for realizing the game system 1 according to this embodiment to one or a plurality of pieces of hardware can be appropriately determined in consideration of the processing capability of each piece of hardware and/or specifications required for the game system 1, and the like.

For example, the game system may be configured using terminal devices and sleep measuring devices not through the server. In addition, the sleep measuring device and the terminal device may communicate with each other, and, by the terminal device and the server communicating with each other, each of the devices may configure the game system by performing respective processes. Furthermore, the game system may be configured using the sleep measuring device without using the terminal device and the server. In addition, the game system may be configured by the sleep measuring device communicating with the server.

<1.1 Configuration of Terminal Device 10>

Figure 2:
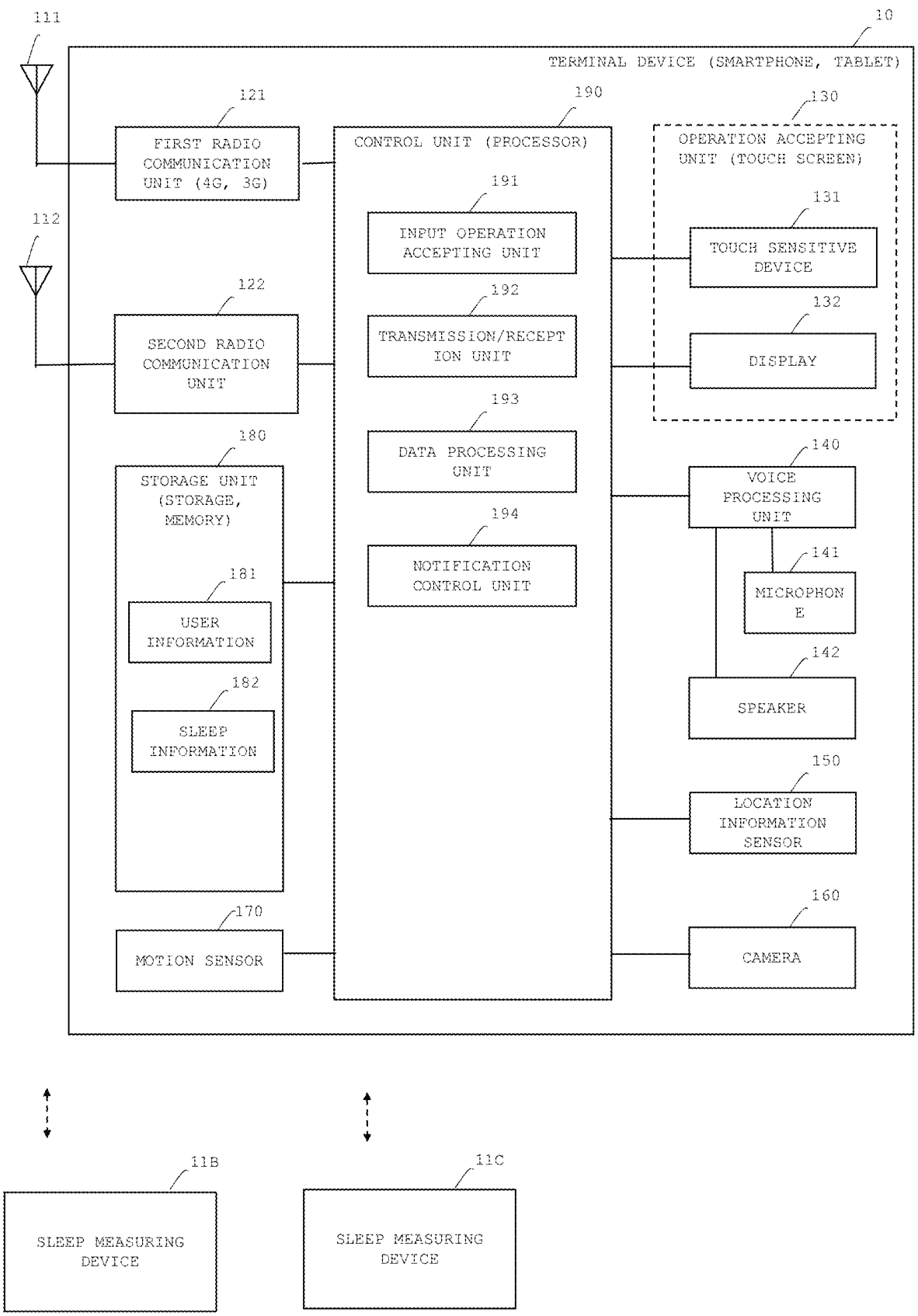
FIG. 2 is a block diagram of a terminal device 10 composing a game system 1 according to Embodiment 1.

FIG. 2 is a block diagram of the terminal device 10 configuring the game system 1 according to Embodiment 1. As illustrated in FIG. 2, the terminal device 10 includes a plurality of antennas (an antenna 111 and an antenna 112), radio communication units respectively corresponding to the antennas (a first radio communication unit 121 and a second radio communication unit 122), an operation accepting unit 130 (including a touch sensitive device 131 and a display 132), a voice processing unit 140, a microphone 141, a speaker 142, a location information sensor 150, a camera 160, a motion sensor 170, a storage unit 180, and a control unit 190. The terminal device 10 also have functions and configurations not particularly illustrated in FIG. 2 (for example, a battery for storing and maintaining electric power, a power supply circuit controlling supply of electric power from the battery to each circuit, and the like). As illustrated in FIG. 2, the blocks included in the terminal device 10 are electrically connected through a bus or the like.

The antenna 111 radiates a signal emitted by the terminal device 10 as an electric wave. In addition, the antenna 111 receives electric waves from the space and gives the received signal to the first radio communication unit 121.

The antenna 112 radiates a signal emitted by the terminal device 10 as an electric wave. In addition, the antenna 112 receives electric waves from the space and gives the received signal to the second radio communication unit 122.

The first radio communication unit 121 performs a modulation/demodulation process and the like for transmitting/receiving signals through the antenna 111 for enabling the terminal device 10 to communicate with other wireless devices. The second radio communication unit 122 performs a modulation/demodulation process and the like for transmitting/receiving signals through the antenna 112 for enabling the terminal device 10 to communicate with other wireless devices. Each of the first radio communication unit 121 and the second radio communication unit 122 is a communication module including a tuner, a received signal strength indicator (RSSI) calculating circuit, a cyclic redundancy check (CRC) calculating circuit, a high-frequency circuit, and the like. Each of the first radio communication unit 121 and the second radio communication unit 122 performs modulation/demodulation and frequency conversion of wireless signals transmitted or received by the terminal device 10 and gives received signals to the control unit 190.

The operation accepting unit 130 includes a mechanism used for accepting a user's input operation. More specifically, the operation accepting unit 130 is configured as a touch screen and includes the touch sensitive device 131 and the display 132. The touch sensitive device 131 accepts a user's input operation of the terminal device 10. For example, by using a touch panel of an electrostatic capacitive type, the touch sensitive device 131 detects a user's contact position on the touch panel. The touch sensitive device 131 outputs a signal representing the user's contact position detected using the touch panel to the control unit 190 as an input operation.

The display 132 displays data of an image, a moving image, texts, and the like in accordance with control of the control unit 190. The display 132, for example, is realized using a liquid crystal display (LCD) or an organic electroluminescence (EL) display.

The voice processing unit 140 performs modulation/demodulation of a voice signal. The voice processing unit 140 modulates a signal given from the microphone 141 and gives the signal after modulation to the control unit 190. In addition, the voice processing unit 140 gives a voice signal to the speaker 142. The voice processing unit 140, for example, is realized using a processor used for voice processing. The microphone 141 accepts a voice input and gives a voice signal corresponding to the voice input to the voice processing unit 140. The speaker 142 converts a voice signal given from the voice processing unit 140 into a voice and outputs the converted voice to the outside of the terminal device 10.

The location information sensor 150 is a sensor detecting a location of the terminal device 10 and, for example, is a global positioning system (GPS) module. The GPS module is a reception device that is used in a satellite positioning system. In a satellite positioning system, signals from at least three or four satellites are received, and a current location of the terminal device 10 in which a GPS module is mounted is detected on the basis of the received signals. For example, in the game system 1, in a case in which locations of users who are registered as friends are configured to be able to be referred to, the terminal device 10 can display a list of friends present near a user on the display 132.

The camera 160 is a device for receiving light using light receiving elements and outputting a captured image. The camera 160, for example, is a depth camera that can detect a distance from the camera 160 to an imaging target.

The motion sensor 170 includes an acceleration sensor, an angular velocity sensor, and the like, detects a motion of the terminal device 10, and outputs a sensing result. For example, by placing the terminal device 10 in a mattress of a bed on which a user sleeps or the like, in a case in which a user during sleep is moving on the mattress, the corresponding motion can be detected. By using the sensing result, it can be identified whether a user is sleeping or is awoken, and whether the user during sleep is in a light sleep, a deep sleep, a REM sleep, or a non-REM sleep, and the like.

The storage unit 180, for example, is configured using a flash memory or the like and stores data and programs used by the terminal device 10. In a certain phase, the storage unit 180 stores user information 181 and sleep information 182.

The user information 181 is information of each user in a game based on a game program. As the information of each user, information for identifying the user, a name of the user, a level of the user in a game based on a game program, a current value and a maximum value (an upper limit value) of the stamina value, game objects (including game characters and game items) owned by the user, the amount of virtual currency owned by the user, identification information of other users registered as friends of the user, a setting of attributes of the user, restrictions of game progress imposed in accordance with a sleep state of the user, and the like are included.

The sleep information 182 is information, which is measured by the sleep measuring device 11B or the like, relating to the sleep state of a user. The terminal device 10 receives sensing results of the sleep measuring device 11B and the like by communicating with the sleep measuring device 11B and the like using short-range radio communication such as Bluetooth (a registered trademark), Wi-Fi, or the like. In addition, the sleep measuring device 11B and the like may transmit sensing results to the server 20 without using short-range radio communication in correspondence with communication standards of a mobile communication system such as 5G or the like. The terminal device 10 may receive sensing results acquired by the sleep measuring device 11B and the like from the server 20 that has received the sensing results from the sleep measuring device 11B and the like, generate sleep information 182 using the received sensing results, and store the generated sleep information.

The control unit 190 reads a program stored in the storage unit 180 and executes commands included in the program, thereby controlling the operation of the terminal device 10. For example, the control unit 190 is an application processor. The control unit 190 operates in accordance with a program, thereby exhibiting functions of an input operation accepting unit 191, a transmission/reception unit 192, a data processing unit 193, and a notification control unit 194.

The input operation accepting unit 191 performs a process of accepting a user's input operation on an input device such as the touch sensitive device 131 or the like. The input operation accepting unit 191 judges a type of operation regarding whether a user's operation is a flick operation, a tapping operation, a drag (swiping) operation, or the like on the basis of information of coordinates at which a user has brought his or her finger or the like into contact with the touch sensitive device 131.

The transmission/reception unit 192 performs a process for enabling the terminal device 10 to transmit/receive data to/from external devices such as the server 20, the game controller 11A, the sleep measuring device 11B, and the like in accordance with a communication protocol.

The data processing unit 193 performs a process of performing an arithmetic operation on data of which an input has been accepted by the terminal device 10 in accordance with a program and outputting a result of the arithmetic operation to a memory or the like.

(i) Decrease in stamina value according to game play of quest: For example, when a user selects a quest and performs a game play, the data processing unit 193 performs a series of processes such as decreasing a stamina value and the like. More specifically, a plurality of game units (quests) are displayed on the display 132, and designation of a game unit that is a target for the game play is accepted from a user. In a case in which the current value of the stamina value of a user is above a consumption quantity required for game play of a game unit, the data processing unit 193 starts game play of the game unit. When a user performs game play of the game unit, the data processing unit 193 subtracts a predetermined consumption quantity from the current value of the stamina value. In addition, in a case in which the consumption quantity set to the game unit that is a target of user's game play is larger than the current value of the stamina value of the user (in other words, in a case in which the stamina value is insufficient, and a quest cannot be started), a screen for encouraging consumption of an item and the like that cause the stamina value to be recovered and the like are displayed for the user. Furthermore, in a game based on a game program executed by the terminal device 10, a parameter of the stamina value may not be used, and a user may not consume a stamina value in the game play of the game unit.

(ii) Recovery of stamina value according to elapse of time: The data processing unit 193 performs a process of sequentially recovering the current value of the stamina value up to the maximum value of the stamina value in accordance with elapse of a time.

(iii) Purchase process: The data processing unit 193 accepts a purchase process from a user. For example, by accepting the purchase process, the data processing unit 193 provides non-free virtual currency to a user. In addition, by using the purchase process, the current value of the stamina value may be configured to be recoverable, a specific game object (a game character, a game item, or the like) may be given to a user, or a privilege may be continuously granted to a user (a special login bonus is received). The non-free virtual currency can be used for various purposes and can be used for recovering the current value of the stamina value, obtaining a game object through a lottery, obtaining a game item having an effect on the sleep information 182 by being used, and the like.

The notification control unit 194 performs a process of presenting information to a user. The notification control unit 194 performs a process of causing the display 132 to display a display image, a process of causing the speaker 142 to output a voice, a process of causing the camera 160 to generate vibration, and the like.

<1.2 Functional Configuration of Server 20>

Figure 3:
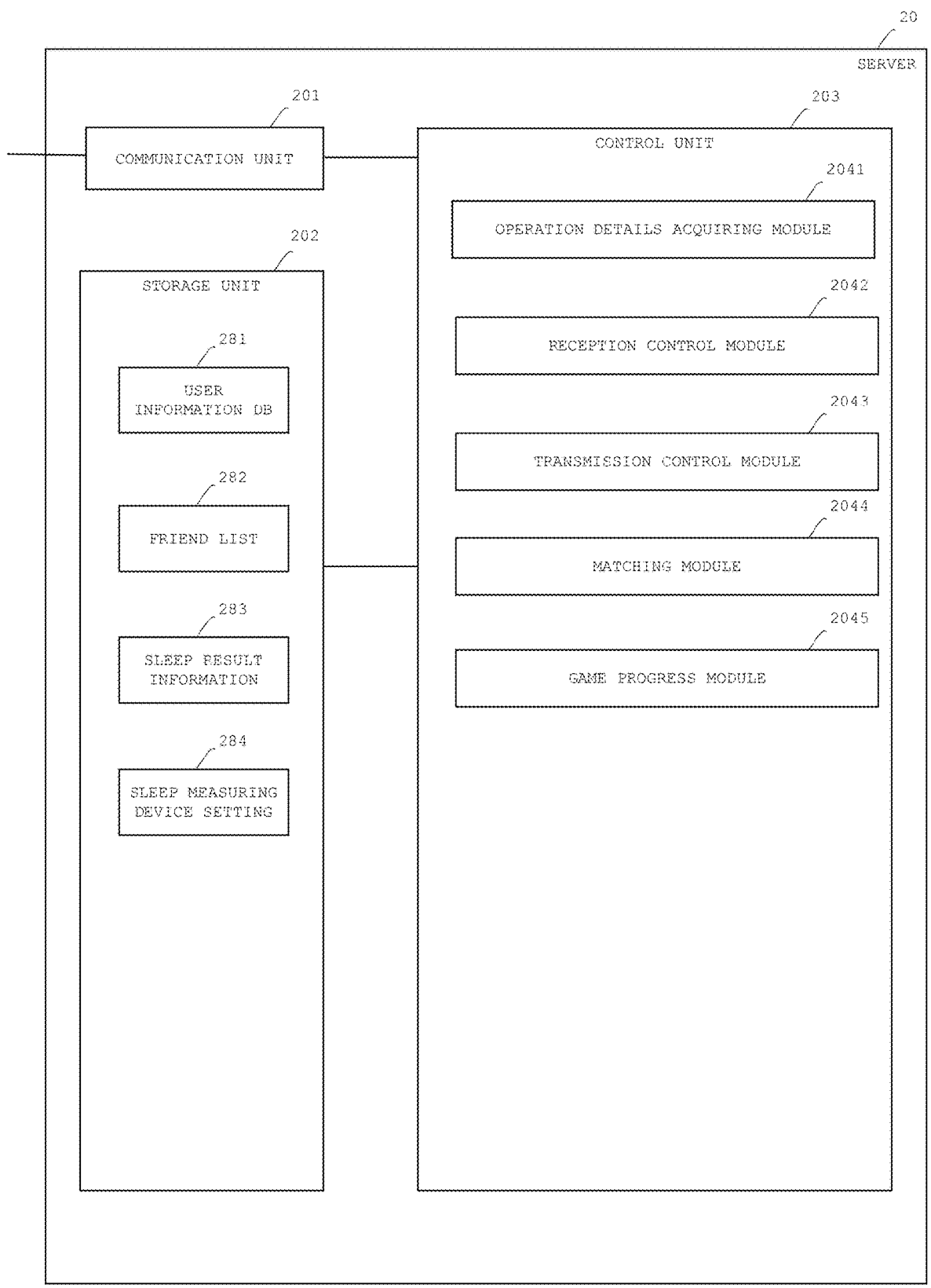
FIG. 3 is a diagram illustrating a functional configuration of a server 20.

FIG. 3 is a diagram illustrating a functional configuration of the server 20. As illustrated in FIG. 3, the server 20 exhibits functions of a communication unit 201, a storage unit 202, and a control unit 203.

The communication unit 201 performs a process for enabling the server 20 to communicate with external devices.

The storage unit 202 stores data and programs used by the server 20. The storage unit 202 stores a user information database 281, a friend list 282, sleep result information 283, a sleep measuring device setting 284, and the like.

The user information database 281 is a database used for storing information of each user in a game based on a game program. Details thereof will be described below.

The friend list 282 is a database used for storing information of users registered as friends by each user. Details thereof will be described below.

The sleep result information 283 is information relating to a sleep of each user. By receiving information relating to a sleep from the terminal device 10 of each user, the server 20 accumulates information about a sleep of each user. Details thereof will be described below.

The sleep measuring device setting 284 stores information for identifying a sleep measuring device, a standard of sensing of a sleep measuring device, and information of an effect exhibited at the time of game play in accordance with the information for identifying a sleep measuring device and the like in association with each of a plurality of sleep measuring devices. Details thereof will be described in another embodiment (Embodiment 5).

The control unit 203 exhibits functions represented as various modules by the processor of the server 20 performing a process in accordance with a program.

An operation details acquiring module 2041 acquires operation details of a user. The operation details acquiring module 2041, for example, acquires a game unit that has been designated by a user as a target for game play and the like as operation details of the user.

A reception control module 2042 controls a process of the server 20 receiving a signal from an external device in accordance with a communication protocol.

A transmission control module 2043 controls a process of the server 20 transmitting a signal to an external device in accordance with a communication protocol.

A matching module 2044 matches users performing multi-play and the like. The matching module 2044, for example, may set friends of a user registered in the friend list as matching targets.

A game progress module 2045 judges whether a user has a stamina value that is sufficient for the user to perform game play of a game unit on the basis of an operation of the user designating the game unit, subtracts a consumption quantity set in the game unit from the current value of the stamina value, and updates the user information DB 281. The game progress module 2045 responds to the terminal device 10 of a user with data required for game play of a game unit (voice data of a character, map data for moving a character, data of an enemy character, and the like).

<2. Data Structure>

FIG. 4 is a diagram illustrating a data structure of the user information database 281, the friend list 282, and the sleep result information 283 stored by the server 20.

As illustrated in FIG. 4, each record of the user information database 281 includes an item "user identification information (user ID)," an item "user name," an item "user level," an item "current stamina value," an item "maximum stamina value," an item "owned game objects," an item "user attribute settings," an item "restriction according to sleep evaluation," and the like in association with information used for identifying a user.

The user information DB 281 includes information of amounts of non-free virtual currency and free virtual currency owned by each user. The free virtual currency represents an amount of virtual currency, which has been provided for free for a user, owned by the user. For example, the terminal device 10 provides free virtual currency for a user in accordance with a login bonus, a reward from an event, and the like. The non-free virtual currency represents an amount of virtual currency, which has been provided for a user for a fee, owned by the user. For example, in accordance with a purchase process, the terminal device 10 accepts a process of purchasing non-free virtual currency and provides the non-free virtual currency for the user. These free virtual currency and non-free virtual currency may have the same name in a game (for example, denoted as "virtual currency (provided for free) and "virtual currency (provided for a fee), and the like) or may have different names.

The item "user identification information (user ID)" is information used for identifying each user.

The item "user name" is a name set by a user.

The item "user level" is a parameter that rises separately from levels of a game character and the like in accordance with a user's repetition of game play. For example, a value set to the item "maximum stamina value" increases in accordance with an increase in the user level. In accordance with this, as the user level further rises, a user can easily play a game unit of which a consumption quantity of the stamina value is larger.

The item "current stamina value" is a current value of the parameter of the action (the current value of the stamina value) of a user. In a case in which a current value of the stamina value is less than the consumption quantity set for a game unit, a user cannot start game play of the game unit. A user can increase the current value of the stamina value by consuming a game item for recovering the stamina value or consuming non-free or free virtual currency. At this time, the current value of the stamina value may be recovered to exceed the maximum value of the stamina value.

The item "maximum stamina value" is a maximum value of the parameter of the action (a maximum or an upper limit of the stamina value) of a user. The current value of the stamina value is recovered up to the maximum value with the passage of time in accordance with elapse of a time.

The item "owned game object" is information of game characters, game items, and the like owned by a user. In this item, information of levels and the like of each of the game characters and each of the game items is also included.

The item "user attribute settings" represents attributes set by a user. The attributes may be set in accordance with a user's operation. For example, in a game, a group to which a plurality of users belong (also referred to as a team, a guild, or the like) can be established. The server 20 assigns unique identification information (a group ID) to the established group and accepts setting of a name of the group from a user belonging to the group. By participating in a group, a user can use each of a function of transmitting/receiving messages to/from members within the group (a bulletin board or the like of the group), a function of performing multi-play with members within the group (a battle, co-fighting, or the like within the group), a function of performing multi-play between groups (a battle, co-fighting, or the like between groups), and the like.

In addition, for example, in a case in which a user and another user have a family relation or the like, the user can designate the other user as a family member. For example, in a case in which a user "C" designates a user "D" as a family member, the user "C" is also set as a family member for the user "D."

In addition, a user can set a group as family members. For example, this group can obtain approval of a user who has established the group or can allow users to be members by limiting the users to users who are set as family members included in the group.

The item "restriction according to sleep evaluation" represents details of various conditions and restrictions set in game play of each user in accordance with information about sleep of the user.

(i) Adjustment of a Game Parameter During Game Play According to Results of Sleep As the conditions set in game play, for example, a game parameter is adjusted such that the progress of a game becomes more advantageous to a user as the user further achieves an object of sleep set for the user. Such a game parameter is not limited to a parameter that is simply given to a user as an item or the like (for example, in a case in which a user achieves an object of sleep, currency in the game is provided or the like). This game parameter, for example, is a parameter that is referred to by a game program during user's game play and may adjust the balance of the game. By using this parameter, a degree of assistance for a user and the like, for example, a degree of difficulty such as a strength of an enemy character, or a degree of easiness in obtaining an item is adjusted.

More specifically, for example, representations in a game are changed in accordance with a time at which a user has awoken (a timing at which the user has woken up from sleep), a time at which the user has gotten up (a timing at which the user has gotten out of bed), a time at which the user has gone to bed (a timing at which the user has entered a bed), a time at which the user has fallen asleep (a timing at which the user has entered sleep), the quality of the sleep of the user, and the like. At the timing at which a user has gotten up, the user has awoken from sleep, and thus "the user has gotten up" may include "the user has awoken." Similarly, "the user has fallen asleep" may include "the user has gone to bed." For example, in a case in which a user has gotten up in accordance with a target time, the user is allowed to obtain items in the game more easily. For example, in a case in which a user purchases an item during game play, a unit price for purchase of an item is lowered, in a case in which a user sells an item during game play, the number of chances for purchase is increased, or the like. In addition, a time frame in which game play becomes advantageous to a user may be set regardless of information of times relating to sleep (a getting-up time and a falling-asleep time) of the user. For example, in a case in which a time at which a user has gotten up is 7:00 a.m. and satisfies a planned getting-up time set in advance, such as a time between 10:00 a.m. and 12:00 p.m., game play of the user may be set to be advantageous in a time frame different from the timing at which the user has gotten up.

(ii) Adjustment of Chance of Game Play of User According to Result of Sleep (a) Availability/unavailability of game play: As a restriction set in a game play, for example, as a user achieves an object of sleep set for the user, a specific game unit (also referred to as a "quest" or the like) may be set to be playable. For example, as a user achieves an object of sleep for a game unit of which a reward at the time of clearing the game unit is relatively high, a game unit of which a degree of difficulty is high, a game unit provided as an event over a predetermined period by an operator of the game, or the like as a target, game play of the user may be enabled, or the number of times game play can be performed may be increased.

(b) Variation in period in which game play can be performed: In accordance with whether or not an object of sleep set for a user has been achieved, a period in which game play of a specific game unit can be performed may be adjusted. For example, although a user can perform game play of a specific game unit regardless of whether or not the user has achieved an object of sleep, in accordance with the user's achievement of the object of sleep, a period in which the specific game unit can be played by the user may be set to be long, or game play may be set to be performable in a specific time frame such as a time frame designated by the user or the like.

(iii) Adjustment of User's Operation Chance/Action During Game According to Result of Sleep As a restriction on a user, a chance to perform a specific operation may be set for the user in accordance with a result of sleep of the user. For example, as a user achieves an object of sleep, an operation of receiving a reward such as a presentation item or the like may be configured to be able to be performed by the user (a period in which the operation can be performed may be set).

In addition, as a restriction on a user, in accordance with a result of sleep of the user, specific actions during a game may be configured to be able to be performed by the user. The specific actions during a game are transfer of an item, obtainment of an item, a battle with a character other than a player character, and the like. For example, a user is allowed to transfer a specific item and the like to another user, a non-player character (NPC), or the like only in a case in which the user is during sleep. Details will be described below.

Each record of the friend list 282 includes an item "user 1," an item "user 2," an item "friend registration date," an item "disclosure/non-disclosure of sleep information," an item "common attributes," an item "common sleep time," and the like.

The item "user 1" represents one user out of users registered as mutual friends.

The item "user 2" represents the other user out of users registered as mutual friends.

The item "friend registration date" represents a date and time at which the users were registered as friends.

The item "disclosure/non-disclosure of sleep information" represents a setting indicating whether or not information about sleep of each user is disclosed among users registered as friends. For example, there are settings such as "non-disclosure" prohibiting disclosure among users registered as friends, "mutual disclosure" for disclosure between friends, "disclosure to one side" for disclosure from one user to the other user, and the like.

The item "common attributes" represents attributes common to users among attributes set for the users registered as friends. For example, there are a case in which users registered as friends are "family members," a case in which the users belong to the same "group," and the like.

The item "common sleep time" represents a time frame that is a time in which users registered as friends both sleep. In other words, it is a time frame in which users both asleep.

In addition, a method for registering friends in which one user requests friend registration from the other user, and in a case in which the other user approves the request, the other user is registered in the friend list may be configured. Furthermore, one user may add (follow) the other user to the list even when there is no approval from the other user. In such a case, by both the users following each other, a mutually-following state is formed.

Each record of the sleep result information 283 includes an item "user identification information," an item "date and time," an item "sleep object," an item "sleep result," an item "sleep evaluation parameter," an item "sleep measuring device," an item "quality of measurement," an item "sleep location," and the like.

The item "user identification information (user ID) is information for identifying each user.

The item "date and time" represents a timing at which the sleep measuring device 11B and the like perform sensing in accordance with a user's sleep.

The item "sleep object" represents an object value for which a user performs sleep. For example, as an object value for which sleep is performed, information of a time at which a user has fallen asleep and a time at which the user has gotten up are included.

The item "sleep result" represents a result value of sleep of each user recorded by a user performing sleep and performing sensing using the sleep measuring device 11B and the like. As a result value of sleep, for example, a time at which a user has fallen asleep and a time at which a user has gotten up are included.

The server 20 receives information about a result of sleep from the terminal device 10 of each user and updates the sleep result information 283. The time at which a user has fallen asleep may be identified on the basis of sensing results of the sleep measuring device 11B and the like or may be a timing at which an operation representing start of falling asleep has been received from the user or the like. The time at which a user has gotten up may be identified on the basis of sensing results of the sleep measuring device 11B and the like or may be a timing at which an operation representing getting up has been received from the user or the like.

The item "sleep evaluation parameter" is an evaluation parameter acquired by evaluating a result of sleep of a user. For example, in accordance with a sleep time reaching a target time, the quality of sleep being good, and the like, the value of the evaluation parameter may be set to be good. This evaluation parameter may be a visualization of the value of a so-called sleep debt in accordance with a result of sleep of a user.

The server 20 receives information about a result of sleep from the terminal device 10 of each user and calculates the evaluation parameter for each user. The server 20 provides a game play using the evaluation parameter for the user. For example, to encourage achievement of an object of sleep set for a user, in a case in which the evaluation parameter is not good (e.g., in a case in which the sleep of the user is not appropriate, and insufficient sleep is sensed or the like), the server 20 or the terminal device 10 adjusts various parameters for lowering the efficiency of the game play of the user and notifies the user to encourage the user to sleep more appropriately.

For example, in a case in which the sleep of a user is not good, the terminal device 10 notifies the user of a notification "Your body is tired; you should go to sleep," to encourage the user to sleep. In addition, even when a user performs game play, by lowering a degree of easiness in acquisition of an experience value, a game item, or the like, the terminal device 10 changes the environment of the game play such that the efficiency of the user's game play is lowered. In accordance with this, even in a case in which a user performs a game play while tired, the user can be caused to recognize that the game is not efficiently progressing, and sleep can be encouraged such that the sleep of the user improves.

In addition, this evaluation parameter may represent how good a body condition of a user is. The terminal device 10 or the server 20 can present game play according how good the body condition of a user is to the user on the basis of this evaluation parameter. For example, in a case in which a user has had sufficient sleep, it is understood that it is healthy for the body of the user to be appropriately tired. For this reason, in response to a user having had sufficient sleep, the terminal device 10 or the server 20 can select a game that requires motion of the body of the user among a plurality of game candidates and give a notification encouraging game play of the game. For example, in game play of a certain game, by identifying that the body condition of a user is good on the basis of a result of sleep of the user, game play of another game (for example, a game that progresses in accordance with walking of the user) can be presented to the user. In addition, by identifying that the body condition of a user is not good on the basis of a result of sleep of the user, game play of another game (for example, a game that progresses even when the user does not move) can be presented to the user.

The item "sleep measuring device" represents information used for identifying a sleep measuring device used for measuring sleep by a user. FIG. 4 illustrates an example in which the same user records information about sleep using a plurality of sleep measuring devices. In this item "sleep measuring device," the information used for identifying a sleep measuring device may be information representing a type (information of a manufacturer or information identifying a product) of the sleep measuring device or may be information uniquely identifying each of these sleep measuring devices (for example, a media access control (MAC) address, a unique code assigned by a manufacturer or the like of a sleep measuring device) or the like.

The item "quality of measurement" represents quality of a sensing result measured by the sleeping measuring device. Here, (1) the quality of a sensing result may represent accuracy of sensing of a sensor device mounted in the sleep measuring device. A sensing result may vary in accordance with a type of sensor device mounted in the sleep measuring device. In addition, even in a case in which different sleep measuring devices use the same sensor devices, the accuracy of sensing may decrease in accordance with a malfunction of the sensor device. Furthermore, (2) also in a case in which quality of a communication signal sent out from a sleep measuring device deteriorates, the quality of an output sensing result may be degraded. In addition, the quality of a sensing result may represent (3) whether or not a sleep state of a user was able to be measured well separately from the accuracy of sensing of the sensor device or the quality of a communication signal. For example, in a case in which a bed of a user vibrates due to a factor other than the user, the sleep state of the user may not be able to be measured well, and an error may be acquired. For example, in a case in which another user, a pet, or the like is present on the bed of a user, a sensing result may vary due to a factor other than the user. In addition, (4) the quality of a sensing result may represent quality of an application used in the sleep measuring device for calculating the sleep information 182 using the sensing result. For example, when the same sensing result is acquired, in a case in which a calculation algorithm used for deriving the sleep information 182 is different, the sleep information 182 that is a calculation result may vary.

The item "sleep location" represents a location at which a user has slept. For example, in a case in which the sleep measuring device 11B and the like include a location information sensor (a GPS or the like), a location in which the user has slept may be acquired using an output result of the location information sensor. In addition, in a case in which the sleep measuring device 11B and the like communicate with the terminal device 10 through short-range radio communication or the like, a location at which the user has slept may be acquired using an output of the location information sensor 150 of the terminal device 10. In addition, the sleep measuring device 11B and the like or the terminal device 10 may identify a location of the sleep measuring device 11B and the like or the terminal device 10 by communicating with a wireless LAN access point or a wireless base station and regard the identified location as a location at which the user has slept.

<3 Operation>

Hereinafter, a game process performed by the terminal device 10 will be described.

<3. 1 Operation Example 1>

FIG. 5 is a flowchart illustrating a process in which a user performs game play by consuming a consumption quantity set in a game unit from a current value of the stamina value by designating the game unit, and a reward at the time of clearing the game unit is set as details according to a result of sleep of the user.

In Step S501, the terminal device 10 displays quests that are play units on the display 132 and accepts selection of a quest from a user.

In Step S503, the terminal device 10 judges whether or not the current value of the stamina value of the user is above a stamina consumption quantity set to the quest designated by the user. In a case in which the current value of the stamina value of the user is above the stamina consumption quantity of the quest, the terminal device 10 transmits a signal representing start of a game play of the quest to the server 20. The terminal device 10 subtracts the stamina consumption quantity set to the quest from the current value of the stamina value of the user.

In Step S553, the server 20 subtracts a consumption quantity from the stamina value of the user on the basis of the consumption quantity set to the quest designated by the user and updates the user information DB 281.

In Step S505, the terminal device 10 causes a game play of the quest designated by the user to progress in accordance with an input operation of the user.

In Step S507, the terminal device 10 judges whether or not an end condition that the quest is satisfied (for example, a condition that a game character operated by the user defeats a boss character set to the quest, a condition that a game character operated by the user becomes unable to fight, or the like) and, in a case in which the quest ends, updates various parameters. For example, the terminal device 10 updates various parameters by increasing an experience value of the user, providing the user with a drop item set to the quest, and the like. Here, in a case in which it is judged that the end condition of the quest is satisfied, the terminal device 10 judges whether or not a result of sleep satisfies a condition set in advance on the basis of the sleep information of the user of the sleep result information 283. For example, in a case in which a result of actual sleep of the user has reached an object of sleep that is set in advance by the user (an object of a bed time, a falling-asleep time, an awaking time, a getting-up time, and quality of sleep), the terminal device 10 judges that the result of the sleep satisfies the condition. In other words, the terminal device 10 judges that the quality of sleep of the user is good.

In a case in which the condition is not satisfied, the terminal device 10 sets details of a reward at the time of clearing the quest for a first reward. In a case in which the condition is satisfied, the terminal device 10 sets details of a reward at the time of clearing the quest for a second reward that is more advantageous to the user than the first reward. For example, the second reward becomes more advantageous to the user than the first reward in accordance with a more experience value acquired at the time of clearing the quest, more currency in the game, better or more game items, or the like.

In Step S555, the server 20 updates the user information DB 281 on the basis of the update result of various parameters of the user.

As above, by getting regular sleep, a user can obtain a reward in a game and is encouraged to have an appropriate sleep habit. In addition, by clearing a quest after starting a game, a reward according to sleep is provided, and thus a user can further enjoy game play after getting up while a sleep is taken.

<3.2 Operation Example 2>

Figure 6:
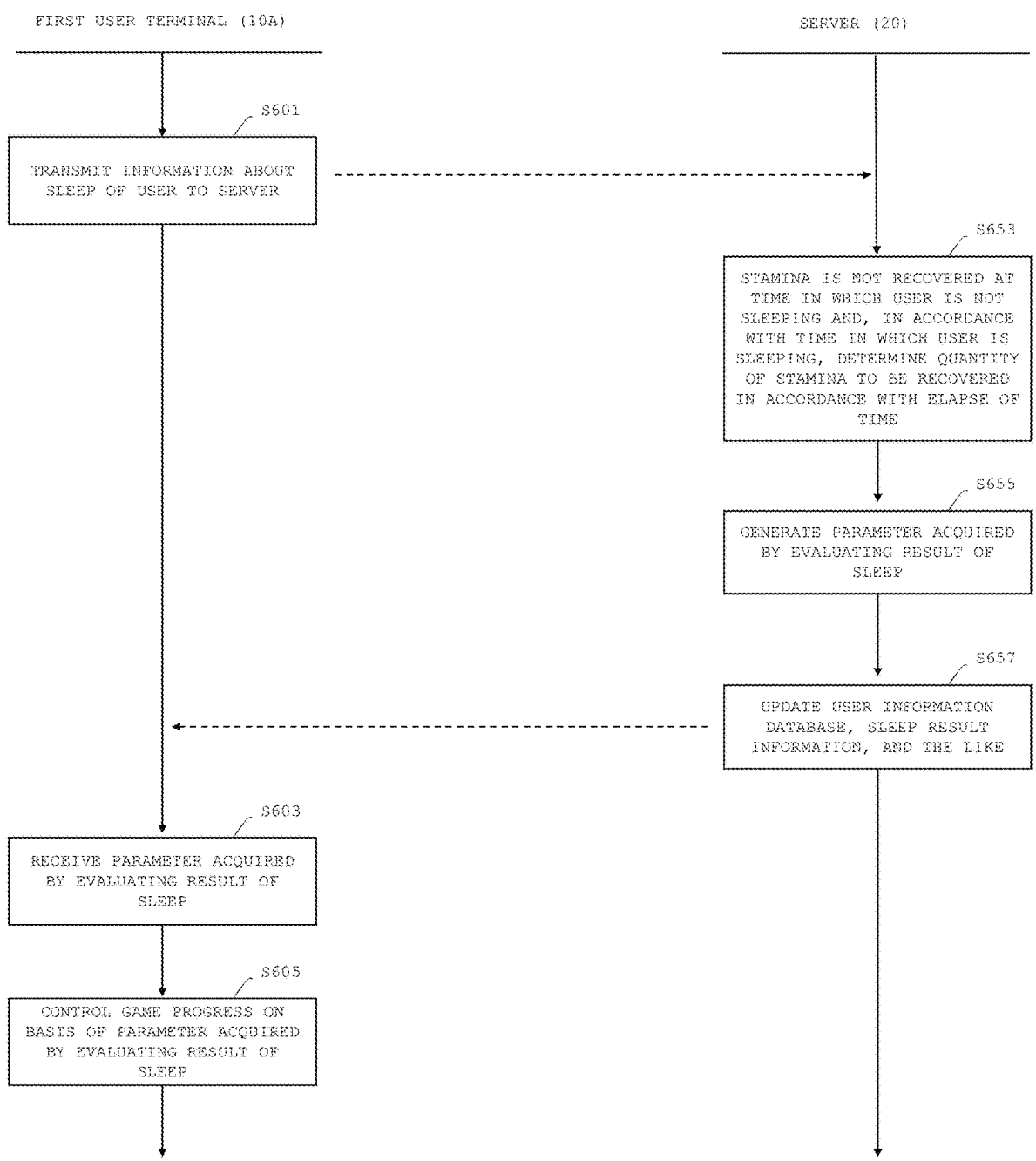
FIG. 6 is a flowchart illustrating a process of recovering a stamina value of a user in a case in which the user is during sleep.

FIG. 6 is a flowchart illustrating a process of recovering a stamina value of a user in a case in which the user is asleep.

In Step S601, the terminal device 10 transmits information about sleep of a user to the server 20. The terminal device 10 transmits information of a time at which the user has gone to bed, a time at which the user has started to fall asleep, a time at which the user has awoken, a time at which the user has gotten up, and quality of sleep to the server 20 as information about sleep of the user.

In Step S653, the server 20 recovers the current value of the stamina value of the user with in accordance with elapse of a time in which the user is sleeping and does not recover the current value in a time in which the user is not sleeping (for example, a time from a time at which the user has gotten up to a time at which the user has fallen asleep) by referring to the user information DB 281.

In addition, in Step S653, the current stamina value may also be recovered with the passage of time in a time in which the user is not sleeping, but more of the stamina value may be recovered with the passage of time in a time in which the user is sleeping. For example, a recovery quantity of the stamina value with the passage of time in a case in which the user has been up all day long (is not sleeping) is set as a quantity for which a predetermined game unit can be played a predetermined number of times. In accordance with this, the user can be encouraged to sleep while the number of times of game play of the game unit per day is limited.

In Step S655, the server 20 generates an evaluation parameter acquired by evaluating a result of sleep of the user.

In Step S657, the server 20 updates the sleep result information 283 on the basis of information of the result about sleep of the user received from the terminal device 10 and the evaluation parameter generated in Step S655.

In Step S603, the terminal device 10 receives the evaluation parameter acquired by evaluating the result of sleep from the server 20.

In Step S605, the terminal device 10 controls game progress of the user on the basis of the evaluation parameter.

As above, after consuming a stamina value by playing the game unit, the user can recover the current value of the stamina value by sleeping. Thus, the user can be encouraged to get appropriate sleep while enjoyment according to game play is realized.

<3.3 Operation Example 3>

Figure 7:
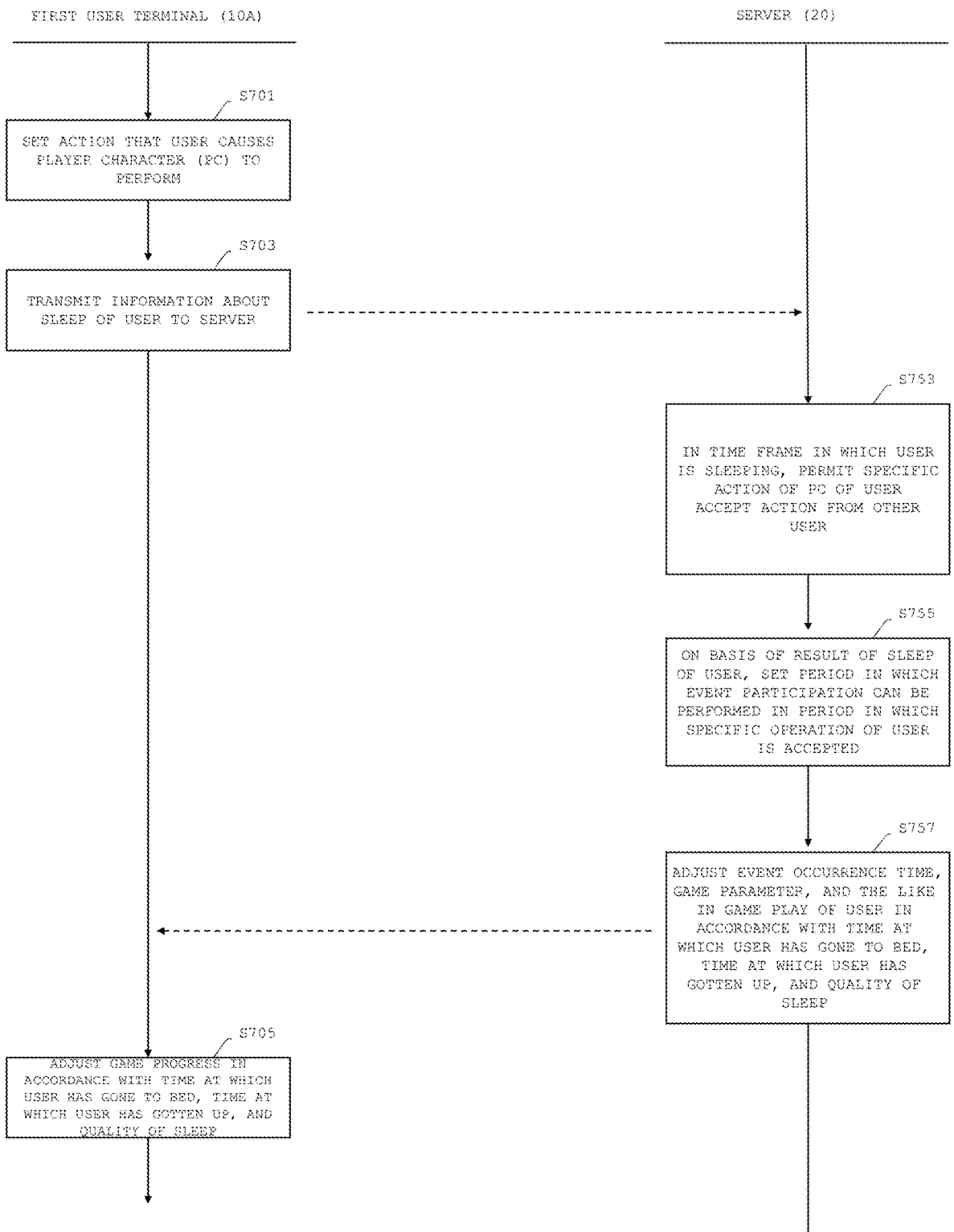
FIG. 7 is a flowchart illustrating a process of the terminal device 10 causing game play of a user to progress on the basis of information about sleep of the user.

FIG. 7 is a flowchart illustrating a process of the terminal device 10 causing game play of a user to progress on the basis of information about sleep of the user.

In Step S701, the terminal device 10 sets an action to be performed during sleep of a user (for example, transfer of an item, a battle with another character, or the like) to a player character (PC) that is an operation target for the user in accordance with a user's operation or in accordance with a predetermined rule rather than a user's operation.

In Step S703, when it is detected that the user has fallen asleep (or has gone to bed) on the basis of sensing results acquired by the sleep measuring device 11B and the like, the terminal device 10 transmits information about sleep of the user to the server 20.

In Step S753, the server 20 receives the information about sleep of the user from the terminal device 10. The terminal device 10 permits the player character of the user to perform the action set in Step S701 in a time frame in which the user is sleeping. The server 20 accepts actions of a character of another user and a non-player character (NPC) for the player character of the user. For example, in a case in which the player character of the user sells an item or the like, a process of the NPC or the like purchasing the item or the like is performed in a time frame in which the user is sleeping. Thus, by appropriately sleeping, the user can cause the game to progress.

In Step S755, the server 20 sets a period in which a specific operation is accepted from a user and a period in which the user can participate in a specific event on the basis of results of sleep (a bed time, a falling-asleep time, an awaking time, a getting-up time, and quality of sleep) of the user. The server 20, for example, performs a process of providing a period in which an operation for receiving a reward can be performed, providing a period in which a user can participate in an event, lengthening of such periods, and the like by a user appropriately sleeping.

In Step S757, the server 20 adjusts a time at which a specific event occurs, a specific game parameter, and the like when a user performs game play on the basis of results of sleep of the user. For example, in a case in which the time at which the user has gotten up is a specific time (for example, in a case in which the user sets getting-up at 07:00 a.m. as an object and actually gets up at 07:00 a.m.), the server 20 performs a process of causing game progress to be advantageous to the user, causing an event to easily occur, performing a representation in a game at a specific time, and the like.

In Step S705, the terminal device 10 adjusts the game progress on the basis of the results of sleep of the user.

As above, when a user appropriately sleeps, progress of game play can be performed, the game play becomes advantageous, and a user's specific operation can be easily performed in game play. Thus, enjoyment according to the game play can be further improved while the user is encouraged to get appropriate sleep.

<3.4 Operation Example 4>

Figure 8:
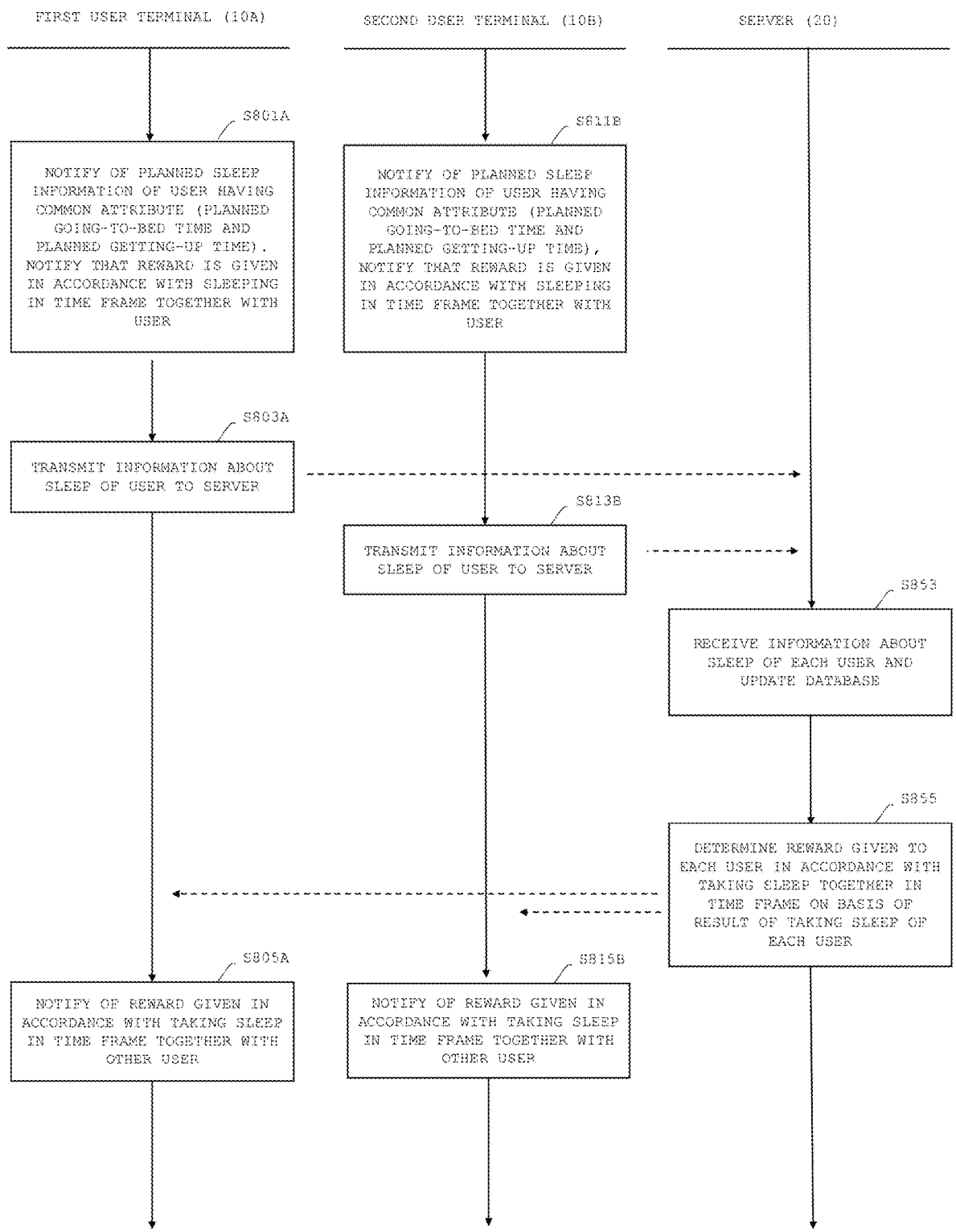
FIG. 8 is a flowchart illustrating a process of causing game progress of each user to be advantageous and giving a reward for each user, and the like in accordance with a plurality of users achieving an object of sleep.

FIG. 8 is a flowchart illustrating a process of causing game progress of each user to be advantageous and providing a reward for each user, and the like in accordance with a plurality of users achieving an object of sleep. In the example illustrated in FIG. 8, a first user operates a terminal device 10A, and a second user operates a terminal device 10B. The first user and the second user have a common attribute and, more specifically, are friend users registered as family members.

In Step S801A, the terminal device 10A notifies the first user of planned sleep information (a planned bed time and a planned getting-up time) of the second user having the attribute common to the first user. The terminal device 10A notifies the first user that a reward that can be used in game play is given by the first user taking sleep in a sleep object time frame set to the second user.

In Step S811B, the terminal device 10B notifies the second user of planned sleep information of the first user having the attribute common to the second user. The terminal device 10B notifies the second user that a reward that can be used in game play is given by the second user taking sleep in a sleep object time frame set to the first user.

In Step S803A, when it is detected that the first user is sleeping, the terminal device 10A transmits information about sleep of the first user to the server 20.

In Step S813B, when it is detected that the second user is sleeping, the terminal device 10B transmits information about sleep of the second user to the server 20.

In Step S853, the server 20 receives information about sleep of the first user and the second user from the terminal device 10A and the terminal device 10B and updates the sleep result information 283.

In Step S855, the server 20 determines rewards to be given to the first user and the second user in accordance with a relationship between sleep times of the first user and the second user (more specifically, the first user and the second user take sleep in a time frame together) by referring to results of sleep taken by the first user and the second user and notifies the terminal device 10A and the terminal device 10B of details of the determined rewards. In addition, as the relationship between sleep times of the first user and the second user, in accordance with time frames of sleep between the first user and the second user overlapping each other for a predetermined time or more, a reward given to each user may be determined. In addition, in accordance with both the first user and the second user sleeping in the overlapping time frame, a reward may be given to each user. Furthermore, in accordance with time frames of sleep between the first user and the second user not overlapping each other, a reward may be given to each user. A user to which a reward is given may be any one of the first user and the second user. For example, a reward may be given to a user who has taken a more appropriate sleep out of the first user and the second user.

In Step S805A, the terminal device 10A notifies the first user of the reward given in accordance with the first user having taken sleep in a time frame in which the second user also has taken sleep.

In Step S815B, the terminal device 10B notifies the second user of the reward given in accordance with the second user having taken sleep in a time frame in which the first user also has taken sleep.

In the process described above, both the first user and the second user may set a common object (a bed time and a getting-up time) of sleep, and, by both the users achieving the object of sleep, a reward may be given to each of the users. In addition, both the first user and the second user (or one of the first user and the second user) may give a notification of an object of sleep. For example, by operating the terminal device 10A, the first user may transmit a message presenting an object of sleep such as "Let's sleep from 22:00 p.m. to 07:00 a.m." to the terminal device 10B operated by the second user. Here, in accordance with the second user performing an operation of reading this message or the like, an object of sleep is set to the first user and the second user. In addition, the terminal device 10B may notify the terminal device 10A of the first user of the second user having read the message. In accordance with this, both the first user and the second user are encouraged to take sleep for achieving an object of sleep.

In addition, a reward given to a user in a case in which an object of sleep is achieved may be set by another user. For example, a reward given to the second user in a case in which the second user achieves an object of sleep can be set by the first user. In accordance with this, for example, in a case in which the first user is a parent of the second user, by a child (the second user) taking sleep as an object while the parent (the first user) presents the object of sleep to the child (the second user), a reward is given to the child (the second user). Here, in a case in which a reward given in accordance with the second user achieving the object of sleep is set by the first user, the terminal device 10A may extract recommendation of a reward presented by the first user to the second user using results and the like of game play of the second user and display the recommendation. For example, a list of game objects relating to player characters of which use frequencies are high among player characters used in game play by the second user (for example, equipped items of player characters of which use frequencies are high, an item that can proceed to a senior position, an evolved material, and the like) may be presented to the first user as a recommendation of a reward set to the second user.

In this way, a plurality of users are encouraged to jointly achieve an object of sleep, and, by further giving a reward in accordance with a plurality of users taking sleep together, the enjoyment of a game can be further improved.

<4 Screen Example>

Figure 9:
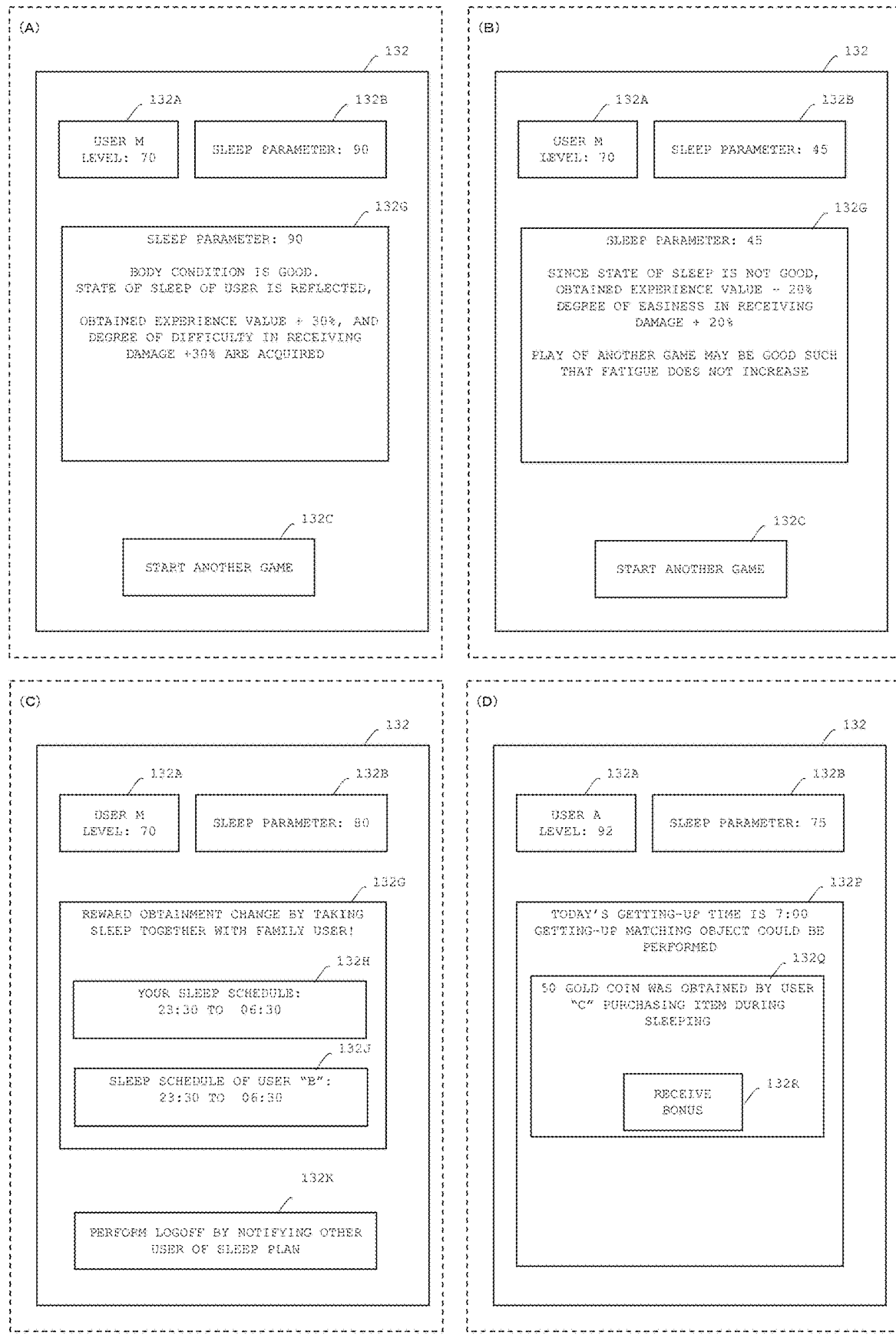
FIG. 9 is a diagram illustrating screen examples of the terminal device 10.

FIG. 9 is a diagram illustrating screen examples of the terminal device 10.

A screen example (A) illustrated in FIG. 9 is a diagram illustrating a phase in which an evaluation parameter is generated by evaluating a result of sleep of a user, and game play using the evaluation parameter is performed. This corresponds to Steps S657, S603, and S605 illustrated in FIG. 6.

As illustrated in the screen example (A), the terminal device 10 displays a user level 132A, an evaluation parameter 132B, a game start button 132C, and a notification display section 132G on the display 132.

The user level 132A represents a level of a user performing game play as a player. In accordance with a user performing game play, the terminal device 10 gives an experience value (a player experience value) not to a game character but to the user himself or herself. In accordance with the level as a player being leveled up, the terminal device 10 recovers the stamina value or raises the maximum value of the stamina value.

The evaluation parameter 132B is a region for displaying an evaluation parameter acquired by evaluating a result of sleep of a user.

The notification display section 132G is a region in which details controlling game progress are notified to a user on the basis of the evaluation parameter (it is a parameter acquired by evaluating a result of sleep of a user and thus is also a parameter representing a degree of goodness of a condition of the user). In the screen example (A), the terminal device 10 displays a notification representing that the condition of the user is good (display of "Condition is good." Or the like) in accordance with the evaluation parameter (a sleep parameter). In accordance with the value of the evaluation parameter of a user being good, an experience in which goodness of the condition of the user is reflected also in game play can be provided. More specifically, the terminal device 10 notifies a user of an indication representing that game progress becomes advantageous to the user in the notification display section 132G such as an experience value acquired by the user in game play being increased, the user becoming difficult to receive a damage in a case in which the user battles with an enemy character using a player character, or the like.

The game start button 132C is a region for accepting an operation for starting another game other than a game program that is being executed by the terminal device 10 from the user.

For example, in a case in which the condition of the user is good, the user is encouraged to move his or her body, whereby the condition of the user can be better. Thus, in a case in which the value of the evaluation parameter is good, in response to acceptance of a user's operation on the game start button 132C, the terminal device 10 may perform display encouraging the user to start another game program encouraging the user to move his or her body (for example, a game that uses map information and progresses in accordance with a user moving in a real world or the like). The terminal device 10 starts another game program in response to a user's start operation.

In addition, there are cases in which the evaluation parameter is not good, and the condition of a user is not good.

A screen example (B) illustrates an example of display of a screen displayed in a case in which the condition of a user is not good. The terminal device 10 notifies a user of an indication representing that game progress becomes disadvantageous to the user in the notification display section 132G such as an experience value acquired by the user in game play being decreased, the user becoming easy to receive a damage in a case in which the user battles with an enemy character using a player character, or the like. In addition, as illustrated in the notification display section 132G, the terminal device 10 may give a notification for encouraging a user to play another game such that fatigue accumulated in the body of the user does not increase.

As above, an example in which another game is started in response to a user's operation on the game start button 132C has been described. Here, the value of the evaluation parameter may be a parameter that can be used to be common to a plurality of game programs by a user. The terminal device 10 may be configured to display a list of game programs for which the value of the evaluation parameter can be used by a user and accept designation of a game program to be executed from the user.

In addition, at least any one of the terminal device 10 or the server 20 may accumulate and manage evaluation parameters generated in accordance with a user taking sleep day by day. The terminal device 10 and the server 20 may provide a plurality of games that can use these accumulated evaluation parameters for a user by using the values of the accumulated evaluation parameters. For example, a user ID is issued to a portal site or the like, and an accumulated value of evaluation parameters accumulated by a user can be managed in association with the user ID. The evaluation parameter can be used in various forms in each of a plurality of games. For example, a game item that can be obtained by only consuming the evaluation parameter can be provided. In addition, for example, a specific game process may be configured to be able to be performed using the evaluation parameter instead of virtual currency.

In accordance with this, a user is encouraged to take sleep day by day such that the object of sleep is achieved.

A screen example (C) is a diagram illustrating a phase in which a plurality of users are encouraged to achieve an object of sleep. This corresponds to each process illustrated in FIG. 8.

As illustrated in the screen example (C), the terminal device 10 displays planned sleep information 132H and a friend sleep plan 132J in the notification display section 132G. The terminal device 10 displays a notification button 132K.

The terminal device 10 performs display for encouraging a user to take sleep in a time frame of sleep of another user in the notification display section 132G. At this time, planned sleep information (a plan of a bed time and a getting-up time) of the user of the terminal device 10 is displayed in the planned sleep information 132H. In addition, information of a sleep plan of another user (in the screen example (C), a family member) having an attribute common to the user is displayed in the friend sleep plan 132J.

The notification button 132K is a region for accepting an operation performed when the user starts sleep. After performing an input operation on the notification button 132K, the user starts to take sleep. In order to inhibit an operation on the terminal device 10 although the user is to take sleep, the terminal device 10 may not accept an input operation on the terminal device 10 until a planned getting-up time of the user in response to a user's input operation on the notification button 132K.

The terminal device 10 notifies another user having an attribute common to the user of an indication representing that the user is to take sleep in response to a user's input operation on the notification button 132K.

A screen example (D) illustrates a phase in which, in accordance with a user taking sleep according to an object of sleep, the terminal device 10 causes a player character to perform specific game action during the sleep, and a result of the game action is displayed after the user gets up. This corresponds to each process illustrated in FIG. 7.

The terminal device 10 displays a notification display section 132P, a message 132Q, a reception operation accepting section 132R, and the like.

The notification display section 132P displays whether or not a user has taken sleep according to an object of sleep. In the example illustrated in the drawing, the terminal device 10 displays that that user was able to get up at a planned getting-up time that is an object of sleep in the notification display section 132P.

The message 132Q is a region in which details of a game action performed by a player character during sleep are displayed as a result of a user who has taken sleep according to the object of sleep. In the example illustrated in the drawing, the terminal device 10 causes a player character to perform a specific game action (sale of an item or the like) during sleep of the user and displays that purchase of an item has been accepted from another user (user "C"), and a reward thereof has been received using currency in a game.

The reception operation accepting section 132R is a region for accepting a user's operation for receiving a reward given to the user. In a case in which sleep of the user reaches an object, a reward may be received using the reception operation accepting section 132R.

Summary

As above, according to this embodiment, in accordance with a user appropriately taking sleep, game progress of the user becomes advantageous. As a specific form in which game progress becomes advantageous, there is a fain in which a user performs game play at the time of getting up and, when a clearing condition for a game unit is satisfied, a reward at the time of clearing becomes more advantageous to the user as the sleep of the user is more appropriate.

In accordance with this, by giving a reward at the time of clearing a game unit while encouraging the user to take appropriate sleep, an incentive for playing the game is also provided for the user.

<Modification>

(1) In description of FIG. 8 and the like, an example in which the first user and the second user present objects of sleep to each other, take sleep, and a reward is given in accordance with achievement of each of the objects of the sleep has been described. Besides this, there are cases in which periods in which the first user and the second user take sleep are different from each other. In accordance with the second user performing game play during a period in which the first user is sleeping, a reward may be given to at least one of the first user and the second user. In accordance with this, while the first user is encouraged to take sleep such that he or she reaches the object of sleep, the enjoyment of game play of the second user can be further improved.

(2) In FIGS. 4, 8, 9, and the like, various attributes such as a group and the like have been described as being set for a user. As the group, a "family" and the like have been described. Besides this, a reward given in a case in which a user achieves an object of sleep may be set to details according to the attribute of the user. For example, in FIG. 8 and the like, a reward given in a case in which a plurality of users who are family members achieve an object of sleep and a reward given in a case in which users of a group that is not a family but a guild or the like achieves an object of sleep may be different from each other.

(3) In the embodiment described above, it has been described that the terminal device 10 detects that a user has gone to bed and that a user has fallen asleep after going to bed. In this case, the terminal device 10 may give a reward to a user in accordance with the user falling asleep without accepting an input operation on the terminal device 10 after the user goes to bed. A user going to take sleep can be assisted to achieve a sleep object without operating the terminal device 10.

Second Embodiment

As above, in the first embodiment, an example in which various rewards are given to a user in a game in accordance with the user achieving the object of sleep has been described. In a second embodiment, the followings will be described.

(1) Technology for Handling User's Operation on Terminal Device 10 Before Falling Asleep Although a user goes to bed and is going to fall asleep, the user may not fall asleep at all by operating the terminal device 10 or the like due to having nothing to do, concern for a notification to the terminal device 10, and the like. By user's viewing emission of a backlight of the display 132 of the terminal device 10, the user may be distracted from falling asleep, and there is concern that the habit of sleep may not be appropriate.

Thus, a technology for inhibiting a user from operating the terminal device 10 before falling asleep is necessary.

In Embodiment 2, a technology for encouraging a user not to operate the terminal device 10 before the user falls asleep from a state in which the user has gone to bed (a state in which the user lies down on a bed without falling asleep) will be described.

(2) Technology for Giving Notification for Encouraging User to Take Sleep at Appropriate Timing In case of a technology for notifying a user of a planned sleep time set in advance through a push notification or the like for the user, if the push notification is performed in a time frame in which the user is sleeping, there is concern that the sleep of the user may be rather distracted.

Thus, in Embodiment 2, a technology for giving a notification for encouraging a user to take sleep in an appropriate time frame will be described.

(3) Technology for Encouraging a User to Move for Appropriately Taking Sleep on the Basis of Information of the Current Location of User In a case in which a user is away from a place for taking sleep such as a case in which the user is out, there is concern that it becomes difficult for the user to take sleep even when a planned bed time arrives.

Thus, in Embodiment 2, a technology for giving a notification to a user with the current location of the user taken into account for assisting sleep of the user will be described.

Figure 10:
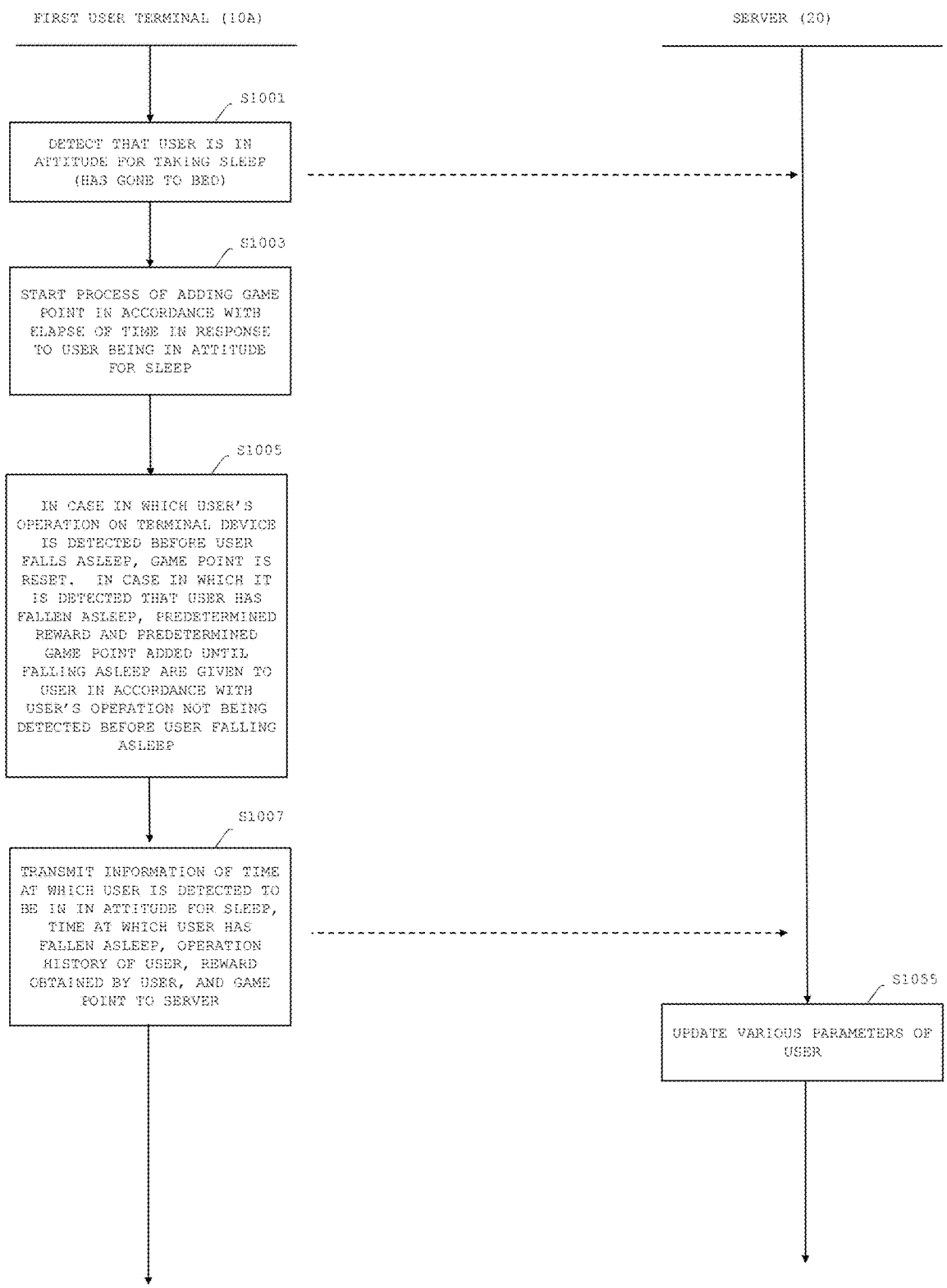
FIG. 10 is a flowchart illustrating a process of giving a reward to a user in a game in accordance with no operation of the terminal device 10 before the user falls asleep.

FIG. 10 is a flowchart illustrating a process of giving a reward to a user in a game in accordance with no operation on the terminal device 10 before the user falls asleep.

In Step S1001, the terminal device 10 detects that a user is in an attitude for sleep (for example, the user has gone to bed such as the user horizontally lies down on the bed) on the basis of outputs of the sleep measuring device 11B and the like and the motion sensor of the terminal device 10.

In Step S1003, the terminal device 10 initializes a game point in response to detection of the user being in the attitude for sleep in Step S1001 and starts a process of changing the game point in accordance with elapse of time. For example, every time when a predetermined time elapses, the terminal device 10 adds a predetermined value to the game point.

In Step S1005, the terminal device 10 judges whether or not the user has fallen asleep after the user going to bed on the basis of outputs of the sleep measuring device 11B and the like and the motion sensor of the terminal device 10. In a case in which a user's input operation on the terminal device 10 is detected before the user falls asleep, the terminal device 10 initializes the game point described above. In other words, in a case in which a user operates the terminal device 10 before falling asleep, the terminal device 10 discards changes in the game point in accordance with elapse of time and resets the game point that is a reward for the user. When it is detected that the user has fallen asleep, the terminal device 10 gives a reward according to a user not performing an operation on the terminal device 10 in a period before the user falls asleep after the user is in an attitude for sleep to the user. In addition, in accordance with a length of this period (in other words, a time that has elapsed before the user actually falls asleep from a time when the user is going to take sleep), the terminal device 10 gives a reward that becomes more advantageous to the user in game play as the period is longer to the user. In addition, the terminal device 10 stops the process of changing the game point in accordance with elapse of time on the basis of the timing at which the user falls asleep and gives the game point changed in accordance with the elapse of time in a period until the user falls asleep to the user.

In addition, a condition for resetting the reward given to the user is not limited to the terminal device 10 and may include also a case in which any other device is operated by the user in addition to a case in which the user operates the terminal device 10 before the user falls asleep. For example, in a case in which, after going to bed, a user operates not the terminal device 10 but any other device such as a wearable device, the reward given to the user may be reset. In other words, in accordance with user's no operation on any device other than the terminal device 10 after going to bed, the user may be able to obtain a reward in a period before falling asleep.

In accordance with this, even when a user does not fall asleep at all after going to bed such as lying down on a bed, the user can obtain a reward that can be used in a game in accordance with no operation on the terminal device 10, and details of the reward becomes more advantageous as a period in which the user does not fall asleep at all becomes longer. Thus, even when it takes a long time before the user falls asleep after going to bed, the user is encouraged to focus on falling asleep without operating the terminal device 10.

In Step S1007, the terminal device 10 transmits information of a timing at which the attitude of the user for taking sleep has been detected, a timing at which the user has fallen asleep, a history of user's operations on the terminal device 10 (including a history of operations on the terminal device 10 also in case of after going to bed, going to fall asleep, and finally the user operating the terminal device 10), details of a reward obtained by the user, and a game point obtained by the user to the server 20.

In Step S1055, the server 20 receives information of various parameters of the user from the terminal device 10 and updates various kinds of data such as the user information database 281, the sleep result information 283, and the like.

As above, (1) the technology for handling a user's operation on the terminal device 10 before falling asleep has been described.

Figure 11:
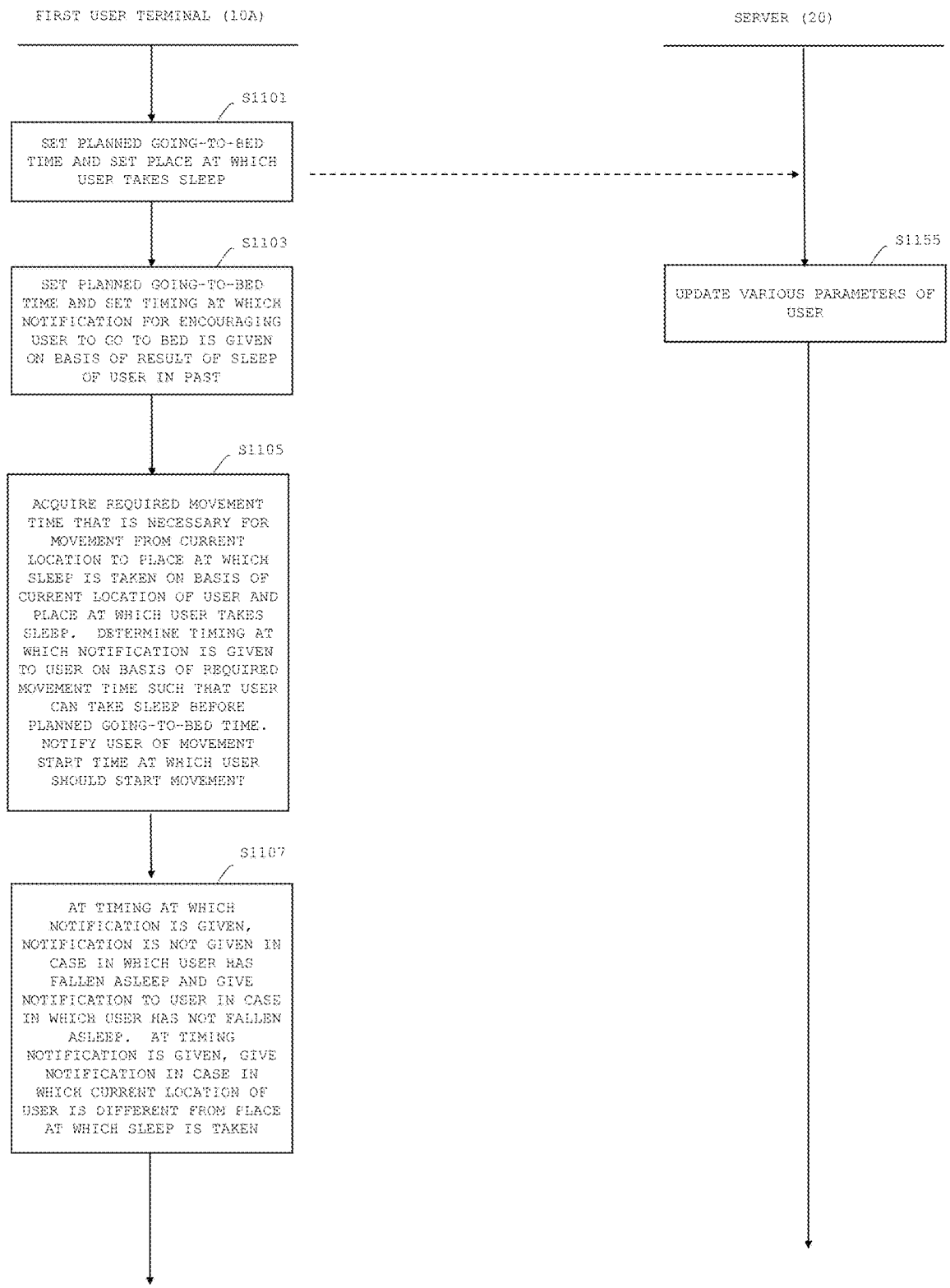
FIG. 11 is a flowchart illustrating a process of the terminal device 10 performing notification of information about sleep to a user at an appropriate timing.

FIG. 11 is a flowchart illustrating a process of the terminal device 10 performing notification of information about sleep to a user at an appropriate timing.

In Step S1101, the terminal device 10 sets a time at which the user plans to take sleep (a planned sleep time) in accordance with a user's operation. The terminal device 10 sets a place at which the user takes sleep in accordance with a user's operation or on the basis of a history of the current location of the user without being in accordance with a user's operation. The terminal device 10 transmits information of the planned sleep time and the place at which the user takes sleep to the server 20.

In Step S1155, the server 20 receives the information of the user's planned sleep time and the place at which the user takes sleep from the terminal device 10 and stores this information by updating the user information database 281 and the like.

In Step S1103, the terminal device 10 determines a timing at which a notification for encouraging the user to take sleep is given. The terminal device 10 determines a time frame in which a notification is given (a timing at which a notification is given), for example, such that the notification is given a predetermined time before the planned sleep time on the basis of the planned sleep time designated by the user in Step S1101. In addition, the terminal device 10 determines a time frame in which a notification is given on the basis of the past results of sleep of the user accumulated in the sleep result information 283 of the server 20.

For example, between a time at which the user went to bed and a time at which the user got up on the previous day is a time frame in which the user is going to take sleep or the user is actually sleeping. For this reason, the terminal device 10 may determine a time frame in which the user was actually sleeping as a timing at which the notification described above is not given on the basis of results of sleep of the user in the past (in other words, the notification may be given in a time frame except the time frame described above).

In Step S1105, the terminal device 10 acquires information of the current location of the user using the location information sensor 150 or the like. In addition, in a case in which information of places is input to each schedule in information of schedules of a user, the terminal device 10 may identify a current location of the user at a time of the schedule on the basis of the information of places associated with the schedule.

The terminal device 10 identifies a required movement time that is necessary for the user to move from the current location of the user to the place at which sleep is taken on the basis information of the current location of the user and the information of the place at which the user takes sleep. For example, the terminal device 10 may identify a required time for movement from the current location of the user to the place at which sleep is taken on the basis of route information of a public transportation organization or the like, information of congestion statuses of roads, and the like.

The terminal device 10 determines a timing at which a notification is given to the user on the basis of the required time for movement such that the user can perform an action for taking sleep (going to bed or the like) up to the planned sleep time set by the user. The terminal device 10 determines a timing at which a notification is given to the user by going back a time corresponding to the required time for movement from the planned sleep time and setting a predetermined margin. For example, in a case in which the planned sleep time is "23:00," and the required time for movement is "55 minutes," the terminal device 10 sets "35 minutes" as a margin and, for example, determines a timing at which a notification is given to the user as "21:30." In addition, the terminal device 10 notifies the user of a time at which the user needs to start movement to the place (his or her home or the like) at which the user takes sleep (for example, a notification of "Let's depart at 21:30 from the current location such that sleep can be taken at the planned sleep time of 23:00") such that the user can achieve the object of sleep (can take sleep at the planned sleep time).

The terminal device 10 may determine the margin described above on the basis of past results of sleep of the user. For example, in a case in which the user could not achieve the object of sleep even when a timing at which a notification is given to the user is determined with a first time set as a margin, the terminal device 10 may set a time longer than the first time as the margin.

In Step S1107, the terminal device 10 judges whether or not the user has fallen asleep at a timing at which a notification for sleep is given to the user, and, in a case in which the user has fallen asleep, the terminal device 10 does not give the notification such that the sleep of the user is not disturbed by the notification. In addition, in a case in which the user has not fallen asleep at the timing at which a notification for sleep is given to the user, the terminal device 10 gives the notification to the user.

In addition, in a case in which the current location of the user is different from the place at which the user takes sleep at the timing at which a notification is given to the user, the terminal device 10 gives the notification to the user. In other words, since the user is not present at the place at which sleep is taken, and thus a notification for encouraging the user to take sleep is given.

In addition, in a case in which the user is present at a place different from the place at which sleep is taken, the user is not present at the place at which sleep is taken, and thus a notification for encouraging the user to take sleep may be given at a predetermined timing regardless of past results of sleep of the user.

As above, (2) the technology for giving a notification for encouraging a user to take sleep at an appropriate timing and (3) the technology for encouraging the user to move such that the user appropriately takes sleep on the basis of the information of a current location of the user have been described.

Figure 12:
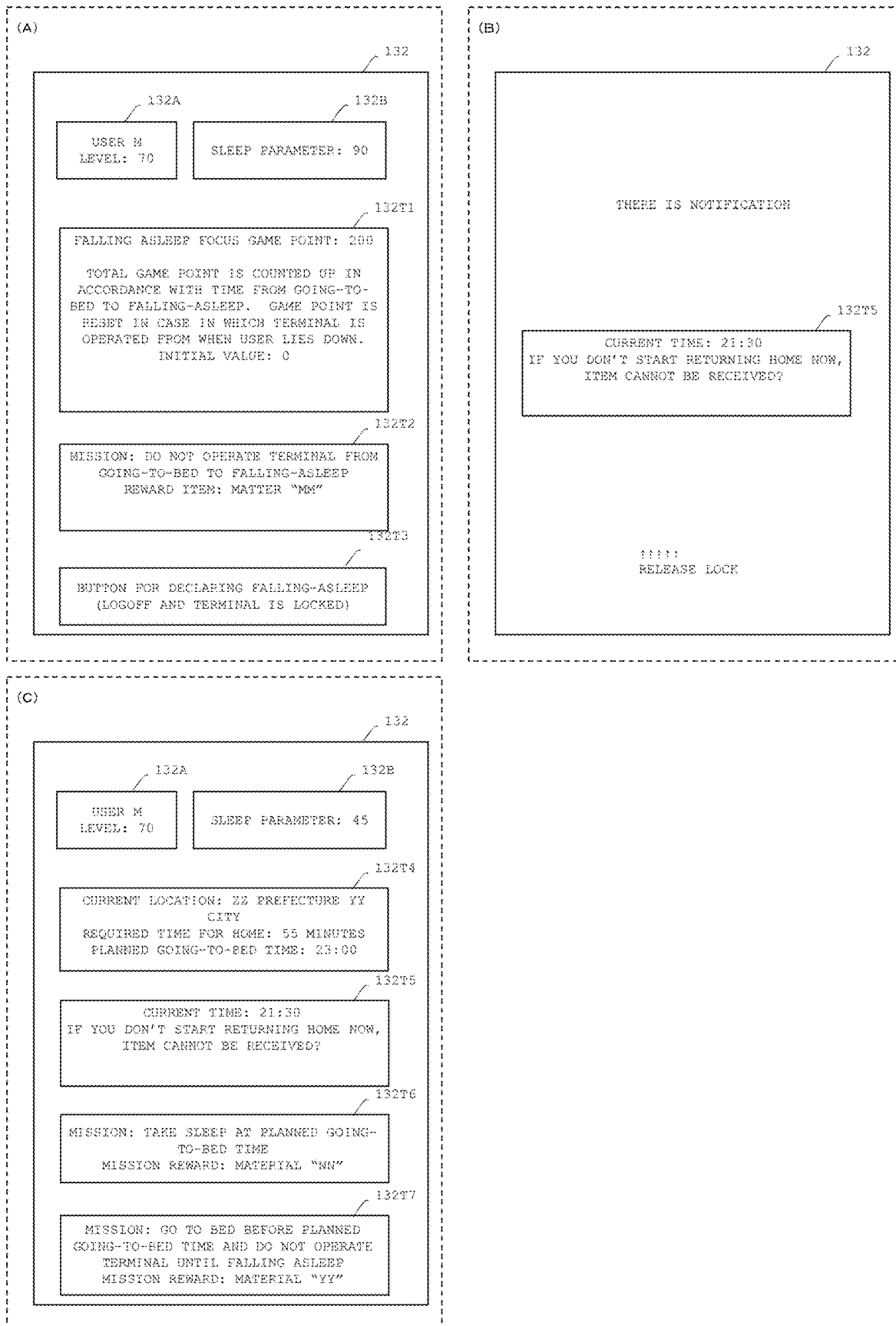
FIG. 12 is a diagram illustrating an example of a screen of a terminal device 10 according to Embodiment 2.

FIG. 12 is a diagram illustrating a screen example of the terminal device 10 according to Embodiment 2.

A screen example (A) illustrates an example of display according to (1) the technology for handling a user's operation on the terminal device 10 before falling asleep. As illustrated in the screen example (A), the terminal device 10 displays a notification 132T1, a notification 132T2, and a button 132T3 on the display 132.

The notification 132T1 is a region used for the terminal device 10 to notify a user that a reward of a game point can be acquired by not performing an operation on the terminal device 10 before the user falling asleep after goring to bed. In the notification 132T1, the terminal device 10 displays an accumulated value of the game point accumulated in accordance with the user obtaining the game point over a plurality of days as "falling asleep focus game point." In the notification 132T1, an initial value of the game point is displayed, and it is represented that the game point is raised in accordance with elapse of time before the user falls asleep, and the game point is reset by the user operating the terminal device 10 before the user falling asleep. The game point may be configured to be usable for various purposes in a game. For example, the game point may be configured as virtual currency that can be used in a game or may be configured to be able to be exchanged with virtual currency and used.

The notification 132T2 represents that a reward that can be used in a game is given in accordance with a user not operating the terminal device 10 before falling asleep after going to bed.

The button 132T3 is a button for accepting a user's input operation. By accepting an input operation on the button 132T3, the terminal device 10 may identify a timing at which the user goes to bed or a timing at which the user falls asleep. In response to an input operation on the button 132T3, the terminal device 10 causes the user to log off from the game and invalidates (locks) an operation on the terminal device 10. In a case in which an operation on the terminal device 10 is invalidated in this way, the terminal device 10 may determine a timing for canceling the invalidation on the basis of an object of sleep (a planned getting-up time or the like) of the user.

A screen example (B) and a screen example (C) illustrate display examples according to (2) the technology for giving a notification for encouraging the user to take sleep at an appropriate timing and (3) the technology for encouraging the user to move such that the user can appropriately take sleep on the basis of information of the current location of the user.

As illustrated in the screen example (B), the terminal device 10 displays a notification 132T5. The notification 132T5 includes details for encouraging the user to return home from a visiting place for achieving the object of sleep.

In addition, the notification 132T5 includes details for encouraging the user to obtain rewards for achievement of the object of sleep and not operating the terminal device 10 before falling asleep after going to bed. Furthermore, as illustrated in the notification 132T5, the terminal device 10 includes information representing a time at which the user starts to return home in details of the notification.

In the screen example (B), a current time and words (words "presently") suggesting a timing at which movement to a place at which sleep is taken starts to the user like "Presently, if you don't start to return home . . . " are included. In accordance with this, the user can recognize that returning home needs to start at a time represented as the current time.

The screen example (C) illustrates a screen example that is in a state in which the user cancels locking of the terminal device 10 in the screen example (B). As illustrated in the screen example (C), the terminal device 10 displays an object 132T4, a notification 132T5, reward details 132T6, and reward details 132T7.

The object 132T4 includes information of a current location of the user, information of a time required for the user to move to a place at which sleep is taken, and information of a planned sleep time.

The reward details 132T6 notify the user that a reward is received in a game by the user achieving the object of sleep. More specifically, as conditions for obtaining a reward, going to bed before a planned sleep time and falling asleep are presented to the user. As illustrated in the drawing, details of the reward are also presented to the user.

The reward details 132T7 notify the user that a reward in a game is given for not operating the terminal device 10 before the user falling asleep after going to bed. As illustrated in the drawing, details of the reward are also presented to the user.

Third Embodiment

As described above, in the second embodiment, the technology for handling a user's operation on the terminal device 10 before falling asleep, the technology for giving a notification for encouraging the user to take sleep at an appropriate timing, and the like have been described. In a third embodiment, the following will be described.

(1) A technology for encouraging a user to have a regular sleep habit by associating data relating to sleep of the user with ranking information is provided.

(i) For example, a game mode in which users having an appropriate sleep habit can participate and users having an inappropriate sleep habit cannot participate is prepared. In such a game mode, there is a multi-play mode in which a plurality of users participate. For example, matching is performed between user groups of which sleep habits are appropriate, and co-fighting and a battle game may be configured to be able to be performed.

(ii) Interchange between users having appropriate sleep habits and interchange between user groups having inappropriate sleep habits may be encouraged. Examples of the interchange includes transmission/reception of messages, multi-play/non multi-play, participation in ranking, and the like. In other words, a ranking battle among users having appropriate sleep habits is provided, and a ranking battle in which only users having inappropriate sleep habits can participate or a plurality of users can participate regardless of sleep habits may be provided.

(iii) By grouping users in accordance with time frames of sleep of the users, interchange between users of each group may be encouraged. For example, by grouping users into a morning type and a night type in accordance with time frames of sleep of the users, users of the morning type may be configured to be able to participate transmission/reception of messages, multi-play, rankings, and the like.

(iv) Users may be grouped in accordance with lengths of sleep times of the users. For example, by providing a group to which only users having sleep times equal to or longer than a predetermined time can be assigned, multi-play, ranking, and the like among users of the group may be configured to be able to be performed. As above, when a user desired interchange with another user, in a case in which the users are assigned to different user groups, one user needs to change a sleep habit.

(2) By forming a parameter having an effect on interchange among users using information about sleep of the users in a game, a technology for encouraging the user to have a regular sleep habit is provided.

For example, the game may be caused to progress such that it becomes more advantageous to a user as the quality of sleep of the user becomes better. As the quality of sleep of a user being good, there are a time until falling asleep being short, a length of the sleep time, a time for falling asleep, and a habit for sleep being settled for the user (daily results of sleep being stable to some degree in terms of the time frame of sleep, the quality of sleep, and the like), and the like.

For example, a game parameter of a user is determined by evaluating the quality of sleep of the user, and game play may be caused to progress using the determined game parameter. As the quality of sleep of a user becomes better, the condition of the user is assumed to be better. Thus, as the quality of sleep of a user becomes better, the value of the game parameter is set to be better for the game. In accordance with this, matching between users can be performed on the basis of the game parameter (matching among users of which the qualities of sleep are good and the conditions are good), and adjustment of parameters such as a capability value and the like of a game character (for example, a parameter representing the state of the game character being good and the like) based on the game parameter, and the like can be performed.

In addition, a degree of difficulty in the game may be adjusted in accordance with the value of the game parameter. For example, on the basis of the game parameter, as the quality of sleep of the user becomes better, the degree of difficulty in the game play may be raised. In addition, on the basis of the game parameter, matching among users whose qualities of sleep are in the same degree may be performed. For example, the game parameter may be the evaluation parameter (Step S655 and the like) described in Embodiment 1.

By configuring as described above, the enjoyment of a game is further improved in accordance with a user taking appropriate sleep, and thus it is possible for the user to make a habit of taking appropriate sleep.

In addition, for example, in a game program in which many users participate, there are cases in which the number of simultaneous connections increases only in a specific time frame (for example, the number of connecting users is extremely large only in a time frame of midnight). Also in such cases, by encouraging the user to have an appropriate habit of sleep, a time frame in which users participate can be distributed. Thus, in preparing resources (server costs and the like) that are necessary for a game operator to operate the game, a peak at which users simultaneously participate can be reduced, and the operating cost can be suppressed.

Figure 13:
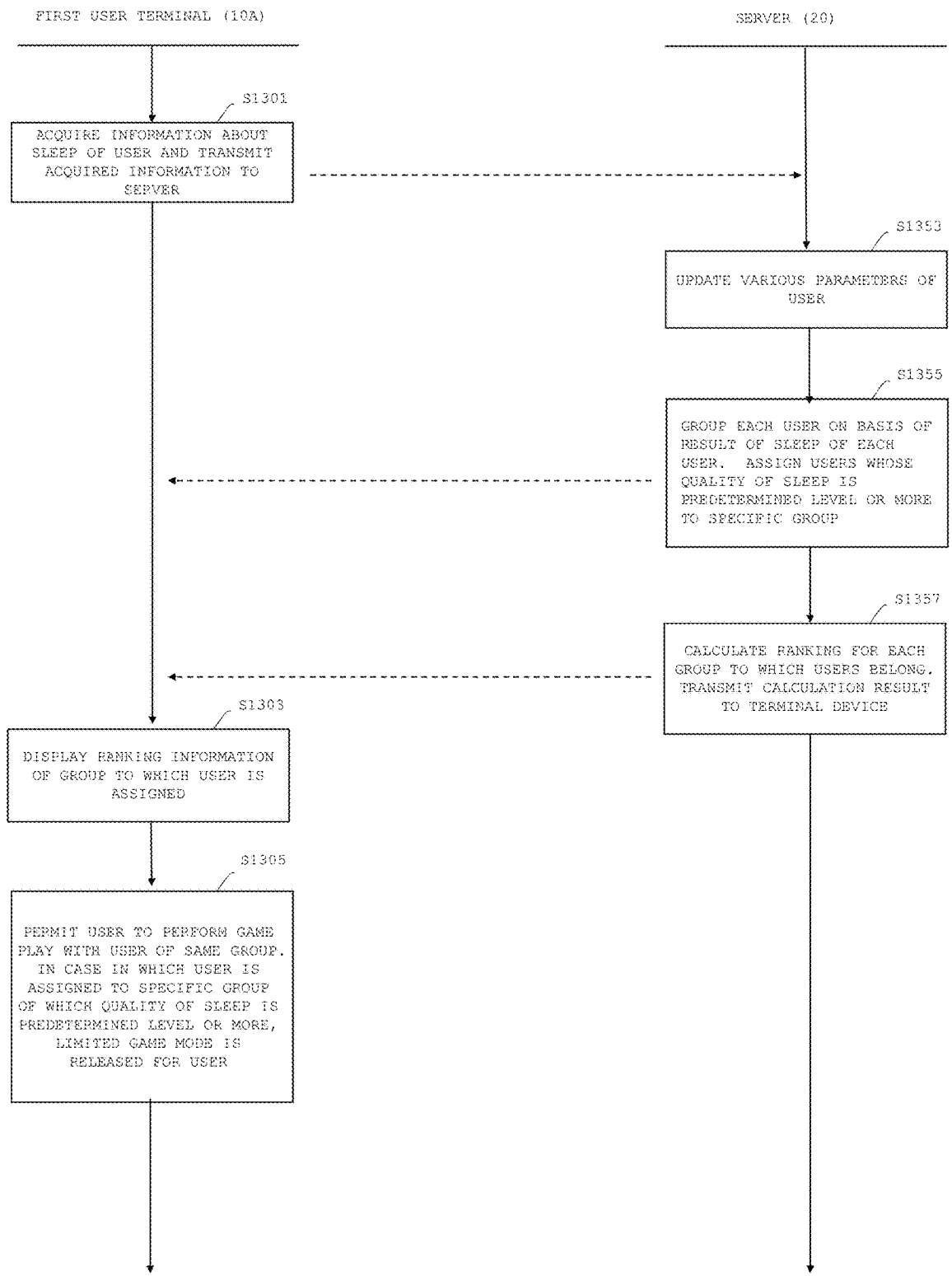
FIG. 13 is a flowchart illustrating a process in which information about sleep of users is used for ranking.

FIG. 13 is a flowchart illustrating a process in which information about sleep of users is used for ranking.

In Step S1301, the terminal device 10 acquires information about sleep of users and transmits the acquired information to the server 20.

In Step S1353, the server 20 receives information about sleep from a user and updates the sleep result information 283 and the like.

In Step S1355, the server 20 assigns each user to one of a plurality of groups on the basis of the result of sleep of each user. The server 20 evaluates whether the quality of the sleep of each user is equal to or higher than a predetermined level and assigns users whose qualities of sleep are equal to or higher than the predetermined level to a specific group.

For example, the quality of sleep being equal to or higher than a predetermined level may be a case in which a user takes sleep in accordance with an object of sleep (a planned bed time and a planned getting-up time) of the user, a case in which sleep time is equal to or longer than a predetermined time, a case in which a time until the user falls asleep is within a predetermined time (in other words, falling asleep is good), or the like.

In addition, the server 20 may divide users into groups in accordance with time frames of sleep of the users. For example, users of a morning lifestyle may be divided into a same group, and users of a night lifestyle may be divided into a same group.

In Step S1357, the server 20 calculates a ranking for each group to which users belong. For example, during an event period, a ranking point is given to a user in accordance with game play of the user. For example, a ranking point is given in accordance with the number of times of user's defeating of an enemy character by operating a game character, a history of a game character caused to perform specific actions such as skill activation and the like, the length of a time required for clearing the game, and the like. The server 20 stores results of calculated rankings for each group in a storage or the like as a database and transmits the results to the terminal device 10.

In Step S1303, the terminal device 10 receives information about rankings from the server 20. The terminal device 10 presents a calculated result of the ranking of the group to which the user belongs to the user by displaying the result on the display 132 or the like. In accordance with this, the user can obtain a reward (a game item or the like) that can be used in a game in accordance with the result of the ranking (a user's ranking). For example, in a case in which a user desires obtainment of a reward that can be obtained only for a specific ranking, a case in which even participation in the ranking cannot be performed only by playing the game for a long time occurs. Thus, in such a case, the user is encouraged to perform actions for enhancement of a lifestyle and obtainment of a longer sleep time.

In Step S1305, the terminal device 10 accepts game play based on a group assigned in accordance with a result of sleep of the user from the user. For example, the terminal device 10 matches the user with another user who is assigned to the same group, thereby providing a game using multi-play such as a battle or co-fighting.

In a case in which the server 20 assigns the user of the terminal device 10 to a group in which qualities of sleep of users are equal to or higher than a predetermined level in Step S1355, the terminal device 10 releases a game mode provided only for the users of the group to the user.

In addition, although the server 20 assigns users to the groups in Step S1355, the assignment of users to the groups may be performed for every day or every predetermined period. For example, in a case in which the server 20 performs grouping based on the information of users about sleep for every day, the user of the terminal device 10 may be configured to obtain a reward based on a ranking of the group that was assigned on the previous day.

Fourth Embodiment

As above, in description of the third embodiment, the technology for encouraging the user to have a regular sleep habit has been described. More specifically, as the technology for encouraging interchange between users in accordance with a sleep habit being appropriate, multi-play such as a battle or co-fighting among users whose sleep habits are appropriate, display of rankings of an event or the like of the game among users whose sleep habits are appropriate, and the like have been described.

In Embodiment 4, a technology of encouraging a user to sleep at a specific location will be described.

For example, the specific location is a facility (an accommodation facility) providing an accommodation function for users such as a hotel, an inn, or the like. In addition, the specific location may be a facility for performing a treatment on a body of the user and causing the user to take a rest such as a relaxation salon or the like.

Here, the terminal device 10 or the server 20 will be assumed to accept registration of a location at which a user usually takes sleep such as a home from the user and stores the location in the user information database 281 or the like in description. Hereinafter a process of granting a privilege to a user by taking sleep at a specific location that is a place other than the location registered by the user will be described.

In accordance with this, for example, the user can be encouraged to accommodate at the place without staying at a tourist spot or the like through movement.

Figure 14:
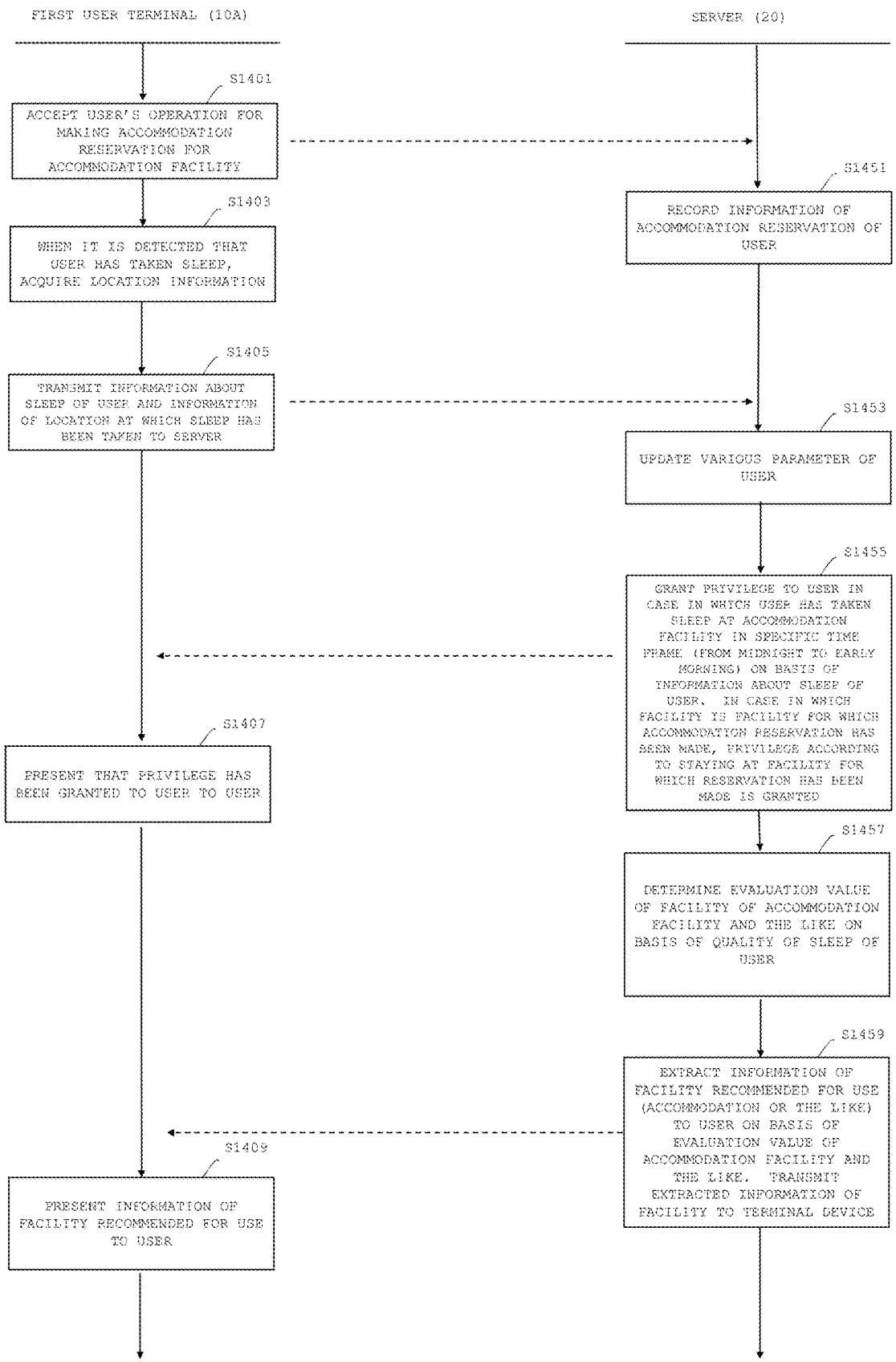

FIG. 14 is a flowchart illustrating a process of granting a privilege to a user in accordance with the user taking sleep at a specific location such as an accommodation facility or the like. In addition, it is assumed that registration of his or her home has been accepted from the user of the terminal device 10 in advance.

In Step S1401, the terminal device 10 accepts an operation for making a reservation of an accommodation facility from the user. The accommodation reservation of an accommodation facility includes the number of staying days, the number of persons to be accommodated, information for identifying the accommodation facility, a course of foods, an application of a coupon, and other information relating to an accommodation reservation. The terminal device 10 transmits information representing reservation details of accommodation to the server 20 on the basis of operation details of the user.

In Step S1451, the server 20 accepts a reservation of accommodation for the accommodation facility in response to an input operation of the user of the terminal device 10. The server 20 presents information of the user making a reservation for accommodation, staying dates, and other information relating to the accommodation reservation to a terminal device of the accommodation facility. The server 20 performs a process of settling an accommodation cost in response to an operation for an accommodation reservation of the user of the terminal device 10. The server 20 stores information relating to the accommodation reservation of the user in the storage unit 202 as a database.

In addition, the server 20 records information of a location of the user at a timing at which the user has taken sleep in the sleep result information 283. For example, in the terminal device 10, locations of the user at timings at which the user has gone to bed, the user has fallen asleep, the user has gotten up, and the like are acquired using the location information sensor 150. The terminal device 10 includes information of the location at which the user has taken sleep in the information relating to sleep of the user and transmits the information to the server 20.

Thereafter, it is assumed that the terminal device 10 detects that the user has gone to bed, the user has fallen asleep, and the like.

In Step S1403, when it is detected that the user has started sleep such as the user has gone to bed, the user has fallen asleep, or the like, the terminal device 10 acquires information of a location at which the user has taken sleep on the basis of an output of the location information sensor 150 or the like.

In Step S1405, the terminal device 10 transmits information about timings of sleep of the user and the information of the location at which sleep has been taken to the server 20.

In Step S1453, when the information about timings of sleep of the user and the information of the location at which sleep has taken are received from the terminal device 10, the server 20 updates the sleep result information 283 and the like.

In Step S1455, the server 20 judges whether the user has taken sleep at a specific location such as an accommodation facility in a specific time frame (for example in a midnight frame from 23:00 to 02:00 a.m. next day or the like) on the basis of the sleep result information 283 and the like. In a case in which the user has taken sleep at the specific location in the specific time frame, the server 20 grants a privilege in the game.

Here, the specific location may be a location of a facility for which the user makes a reservation of accommodation, temporary use, or the like. In addition, the specific location may be a location of a facility included in a list stored in the server 20 in advance regardless of whether information representing that the user has made a reservation is stored in the server 20. In addition, in a case in which the use of an accommodation facility or the like is reserved by the user, and the user has taken sleep in accordance with details of the reservation of the accommodation facility or the like, a privilege that is more advantageous to the user than in a case in which sleep has been taken without any reservation may be granted. For example, in short, a privilege for the use of an accommodation facility or the like through a reservation may be granted to the user. In accordance with this, the user can be encouraged to use a facility or the like after making a reservation thereof.

In addition, as a condition for granting a privilege to a user, a condition that the user takes sleep at a plurality of specific locations may be included. At this time, an order of the plurality of locations at which sleep is taken or dates on which sleep is taken and the like may be designated for the terminal device 10 or the server 20. For example, in accordance with the user taking sleep on a first date and the user taking sleep at another facility within a predetermined period (for example, the next day) from the first date, a privilege may be granted to the user. In addition, in accordance with the user, first, taking sleep at an accommodation facility (for example, facility "A") present in a first region and subsequently taking sleep at an accommodation facility (for example, facility "B") present in a second region, a privilege may be granted to the user. In accordance with this, for example, the user can be encouraged to continuously stay in a certain region and stay in a plurality of regions. In addition, the user can be encouraged to stay overnight at places in a predetermined order.

In addition, the specific time frame is not limited to the midnight frame but may be another time frame. For example, in accordance with a user taking sleep in a time frame other than overnight such as 13:00 to 15:00 as the time frame at a hotel, a relaxation salon, or the like, a privilege may be granted to the user. Furthermore, as a condition for granting a privilege, the specific time frame set to a certain time frame may be freely set or changed through an operator terminal and a supervisor terminal by an operator of the accommodation facility or the like and the supervisor or the like of the system.

In addition, the granting of a privilege to a user may be to give an effect causing the game progress of the user to be advantageous to the user, for example, a login bonus becoming advantageous, a predetermined parameter of the user being raised, or the like. Furthermore, the granting of a privilege to a user may be to give a predetermined game item (free virtual currency, an item for acquiring a game object through a lottery, a material item, or the like) to the user as a reward.

In addition, when the server 20 grants a privilege to a user, the quality of sleep of the user is evaluated on the basis of the information about sleep of the user, and details of the privilege may be changed in accordance with the quality of sleep of the user. For example, in a case in which the quality of sleep of the user is equal to or higher than a predetermined level (for example, a time until the user falling asleep being within a predetermined time, it can be judged that user is sleeping well on the basis of times of the REM sleep and the non-REM sleep, the user falling asleep in a predetermined time frame, or the like), a privilege that is more advantageous than in a case in which the quality of sleep is equal to or lower than the predetermined level may be granted to the user. In addition, in a case in which the quality of sleep is equal to or lower than the predetermined level, a privilege may not be granted to the user. In accordance with this, the user can be encouraged to take sufficient sleep at an accommodation facility or the like.

In Step S1457, the server 20 determines evaluation values acquired by evaluating accommodation facilities and the like at which the user has taken sleep on the basis of the qualities of sleep of the user. The server 20 records information of the accommodation facilities and the like and the evaluation values of the accommodation facilities and the like in the storage unit 202 in association with the information of the user. In accordance with this, for each of a plurality of facilities, an evaluation value is accumulated on the basis of the quality of sleep at the time of the user taking sleep using the facility.

In Step S1459, the server 20 extracts information of facilities recommended to the user of the terminal device 10 for use for taking sleep using accommodation or the like on the basis of the evaluation values of the accommodation facilities and the like. The server 20 transmits the extracted information of the facilities to the terminal device 10.

For example, in Step S1457, an evaluation value based on qualities of sleep of a plurality of users is accumulated for each facility, and thus facilities of which evaluation values are equal to or larger than a predetermined value may be presented to the user. In addition, facilities of which evaluation values of users and the like registered as friends in the friend list 282 are high as users relating to the user of the terminal device 10 may be presented to the user of the terminal device 10 as a recommendation. Furthermore, facilities of which evaluation values of other users and the like having results of sleep similar to results of sleep (the sleep result information 283) of the user of the terminal device 10 as users relating to the user of the terminal device 10 with a predetermined degree or more are high may be presented to the user of the terminal device 10 as a recommendation.

In Step S1409, the terminal device 10 presents information of the facilities presented as a recommendation from the server 20 to the user using the display 132 or the like. By using these facilities presented as the recommendation for accommodation and the like, the terminal device 10 presents details of a privilege granted to the user to the user. The terminal device 10 may display a user interface (an operation button and the like) for accepting an input operation for reserving the use of a facility for the user on the display 132 together with the details of the privilege. In accordance with this, the user can start an operation for reserving the facility while checking the details of the privilege.

In addition, in a case in which the progress status of the game of the user is a specific status, the terminal device 10 may present candidates of facilities that are targets to be used by the user to the user and present that a privilege is granted by taking sleep in a specific time frame at the facility.

Here, as a case in which the progress status of the game is the specific status, for example, there is a status in which game progress becomes advantageous in accordance with the user acquiring a privilege in a case in which the possibility of the user satisfying the clearing condition of a predetermined game unit (e.g., quest) is not high and the like. For example, in a case in which the level of a boss character is high with respect to the strength of an operation character of the user, and the possibility of being unsuccessful in defeating the boss character is a predetermined level or more, and in a case in which total power (e.g., a level and a capability value) of the strength of the operation character is lower than a value recommended in the game unit or the like, it is judged that the possibility of the user satisfying the clearing condition of a predetermined game unit is not high. In this case, details of the privilege may be provision of a game item for reinforcing the operation character of the user, obtainment of an effect causing game progress to be advantageous (for example, obtainment of an effect of raising the parameter of the operation character of the user in the game unit and the like) and the like.

As above, Embodiment 4 has been described. According to the configuration described above, in accordance with the user taking sleep at an accommodation facility or the like, a privilege in the game is granted to the user, and thus the user can be encouraged to use the accommodation facility or the like. In addition, in a case in which a privilege is granted to the user in a case in which the user has made a reservation of an accommodation facility or the like in advance, the cancel rate for the accommodation facility and the like can be further decreased.

Fifth Embodiment

In a fifth embodiment, an example in which an application program corresponds to a plurality of sleep measuring devices, and a predetermined effect is exhibited at the time of executing the application program in accordance with information used for identifying a sleep measuring device will be described. In the following example, an example in which a game program performs a game process on the basis of sensing data measured by each of a plurality of sleep measuring devices will be described.

<Configuration>

Figure 15:
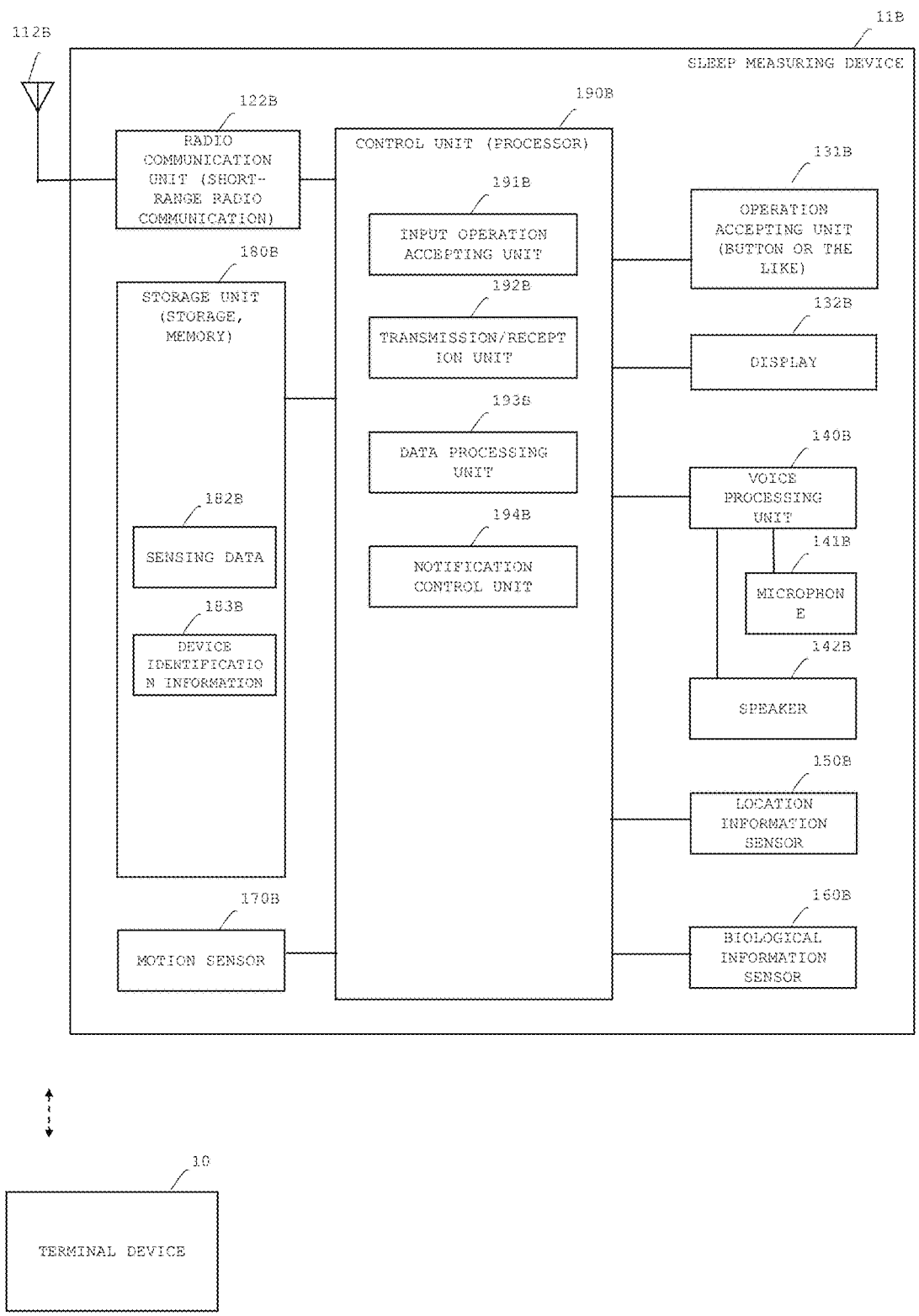

FIG. 15 is a block diagram illustrating a configuration of the sleep measuring device 11B and the like.

As illustrated in FIG. 15, the sleep measuring device 11B includes an antenna 112B, a radio communication unit 122B corresponding to each antenna, an operation accepting unit 131B, a display 132B, a voice processing unit 140B, a microphone 141B, a speaker 142B, a location information sensor 150B, a biological information sensor 160B, a motion sensor 170B, a storage unit 180B, and a control unit 190B. The sleep measuring device 11B also includes functions and components (for example, a battery for storing electric power, a power supply circuit controlling supply of electric power from the battery to each circuit, and the like) that are not particularly illustrated in FIG. 15. As illustrated in FIG. 15, the blocks included in the terminal device 10 are electrically connected through a bus or the like.

The antenna 112B radiates a signal output by the sleep measuring device 11B as an electric wave. In addition, the antenna 112B receives electric waves from a space and gives the received signal to the radio communication unit 122B.

For enabling the sleep measuring device 11B to communicate with other wireless devices, the radio communication unit 122B performs modulation/demodulation processes and the like for transmitting/receiving signals through the antenna 112B. The radio communication unit 122B is a communication module including a tuner, an RSSI calculating circuit, a CRC calculating circuit, a high-frequency circuit, and the like. The radio communication unit 122B performs modulation/demodulation and frequency transformation of wireless signals transmitted/received by the sleep measuring device 11B and gives received signals to the control unit 190B.

The operation accepting unit 131B has a mechanism for accepting a user's input operation. More specifically, the operation accepting unit 131B is a physical button or an input device such as a touch sensitive device.

The display 132B displays data of an image, a moving image, a text, and the like in accordance with control of the control unit 190B. The display 132B, for example, is realized using an LCD display.

The voice processing unit 140B performs modulation/demodulation of a voice signal. The voice processing unit 140B modulates a signal given from the microphone 141B and gives a signal after the modulation to the control unit 190B. In addition, the voice processing unit 140B gives a voice signal to the speaker 142B. The voice processing unit 140B, for example, is realized using a processor for voice processing. The microphone 141B accepts a voice input and gives a voice signal corresponding to the voice input to the voice processing unit 140B. The speaker 142B converts a voice signal given from the voice processing unit 140B into a voice and outputs the converted voice to the outside of the terminal device 10.

The location information sensor 150B is a sensor that detects a location of the sleep measuring device 11B and, for example, is a GPS module. In addition, in a case in which the sleep measuring device 11B is a device other than a user terminal such as a smartphone, it is assumed that the sleep measuring device 11B does not frequently move from a user's home. Thus, at the time of initial setting of the sleep measuring device 11B, the user may register information of a location at which the user takes sleep such as a user's home in advance.

The biological information sensor 160B is a sensor used for measuring biological information (a heart rate, a body temperature, and a sweat rate) of the user using the sleep measuring device 11B. For example, in a case in which the sleep measuring device 11B and the like are wearable devices, in accordance with a user wearing the sleep measuring device 11B, the biological information sensor 160B measures such biological information of the user.

The motion sensor 170B includes an acceleration sensor, an angular velocity sensor, and the like and detects movement of the sleep measuring device 11B. For example, in a case in which the sleep measuring device 11B is a wearable device of a wrist watch type or the like, in accordance with a user taking sleep with the sleep measuring device 11B worn, a motion of the user during sleep can be detected. In addition, by placing the sleep measuring device 11B in a mattress or the like of a bed on which the user takes sleep, in a case in which the user during sleep moves on the mattress, the motion can be detected. In accordance with this, it can be identified that the user during sleep is in a light sleep, a deep sleep, a REM sleep, or the like.

The storage unit 180B, for example, is configured using a flash memory or the like and stores data and a program used by the sleep measuring device 11B. In a certain phase, the storage unit 180B stores sensing data 182B and device identification information 183B.

The sensing data 182B is data that can be acquired by the sleep measuring device 11B performing sensing using the motion sensor 170B, the biological information sensor 160B, and the like. In addition, the sensing data is not limited to such data and, in a case in which various sensors such as an illuminance sensor, a voice sensor (microphone), an ultrasonic sensor, and the like used for measuring sleep of the user are included in the sleep measuring device 11B, data acquired from these various sensors may be included in the sensing data. In addition, various sensors such as the location information sensor 150B, the biological information sensor 160B, the motion sensor 170B, and the like may be selectively used by the sleep measuring device 11B and the like. In such a case, in accordance with a type and a measurement form of the sleep measuring device 11B and the like, a type of data acquired from the sleep measuring device 11B and the like as the sensing data 182B is changed as well. For this reason, in accordance with a type of the sleep measuring device 11B and the like, in other words, in accordance with a type and an accuracy of the sensing data 182B acquired from the sleep measuring device 11B, there are cases in which the sleep information 182 is different also in a case in which sleep of the same user is measured at the same timing.

The device identification information 183B is information used for identifying the sleep measuring device 11B. As described above, the information used for identifying the sleep measuring device 11B includes information of a provider providing the sleep measuring device 11B, information used for identifying a product of the sleep measuring device 11B (a product name, a product code, or the like), information used for uniquely identifying the sleep measuring device 11B (e.g., an identification code that is uniquely assigned to each device by a provider or information used when communication is performed (a MAC address or the like)), information of an application used until sensing data or the sleep information 182 is generated from the sleep measuring device 11B, and the like.

The control unit 190B reads a program stored in the storage unit 180B and executes commands included in the program, thereby controlling the operation of the sleep measuring device 11B. The control unit 190B, for example, is a processor, a microcomputer, or the like. By operating in accordance with a program, the control unit 190B exhibits functions as an input operation accepting unit 191B, a transmission/reception unit 192B, a data processing unit 193B, and a notification control unit 194B.

The input operation accepting unit 191B performs a process of accepting a user's input operation on an input device such as the operation accepting unit 131B. For example, in a case in which operation accepting unit 131B is configured using a physical button, the input operation accepting unit 191B detects a pressure or the like applied by the user for pressing the physical button and identifies that the physical button has been pressed, the physical button has been strongly pressed in, or the like.

The transmission/reception unit 192B performs a process for enabling the sleep measuring device 11B to transmit/receive data to/from external devices such as the terminal device 10, the server 20, the game controller 11A, the sleep measuring device 11C, and the like in accordance with a communication protocol.

The data processing unit 193B performs a process of performing an arithmetic operation on data of which input has been accepted by the sleep measuring device 11B in accordance with a program and outputting a result of the arithmetic operation to a memory or the like.

The notification control unit 194B performs a process of presenting information to a user. The notification control unit 194B performs a process of displaying a display image on the display 132B, a process of outputting a voice to the speaker 142B, a process of generating vibration, and the like. In addition, in a case in which the sleep measuring device 11B and the terminal device 10 communicate with each other, the notification control unit 194 gives a notification to a user by displaying an image in the sleep measuring device 11B, outputting a voice, providing vibration, or the like in linkage with the terminal device 10 giving a notification to the user.

<Data Structure>

FIG. 16 is a diagram illustrating a data structure of the sleep measuring device setting 284 stored by the server 20.

As illustrated in FIG. 16, each record of the sleep measuring device setting 284 includes item "sleep measuring device ID," item "device name," item "device provision period," item "sensing specification," item "effect at the time of game play," and the like.

The item "sleep measuring device ID" is information used for identifying a sleep measuring device. Sleep measuring devices are managed in a so-called white list form, and the item "effect at the time of game play" to be described below is set in accordance with devices that can be recognized on the server side. In addition, in a case in which a sleep measuring device 11B that cannot be identified by the server 20 is detected, the sleep information 182 may not be received from the sleep measuring device 11B that cannot be identified by the server 20, or a subsequent process may be performed using data used for the sleep measuring device 11B and the like that cannot be identified. In addition, "sleep measuring device ID" does not necessarily need to identify a device and includes types of software and an application used by the sleep measuring device 11B. For example, even in a case in which the same sleep measuring device 11B is used, the sleep measuring device 11B may be managed using different "sleep measuring device IDs" in a case in which a sleep measuring application A is used and a case in which a sleep measuring application B different from the sleep measuring application A is used.

The item "device name" represents a name of the sleep measuring device.

The item "device provision period" represents a period in which the sleep measuring device is provided by a provider. The period includes information of a timing at which the sleep measuring device became available on the market, a timing at which sales of the sleep measuring device ended, and a timing at which support from the provider of the sleep measuring device ended. In accordance with this, the terminal device 10 and the like can identify that the sleep measuring device has not been available on the market or has been available on the market.

The item "sensing specification" represents specifications of various sensor devices that are used for enabling the sleep measuring device to sense sleep of the user. The specifications of the sensor device include information of a target that can be measured by the sensor device (as illustrated in the drawing, the quality of sleep, a sleep time, biological information, and the like are included as the target), an accuracy of sensing, and the like. As illustrated in FIG. 16, targets that can be sensed by sleep measuring devices may be different from each other. For example, there may be a certain sleep measuring device that is able to measure a sleep time and is unable to measure the quality of sleep or the like.

The item "effect at the time of game play" represents details of an effect set for a user in a game based on a game program (parameters, a calculation equation, and the like used for generating the game effect) in a case in which a sleep measuring device represented in the item "sleep measuring device ID" is used by the user.

The details of the effect include details having effects on the game parameter. For example, as the details of the effect, (1) there are details having an effect on a degree of easiness in obtainment of game objects (game characters, game items, and the like) that can be obtained by a user in accompaniment with game play. For example, in a case in which a user measures sleep using a specific sleep measuring device, a setting of a probability of user' obtainment of a game object being configured to be a predetermined setting, and the like are included therein.

In addition, for example, in accordance with detection of a user getting up using the sleep information 182 or the like, in a case in which the user is caused to obtain a game content (including a game object) probabilistically, the probability may be determined in accordance with a sleep measuring device used for acquiring the sleep information 182.

In addition, such a probability may be changed by changing a table that defines a probability of obtainment of a game content. For example, a plurality of tables may be prepared in the server 20 or the like in advance, and information identifying a sleep measuring device and each of the tables may be associated with each other. In addition, the probability may be changed in accordance with calculation using variables and the like.

In accordance with this, in a case in which a user is using a specific sleep measuring device, the user can acquire an effect of the user being able to easily obtain game objects (game characters and the like) during game play and the like.

In addition to this, as details of the effect, (2) there are details having an influence on a game unit that can be played as a game by a user. For example, in accordance with a user using a specific sleep measuring device, a specific game unit (a quest, an extra stage, or the like) may be configured to be usable, or a probability of using the specific game unit may be changed. For example, in a case in which another quest is probabilistically generated when a quest for suppressing a boss character is cleared, the probability may be changed in accordance with information used for identifying the sleep measuring device or the like.

In addition to this, as details of the effect, (3) there are details having an influence on a game parameter given to a user. For example, a game parameter given to a user may be set in association with information for identifying a sleep measuring device in accordance with a length of a sleep time of the user, and the game parameter given to the user may be different for each sleep measuring device. As one example, in a case in which the length of the sleep time of the user is divided into a plurality of classifications (for example, (i) the sleep time is equal to or shorter than 5 hours, (ii) the sleep time is equal to or longer than 5 hours and equal to or shorter than 7 hours, and (iii) the sleep time is equal to or longer than 7 hours, or the like), and a game point or the like is given to the user in accordance with each classification, the quantity of the game point given to the user may be configured to be different for each classification in accordance with information used for identifying the sleep measuring device. Here, in order to provide a sleep measuring device that is appropriate for a person whose sleep time is relatively long, the quantity of the given game point may be configured to be larger as the sleep time becomes longer. In addition, in order to provide a sleep measuring device that is appropriate for a person whose sleep time is relatively short, the quantity of the given game point may be configured to be larger as the sleep time becomes shorter.

In addition, for example, in accordance with a user starting a game program, there may be an influence on the acquired privilege. For example, in a case in which a user is using a specific sleep measuring device, a login bonus at the time of starting a game may be configured to be changed. In addition, a login bonus that is given only in a case in which a specific sleep measuring device is continuously used may be provided. At this time, by providing different login bonuses in accordance with the number of types of devices, a motivation for continuous use of a plurality of devices can be provided for a user.

Such an effect may be set for the user over a predetermined period. For example, the login bonus may be changed or the like over a predetermined period or a predetermined number of times after a specific sleep measuring device is used.

In a case in which there is an effect on the login bonus as described above as an effect set for a user in a game when the user measures sleep using the sleep measuring device 11B, there are (i) a case in which the user logins the game on the next day of measurement of the sleep information 182 using the sleep measuring device 11B and (ii) a case in which, although the sleep information 182 was measured, the user logins the game after the next day. In addition, there is also (iii) a case in which, although the user logins the game, the user did not measure the sleep information 182 using the sleep measuring device 11B within predetermined days before the login.

In the case of (iii), although the user logins the game, there is no sleep information 182 acquired by the sleep measuring device 11B, and thus a login bonus according to login may remain to be given to the user. On the other hand, in each of the cases (i) and (ii) described above, separately from the login bonus given in accordance with user's login for the game, a privilege may be granted to the user in accordance with presence of the sleep information 182 acquired by the sleep measuring device 11B for a predetermined period before the timing of the login.

<Operation>

Figure 17:
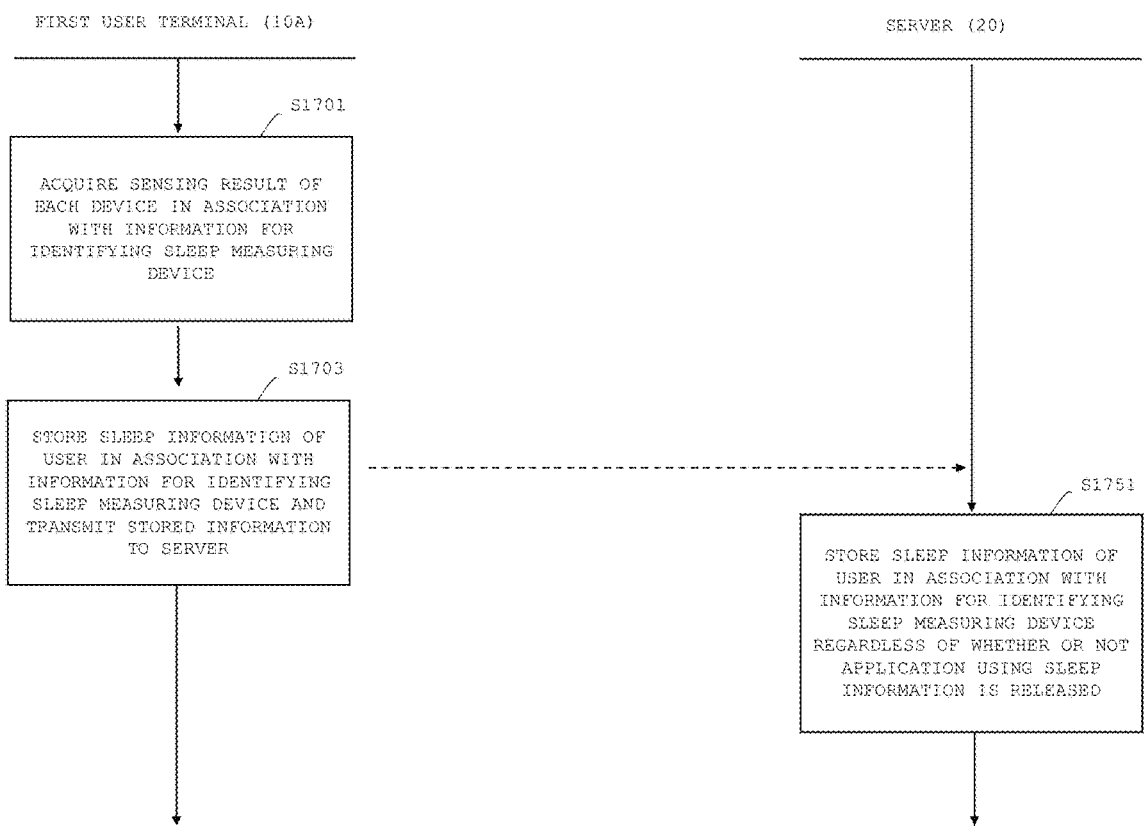
FIG. 17 is a flowchart illustrating a process of the terminal device 10 acquiring sensing results from one or a plurality of sleep measuring devices (a sleep measuring device 11B and the like) and accumulating the sensing results in the server 20 as a log.

FIG. 17 is a flowchart illustrating a process of the terminal device 10 acquiring sensing results from one or a plurality of sleep measuring devices (a sleep measuring device 11B and the like) and accumulating the sensing results in the server 20 as a log.

In Step S1701, the terminal device 10 acquires a sensing result (sensing data 182B) of each sleep measuring device in association with information for identifying the sleep measuring device 11B and the like (the device identification information 183B and the like).

In Step S1703, the terminal device 10 stores the sleep information 182 of the user in association with the information for identifying the sleep measuring device 11B and the like on the basis of the sensing results of the sleep measuring device 11B and the like and transmits the stored information to the server 20.

In Step S1751, the server 20 stores the sleep information 182 of each user of the terminal device 10 in association with the information for identifying the sleep measuring device 11B and the like as sleep result information 283. The server 20 stores the sleep information 182 of each user as a log regardless of whether or not an application (a game program or the like) using the sleep information 182 of the user has been released and has started the service.

Figure 18:
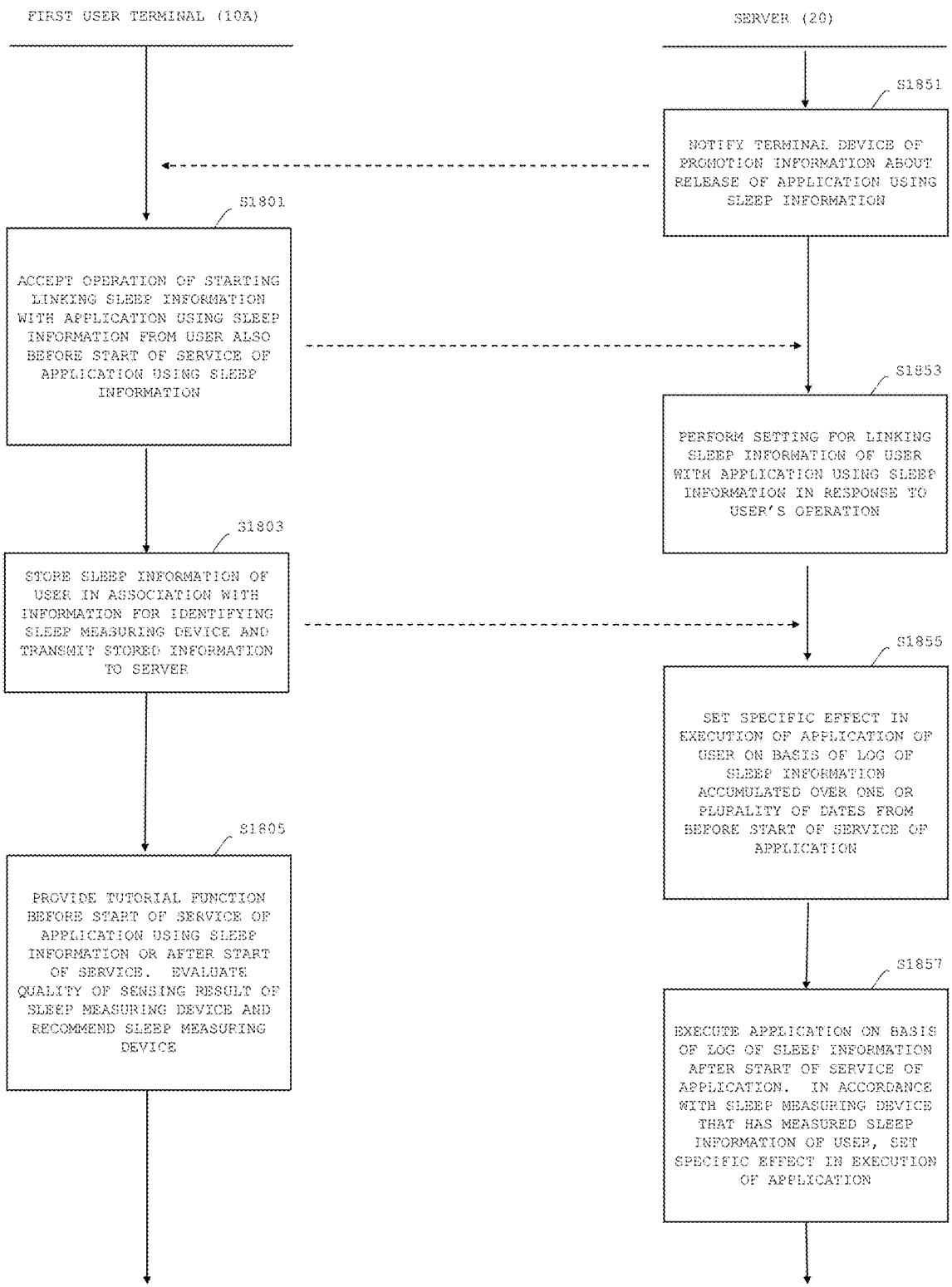
FIG. 18 is a flowchart illustrating a process of giving a notification to a user of the terminal device 10 at the time of an application using sleep information of the user starting a service.

FIG. 18 is a flowchart illustrating a process of giving a notification to a user of the terminal device 10 at the time of then application using sleep information 182 of the user starting a service. In the case of a game program as an example of the application will be described.

In Step S1851, the server 20 transmits information including a promotion relating to release of a game program using the sleep information 182 to the terminal device 10. For example, there are cases in which start of release of the game program is notified using an SNS or the like, and the user registers the game program in advance before the release. The server 20, for example, transmits information including a promotion to the user who has registered the game program in advance.

In Step S1801, even before start of the service of the game program using the sleep information 182 or before start of use, the terminal device 10 accepts an operation of starting to associate the sleep information 182 and the game program using the sleep information 182 with each other from the user. In other words, in this embodiment, although an example in which, in accordance with a user performing the associating operation, the game program side (a service providing company side based on the game program) can refer to the sleep information 182 of the user is described, the configuration is not limited thereto.

In Step S1853, in response to the user's operation in Step S1801, the server 20 performs a setting for associating the sleep information 182 of the user with the game program using the sleep information 182. In accordance with this, the game program can provide game progress and the like according to the sleep information 182 of the user for the user.

Thereafter, in Step S1803, the terminal device 10 stores the sleep information 182 of the user in association with the information for identifying the sleep measuring device 11B and the like and transmits the stored information to the server 20.

In Step S1855, on the basis of the log of the sleep information 182 accumulated over one or a plurality of days from before start of the service of the game program, the server 20 sets the execution of the game program of the user to exhibit a specific effect.

In Step S1805, the terminal device 10 provides a tutorial function for the user before start of the service of the game program using the sleep information 182 or after the start of the service. The tutorial function has a function of evaluating the quality of sensing results of the sleep measuring device 11B and the like and notifying the evaluated quality to the user. By acquiring the sleep result information 283 stored in the server 20 or the like, the terminal device 10 acquires a quality of measurement of each of the sleep measuring device 11B and the like. The terminal device 10 determines a sleep measuring device presented to the user as a recommendation and notifies the user of the determined sleep measuring device.

For example, in a case in which the quality of measurement of the sleep measuring device used by the user is below a predetermined level, the terminal device 10 recommends a sleep measuring device to the user. For example, as a factor for causing the quality of the sleep measuring device to be below a predetermined level, there is a case in which the user uses a sleep measuring device placed in a mattress or the like, and error is included in the sleep information 182 in accordance with inclusion of a motion of another user other than the user or a living organism such as a pet. In this case, the terminal device 10 recommends a sleep measuring device of a wearable device type to be worn by a user to the user.

When provision of a service based on the game program starts, the server 20 performs the process of Step S1857.

In Step S1857, after start of the service of the game program, the server 20 causes the game to progress on the basis of the log of the sleep information 182. In accordance with information for identifying the sleep measuring device that has measured the sleep information 182 of the user, a specific effect is set to the execution of the game program of the user.

<Screen Example>

Figure 19:
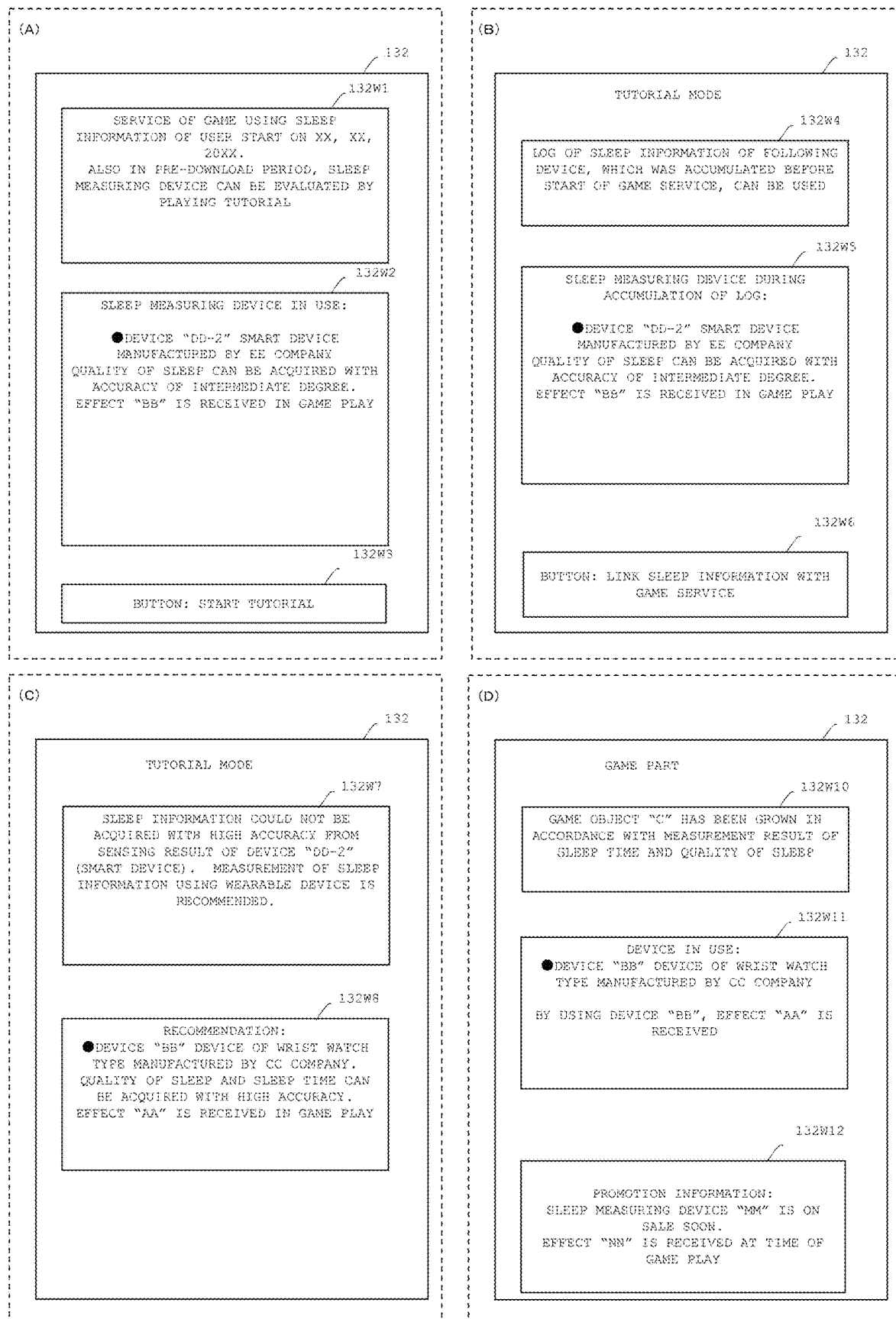
FIG. 19 is a diagram illustrating an example of a screen of the terminal device 10.

FIG. 19 is a diagram illustrating a screen example of the terminal device 10.

A screen example (A) illustrated in FIG. 19 is a case in which a game program corresponds to a plurality of sleep measuring devices and represents a phase in which a tutorial function is provided for a user before start of a service of the game program.

As illustrated in the screen example (A), the terminal device 10 notifies the user that provision of the game service using the sleep information 182 of the user starts in a notification section 132W1 (in other words, the screen example (A) is a phase before start of the game service), there is a period before the start of the game service in which a game program can be downloaded in advance, the function of evaluating the sleep measuring device is provided for a user also in the period, and the like.

The terminal device 10 displays information of the sleep measuring device used by the user in a notification section 132W2. The user sets the sleep measuring device to be able to communicate with the terminal device 10. As illustrated in the notification section 132W2, as information of the sleep measuring device, (1) a product name of the sleep measuring device, (2) a provider, (3) a type of the sleep measuring device (for example, a wearable device, a portable terminal, or the like), (4) accuracy of sensing of the sleep measuring device, (5) details of an effect exhibited in game play in a case in which the user causes a game to progress on the basis of the sensing result of this sleep measuring device using the sleep measuring device, and the like are notified to the user. By referring to the sleep measuring device setting 284 of the server 20, the terminal device 10 gives a notification represented in the notification section 132W2.

As illustrated in the operation button 132W3, the terminal device 10 provides a tutorial function also before start of the game service from the user and accepts an operation for starting the tutorial function from the user.

In the screen example (A), in accordance with the user performing an operation of starting the tutorial function (in accordance with the terminal device 10 accepting an input operation on the operation button 132W3), the screen example (A) transitions to the screen example (B).

The screen example (B) illustrates a phase in which the terminal device 10 provides the tutorial function for the user before start of the game service.

As illustrated in the screen example (B), the terminal device 10 notifies the user of the log of the sleep information 182, which has been accumulated in the server 20 from before start of the game service, being able to be used in a notification section 132W4. This corresponds to Step S1801 and the like illustrated in FIG. 18.

As illustrated in a notification section 132W5, the terminal device 10 notifies the user of information of the sleep measuring device of which a log of sensing results is accumulated by the user.

As illustrated in an operation button 132W6, the terminal device 10 accepts an input operation for associating the log of the sleep information 182 of the user and the game service with each other from the user. In accordance with this, the game service can provide a game service for the user by referring to the log of the sleep information 182 of the user.

A screen example (C) illustrates a phase in the tutorial function in which the sleep measuring device used by the user is evaluated, and, in a case in which there is a recommendation of another sleep measuring device, the recommendation is presented to the user. This corresponds to Step S1805 and the like illustrated in FIG. 18.

As illustrated in a notification section 132W7, the terminal device 10 notifies the user of the sleep information 182 not being able to be acquired with high accuracy from the sensing result of the sleep measuring device that has already been used by the user. In addition, the terminal device 10 notifies the user of information of the sleep measuring device determined as a target for recommendation to the user.

As illustrated in a notification section 132W8, the terminal device 10 notifies the user of the information of the sleep measuring device recommended to the user. This notification includes information of a name of the sleep measuring device to be recommended, a provider, a type, an accuracy of sensing, an effect in a game that can be acquired by the user in a case in which the user causes the game to progress on the basis of a sensing result of the sleep measuring device, and the like.

A screen example (D) illustrates a screen example of the terminal device 10 after a game service starts.

As illustrated in a notification section 132W10, the terminal device 10 notifies the user of a result of progress of the game based on a sensing result of the sleep measuring device 11B and the like of the user.

As illustrated in a notification section 132W11, the terminal device 10 notifies a user of information of the sleep measuring device 11B and the like of which sensing results are used by the user in game play. In this notification, an effect received by the user in accordance with the game progress is notified as well.

As illustrated in a notification section 132W13, the terminal device 10 notifies the user of promotion information of the sleep measuring device not only before start of a game service but also after the start of the game service. In this notification, information for identifying the sleep measuring device and details of an effect exhibited in a case in which game play is performed using the sensing result of the sleep measuring device are included.

As above, a user can set the sleep measuring device while using the tutorial function and the like. Such setting can be performed before the user starts game play using the sleep measuring device (for example, while the user has gotten up in a day time frame or the like). In accordance with this, a situation in which the sleep measuring device is not appropriate even when the user tries to perform game play after taking sleep and the like can be inhibited. In addition, the user can recognize an effect that is acquired for each sleep measuring device while the user has gotten up, and, for example, the user can easily determine a sleep measuring device to be used.

<Modification>

(1) Example in which Some of Sensing Results of a Plurality of Sleep Measuring Devices are Used by an Application:

Any one of a plurality of sleep measuring devices used by a user may be configured to be able to be used for a game service. As a user links an application and a plurality of sleep measuring devices with each other, the effects acquired by the individual sleep measuring devices may be configured to be able to be acquired in an overlapping manner by the user.

In addition, in a case in which sensing results of a plurality of sleep measuring devices of a user are used in a game service, by causing a game to progress using some of the plurality of sleep measuring devices in the game service while the server 20 accepts sensing results from the plurality of sleep measuring devices, a predetermined effect may be exhibited on the basis of information for identifying a sleep measuring device.

In accordance with this, the user can be encouraged to use a plurality of sleep measuring devices.

In addition, when the server 20 provides a game service, by causing a game to progress using sensing results of some sleep measuring devices of which qualities of sensing are good among sensing results of the plurality of sleep measuring devices, enjoyment intended by a game provider can be provided for a user.

In this way, in addition to an example in which the server 20 determines some sleep measuring devices used in a game service on the basis of qualities of sensing of a plurality of sleep measuring devices, some sleep measuring devices may be determined on the basis of specifications (a type, an accuracy, and the like) of the sleep measuring devices.

In addition, in a case in which a user uses a plurality of sleep measuring devices, measurement results of some sleep measuring devices are configured to be used with priority in a game process or the like, and measurement results of the other sleep measuring devices may be complementarily used. Some sleep measuring devices of which measurement results are used in a game process and the like may be set using in-advance designation or the like of a user, a game program, or the like. In addition, some sleep measuring devices may be set among a plurality of sleep measuring devices on the basis of an order in which measurement results are received by the terminal device 10 and the like. For example, in a case in which it is detected that the user has gotten up on the basis of measurement results of a plurality of sleep measuring devices, a sleep measuring device that has transmitted a measurement result enabling detection of user's getting-up to the terminal device 10 or the like earliest may be configured to be used in a game process and the like.

In addition, for example, in a case in which qualities of measurement of some sleep measuring devices used with priority deteriorate or in a case in which occurrence of battery exhaustion is detected by the terminal device 10 or the like, measurement results of the other sleep measuring devices may be configured to be used in a game process and the like.

(2) Example in which the Sleep Measuring Device 11B and the Like are Commonly Used by a Plurality of Users:

The sleep measuring device 11B and the like may be used by a plurality of unspecified users. For example, there may be a case in which the sleep measuring device 11B and the like are installed in an accommodation facility or the like, and a user using the accommodation facility measures sleep using the sleep measuring device 11B and the like.

In a case in which game is caused to progress on the basis of sensing results of the sleep measuring device 11B and the like, and a predetermined effect is exhibited on the basis of information for identifying the sleep measuring device 11B and the like, the terminal device 10 or the server 20 may perform such a game process on the basis of information of users commonly using the sleep measuring device 11B and the like. For example, by associating users commonly using the sleep measuring device 11B and the like with each other, the terminal device 10 or the server 20 may perform a predetermined game process using the users associated with each other. The terminal device 10 or the server 20, for example, may perform a game process such as registration of users associated with each other as mutual friends, provision of a playable game unit only for the users associated with each other, and execution of multi-play among the users associated with each other as the predetermined game process.

In a case in which the sleep measuring device 11B is commonly used by a plurality of users, in the sleep measuring device 11B, sensing results of the sleep measuring device 11B and information of the users may be stored in association with each other.

For example, before a user takes sleep using the sleep measuring device 11B, information for identifying the user may be input to the sleep measuring device 11B by the user. In accordance with the sleep measuring device 11B performing sensing in a state in which a user is identified or a user is designated, the sleep measuring device 11B stores a sensing result and information for identifying the user in association with each other.

In addition, the sleep measuring device 11B may identify a user to which a sensing result belongs in accordance with a sleep pattern of the user.

By receiving a measurement result of the sleep measuring device 11B from the sleep measuring device 11B, the terminal device 10 stores the measurement result and information for identifying a user who has taken sleep in association with each other.

In a case in which the measurement result acquired by the sleep measuring device 11B is used in a game process, the terminal device 10 may configure the measurement result not to be usable for users other than the user using the sleep measuring device 11B in the game process. For example, in a case in which a plurality of users such as family members living together use the sleep measuring device 11B, a measurement result of a first user may be configured not to be usable for a second user different from the first user in the game process. In addition, also in a case in which a plurality of users having a relationship such as family members commonly use the sleep measuring device 11B, a measurement result of the sleep measuring device 11B of a certain user may be configured not to be usable in a game process of another user.

In accordance with a plurality of users commonly using the sleep measuring device 11B regardless of whether or not the game program is executed by the terminal device 10, a measurement result acquired by the sleep measuring device 11B is accumulated in association with information for identifying each user. By executing a game program or the like, the terminal device 10 may receive measurement results acquired in a case in which different users use the sleep measuring device 11B over a plurality of dates from the sleep measuring device 11B. The terminal device 10 transmits a measurement result of each date acquired by the sleep measuring device 11B and information of a user who has taken sleep to the server 20 in association with each other. The server 20 stores the measurement result of sleep of each user in the sleep result information 283 on the basis of the information received from the terminal device 10.

According to such a configuration, in a case in which the sleep measuring device 11B is commonly used by a plurality of users, a measurement result of sleep of each user is recorded using the sleep measuring device 11B, and some users among the plurality of users may not execute the game program in the terminal device 10 Here, in accordance with the other users among the plurality of users executing a game program in the terminal device 10 and transmitting measurement results of sleep of the plurality of users to the server 20, the server 20 may perform a game process in accordance with the measurement results of sleep of the plurality of users. In other words, some users may obtain game parameters of a game based on the game program although the game program is not being executed. For example, in a case in which the sleep measuring device 11B is used among family member through borrowing/lending, in a situation in which the sleep information 182 of the previous day measured by a first user using the sleep measuring device 11B is not reflected in the game process, a second user acquires the sleep information 182 using the sleep measuring device 11B and executes a game program at the time of getting up on the next day, whereby the sleep information 182 of the first user is transmitted to the server 20 and is reflected in the game process.

Here, the sleep measuring device 11B is not limited to a device of a wearable type as described above. In a case in which sleep statuses of a plurality of users can be measured by the sleep measuring device 11B, a measurement result of sleep of each user can be accumulated in the sleep measuring device 11B in association with information for identifying each user. For example, by installing a device having an imaging function (for example, a portable terminal such as a smartphone) in a bed and analyzing a sensing result (captured image), actions of a plurality of users can be sensed. Also in such a case, by transmitting measurement results of sleep of a plurality of users to the server 20 from a certain user among the plurality of users, the measurement results of sleep of the plurality of users can be reflected in the game process.

(3) Example in which an Application is Executed by Acquiring Parameters of the Same Type in Information that can be Acquired by Each Sleep Measuring Device:

As described in the embodiments described above, sleep measuring devices may have different specifications. In addition, items that can be measured by each sleep measuring devices and accuracy of the measurement may be different. A game program and the like may use parameters of the same type among parameters acquired by the sleep measuring devices while responding to a plurality of the sleep measuring devices. For example, also in a case in which there are various parameters that can be measured by sleep measuring devices, a game process may be performed on the basis of information of "sleep time," "quality of sleep," and the like measured by the sleep measuring devices as parameters of the same type.

Here, in a case in which a user uses a plurality of sleep measuring devices, while a game program is executed using parameters of the same type acquired by the sleep measuring devices, a sleep measuring device of which sleep information 182 is used in the game process may be determined on the basis of a predetermined rule (for example, it may be determined using a lottery process) without depending on a user's operation. For example, when a user gets up, the terminal device 10 or the server 20 performs a game process on the basis of a measurement result acquired by any one of the sleep measuring devices, whereby the game can be caused to progress while unexpectedness is provided for the user.

(4) Example in which Process According to a Combination of Sleep Measuring Devices is Performed:

As described in each of the embodiments described above, various types of sleep measuring devices such as a wearable-type device, a table-shaped device, and the like are provided. In a case in which a user uses a plurality of sleep measuring devices, a game program and the like may perform the game process in accordance with a combination of the sleep measuring devices. For example, in a case in which a user measures sleep using both a sleep measuring device of a wrist watch-type and a sleep measuring device of a ring-type, in accordance with the combination, a process of giving a game parameter to the game character, giving a game item, and the like may be performed. In order to judge a combination of devices, as device identification information, group information of "wrist-watch type" and "ring type" is set in association with the devices as device identification information, and in the case of a combination of the same group information or a combination of different pieces of group information, a special effect according to each combination may be exhibited. In addition, as groups of devices, division into groups may be performed on the basis of whether a device is a wearable-type device worn by a user or a device used without being worn by a user.

Here, in a case in which a user uses a plurality of sleep measuring devices, as an example in which a process according to a combination thereof is performed, in a case in which there is an effect in a game that is acquired by using each sleep measuring device, effects of the sleep measuring devices may be accumulated, or a part of the effects of the sleep measuring devices may be reflected in the game play. For example, in a case in which there is a first effect in a game that can be acquired using a first sleep measuring device, and there is a second effect in the game that can be acquired using a second sleep measuring device, both the first effect and the second effect may be reflected in the game play of the user, or any one of the first effect and the second effect may be reflected. In addition, as a privilege according to use of a plurality of sleep measuring devices, at least one of the first effect and the second effect may be changed to be advantageous to the user.

In addition, by using a plurality of sleep measuring devices, there may be an effect in the game that is provided for the user. For example, in a case in which a user acquires the sleep information 182 using both the sleep measuring device of the wearable type and the sleep measuring device that is not worn by the user, a privilege may be granted to the user.

(5) Example in which Process is Performed in Accordance with Switching Between Sleep Measuring Devices Used by a User:

As described in each of the embodiments described above, the game program and the like perform the process such that a predetermined effect is exhibited in accordance with information for identifying the sleep measuring device.

Here, in a case in which the sleep measuring device used by the user is changed, for newly using the sleep measuring device, a privilege in the game program or the like may be granted to the user. Such a privilege may be granted to the user separately from the above-described predetermined effect exhibited in accordance with the information for identifying the sleep measuring device. In addition, such a privilege may be determined in accordance with information for identifying the sleep measuring device. Furthermore, such a privilege may be granted a predetermined number of times or over a predetermined period after the user has used the sleep measuring device. In accordance with this, for example, in a case in which a sleep measuring device is newly provided, the user can be encouraged to use the sleep measuring device.

In addition, in a case in which the sleep measuring device is used by a plurality of users, a total amount of the privilege described above may be set regardless of the number of users using the sleep measuring device. For example, in a case in which the privilege is provided over 10 days as predetermined dates, and a game item of a predetermined quantity is given for each day, when a user "A" and a user "B" alternately use the sleep measuring device, a privilege corresponding to 5 days is granted to the user "A," and a privilege corresponding to 5 days is granted to the user "B." In other words, a total amount of privilege corresponds to game items and the like corresponding to 10 days.

In addition, a total amount of the privilege described above that is taken for each user may be set. For example, in a case in which the privilege is provided over 10 days as predetermined dates, a privilege corresponding to a maximum of 10 days may be granted to each user.

As above, the privilege is granted to each user, and thus a user can be also encouraged to perform a test by borrowing the sleep measuring device from another user.

In addition, the sleep measuring device may be configured not to be used by a plurality of users. In other words, borrowing/lending of the sleep measuring device may be configured not to be able to be performed between users. For example, in a case in which the sleep measuring device is associated with information of a certain user, although another user uses the sleep measuring device, sleep information cannot be acquired, although the sleep information 182 is acquired, it cannot be reflected in the game, or although the sleep information 182 is acquired, an effect corresponding o the sleep measuring device may not be exhibited in the game.

An example in which the server 20 stores information for identifying the sleep measuring device and information of a timing at which the sleep information 182 has been acquired by the sleep measuring device in association with information of the user in the sleep result information 283 has been described. In a case in which the sleep information 182 is received by the terminal device 10 through communicating with the sleep measuring device, the terminal device 10 executing a game program may be configured to use sleep information 182 that is not associated with the information of any user in a game play of the user executing the game program. For example, a first user and a second user uses a sleep measuring device through borrowing/lending, sleep information 182 measure by a sleep measuring device at a certain timing may be not associated with any user. In such a case, any one user uses the sleep information 182 of the sleep measuring device by causing the terminal device 10 to execute a game program, whereby the sleep information 182 is stored in the server 20 and the terminal device 10 in association with the information of the user.

Here, the measured sleep information 182 and the information of the user may be stored in the sleep measuring device in association with each other. For example, by communicating with the terminal device 10 executing the game program, the sleep measuring device may associate the sleep information 182 and the information of the user with each other and store the information in association with the information of the user in the game. In other words, the sleep information 182 stored in the sleep measuring device is stored in the server 20, the terminal device 10, and the sleep measuring device in association with the information of the user through communicating with the terminal device 10.

The terminal device 10 communicates with the sleep measuring device, and in a case in which there is sleep information 182 not associated with information of any user, a specific process may be performed. For example, in a case in which the sleep information 182 measured by the sleep measuring device is not associated with any user, the terminal device 10 may accept designation of association of a certain user from the user of the terminal device 10. In addition, in a case in which there is sleep information 182 measured by another user in the sleep measuring device, the terminal device 10 may perform a process of transmitting a message to the another user, performing multi-play, or the like in accordance with the presence of the sleep information 182 of the another user.

(6) Example in which Process is Performed in Accordance with a Measurement Result of the Sleep Measuring Device for a Specific Game Content:

As above, in the description presented above, a plurality of sleep measuring devices can be used, and an effect according to the information for identifying the sleep measuring device is exhibited using a game program or the like.

In addition, a process corresponding to the information for identifying the sleep measuring device may be performed for the game content. For example, in a case in which a specific game character is raised in a game program, a parameter of the game character is stored in the server 20 or the like. At this time, in accordance with a user acquiring sleep information 182 using a specific sleep measuring device, an effect of providing a parameter for encouragement of raise or the like may be set to the game character.

(7) Privilege for Continuous Use of Same Sleep Measuring Device

In a case in which a user continuously uses the same sleep measuring device, a privilege may be granted in accordance therewith. For example, in a case in which days for which sleep information 182 has been acquired by the same sleep measuring device reach a predetermined period, a privilege may be granted to the user. For example, by referring to information that is unique to the sleep measuring device (identification information of the sleep measuring device as illustrated in FIGS. 4 and 16), the terminal device 10 can judge whether or not the user has continuously used the same sleep measuring device. In accordance with this, the user can be encouraged to use one sleep measuring device for a long time.

In addition, the terminal device 10 refers to information of a manufacturer and a seller of the sleep measuring device used by the user and may judge that the user has continuously use the same sleep measuring device in a case in which the manufacturers and the sellers are the same. In accordance with this, in a case in which the same manufacturer and the same seller newly sell the sleep measuring device, even when a user purchases and uses the sleep measuring device provided by the same manufacturer and the same seller, "a privilege according to continuous use of the same sleep measuring device" described above can be received, and a demand for buying a latest device for replacement can be called for attention.

(8) In addition, while a case in which a user uses a plurality of sleep measuring devices has been described, there are various foams of use. A sleep measuring device of the wearable device type and a sleep measuring device of an installation type may be used together. In addition, for example, a user may wear a plurality of sleep measuring devices of the wearable device type. In addition, a plurality of sleep measuring devices may be worn by the user at a specific part (for example, a user wears a plurality of sleep measuring devices of the wrist watch type or the like).

In addition, sleep information 182 of different types may be acquired from a plurality of sleep measuring devices. For example, there may be a case in which "the quality of sleep" may be measured using a first sleep measuring device, and "a sleep time" may be measured using s second sleep measuring device. The terminal device 10 and the like may present items that are desirably measured by each sleep measuring device to the user. In accordance with this, for example, a sleep measuring device that is appropriate for measuring "the quality of sleep" may be set to measure the corresponding item.

In addition, a user may designate a sleep measuring device among a plurality of sleep measuring devices that is to be used for measurement, and for example, designation may be accepted from the user before the user goes to bed. Furthermore, when a user gets up, designation of a sleep measuring device may be accepted from the user.

In addition, although an example in which a privilege is granted over a predetermined period in a case in which the sleep measuring device is started to be used has been described, a privilege may be granted in accordance with the number of times of use of the sleep measuring device during a predetermined period. For example, in a case in which a sleep measuring device is used over a predetermined number of times during one month, a privilege may be granted to the user.

In addition, in the embodiment described above, an example in which a sleep measuring device is recommended to the user has been described. In a case in which a user uses a plurality of sleep measuring devices, a sleep measuring device from which the sleep state of the user such as "the quality of sleep," "a sleep time," and the like is good is identified on the basis of measurement results of the sleep measuring devices, and a notification may be given to the user such that this sleep measuring device is used. In addition, grant of a privilege according to user's use of the sleep measuring device from which the sleep state of the user is good may be notified to the user.

Meanwhile, depending on the type of sleep measuring device or types of various sensors disposed in the sleep measuring device, there may be a deviation from a time at which the user originally takes sleep, and a situation in which the sleep information 182 cannot be correctly reflected in the game may occur. The reason for this may be due to a case of a malfunction of the device, a case of individual differences between the sleep measuring devices and various sensors, and a case of compatibility between an application processing data acquired from various sensors and various sensor. Particularly, an operator side that has experimentally used a certain sleep measuring device may perceive in advance that, in a case in which the sleep measuring device 11B is used, a sleep time shorter than a time in which the user actually takes sleep is output. In such a case, in a case in which the sleep measuring device 11B is used, when a sensing result or sleep information 182 acquired from the sensing result is used in a game, the parameter may be adjusted such that the sleep time is increased. In addition, in this case, when a deviation between a sleep time measured by the sleep measuring device 11B and information of a sleep time used in the game is output in a foam that can be recognized by the user, the user externally recognizes that the sleep time in the game is long. Then, there is concern that the user who has recognized the adjustment of the parameter as game strategy information may be confused, and thus it is preferable not to give a notification of the procedure of the parameter adjustment to the user.

In addition, an appropriate sleep measuring device may be recommended to a user on the basis of information about a sleep environment of the user such as information of family members and the like of the user and pets that may also be sleeping in the same bed. As information about the sleep environment of a user, for example, there are the number of users in an environment in which the sleep measuring device is used, information for identifying each user, a range in which a user takes sleep (a size of a bed and the like), a property of a bed (the hardness of the mattress and the like), and a target (a pet and the like) that can enter the range in which the user takes sleep. For example, a case in which the user sleeps on the same bed together with another person or the like may be considered. In a case in which users use sleep measuring devices, a user who lives together may be identified using a location at which each user takes sleep and the like.

Thus, for example, the server 20 or the terminal device 10 may judge a sleep measuring device from which the sleep information 182 is to be acquired or a sleep measuring device of which sleep information 182 is prioritized on the basis of the information about the sleep environment of the user. For example, in a case in which it is judged that a user is taking sleep on the same bed together with another person, even in a case in which the user uses also a sleep measuring device installed in the bed, it may be judged that sleep information 182 is acquired from the sleep measuring device of the wrist watch type. In addition, in a case in which it is judged that the user is taking sleep on the same bed together with another person, when the user uses only the sleep measuring device disposed in the bed, by recommending the user to use a sleep measuring device of the wrist-watch type, more accurate sleep information 182 can be measured.

In addition, although a plurality of users take sleep within a predetermined range, there are cases in which different beds are aligned, and each of the users is taking sleep on each bed. In such cases, the user may be recommended to use a sleep measuring device installed in the bed.

The configuration described above will be described with reference to the drawings.

Figure 20:
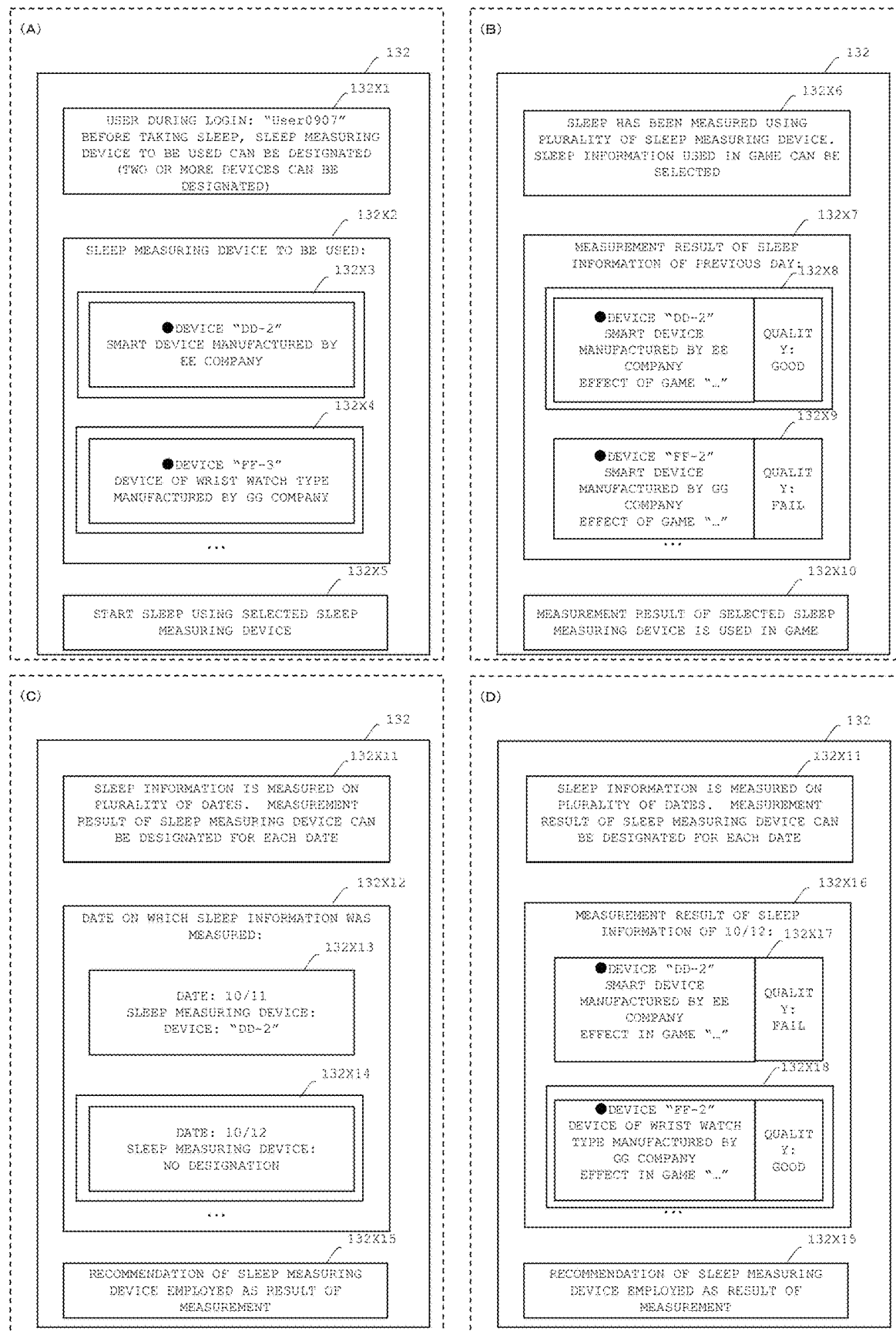
FIG. 20 is a diagram illustrating an example of a screen of a phase in which a sleep measuring device to be used in a game is determined in a case in which sleep information is measured by a user using a plurality of sleep measuring devices.

FIG. 20 is a diagram illustrating a screen example of a phase in which a sleep measuring device to be used in a game is determined in a case in which sleep information 182 is measured by a user using a plurality of sleep measuring devices.

A screen example (A) illustrated in FIG. 20 illustrates a phase in which the user designates a sleep measuring device to be used for measurement of the sleep information 182 before the user goes to bed. As illustrated in the screen example (A), the terminal device 10 displays a notification 132X1, a selection accepting section 132X2, and a sleep start accepting section 132X5 on the display 132.

The notification 132X1 is a region used for giving a notification of information of a user logging in the game and notifying that a sleep measuring device used for measuring the sleep information 182 can be designated by the user before the user takes sleep.

The selection accepting section 132X2 is a region for accepting designation of a sleep measuring device used for measuring the sleep information 182 from the user. As illustrated in the drawing, the terminal device 10 accepts designation of one or a plurality of sleep measuring devices in the selection accepting section 132X2. In the example illustrated in the drawing, an example in which a first sleep measuring device 132X3 and a second sleep measuring device 132X4 can be used by the user is illustrated. In addition, the sleep measuring device designated by the user may be emphasized in display. In the example illustrated in the drawing, both the first sleep measuring device 132X3 and the second sleep measuring device 132X4 are designated by the user.

The sleep start accepting section 132X5 is a region used for accepting an operation indicating that the user starts to take sleep from the user. When a user's input operation for the sleep start accepting section 132X5 is accepted, the terminal device 10 may invalidate at least a part of a user's input operation such that the terminal device 10 is not operated until the user gets up after taking sleep for enabling the user to focus on taking sleep. For example, for an operation other than operations at the time of emergency contact, a user's operation may not be accepted.

A screen example (B) illustrates a phase in which, in a case in which a user takes sleep, and sleep information 182 is measured using a plurality of sleep measuring devices, a sleep measuring device of which a measurement result is to be used in a game is designated by the user. As illustrated in the screen example (B), the terminal device 10 displays a notification 132X6, a measurement result designating section 132X7, and an operation accepting section 132X10.

The notification 132X6 is a region used for notifying that, in a case in which sleep information 182 is measured by a plurality of sleep measuring devices, sleep information 182 to be used in a game can be designated by the user.

The measurement result designating section 132X7 is a region for accepting a user's operation for designating a sleep measuring device of which a measurement result is to be used in a game in a case in which the user measures sleep information 182 using a plurality of sleep measuring devices. In the example illustrated in the drawing, information of a first sleep measuring device 132X8 and information of a second sleep measuring device 132X9 as a plurality of sleep measuring devices and information of qualities indicating whether or not results of sensing in these sleep measuring devices are good are displayed. In addition, in a case in which measurement results acquired by the sleep measuring devices are used in the game, the terminal device 10 displays also effects exhibited in the game in the measurement result designation accepting section 132X7. In the example illustrated in the drawing, the first sleep measuring device 132X8 is designated by the user and thus is emphasized in display.

The operation accepting section 132X10 is a region for accepting an input operation for using a measurement result of the sleep measuring device selected by the user in the game. In response to the input operation on the operation accepting section 132X10, the terminal device 10 may store the sleep information 182 measured by the sleep measuring device and information of the user in the terminal device 10, the server 20, and the sleep measuring device in association with each other.

As illustrated in the screen example (B), in a case in which the sleep information 182 is measured using a plurality of sleep measuring devices, although the user can designate sleep information 182 of which a remeasurement result is to be used in the game, other than that, the terminal device 10 may determine a sleep measuring device of which a measurement result is to be used in the game without using user's designation.

A screen example (C) illustrates a phase in which measurement results of sleep information 182 are accumulated over a plurality of dates, and a sleep measuring device of which a measurement result is to be used in the game is designated by the user.

As illustrated in the screen example (C), the terminal device 10 displays a notification 132X11, a date designating section 132X12, and a recommendation presenting section 132X15 on the display 132.

The notification 132X1 is a region for notifying the user that sleep information 182 to be used in the game can be designated for each date in a case in which measurement results of sleep information 182 are accumulated over a plurality of dates.

The date designating section 132X12 is a region for accepting designation of dates from the user. In the example illustrated in the drawing, a first date 132X13 and a second date 132X14 are displayed. As illustrated in the first date 132X13, the terminal device 10 displays information of a sleep measuring device designated to be used in the game on a date by the user on the display 132 together with information of the date. In addition, as illustrated in the second date 132X14, in a case in which a measurement result of a sleep measuring device has not been designated by the user for a date, the terminal device 10 displays no designation. In the example illustrated in the drawing, the second date 132X14 is designated by the user, and thus the second date 132X14 is emphasized in display.

The recommendation presenting section 132X15 is a region for accepting an input operation for displaying a recommendation of sleep information 182 (a sleep measuring device) to be used in the game on each date for the user.

A screen example (D) illustrates a phase in which designation of a sleep measuring device to be used in the game for a specific date is accepted from the user. For example, in response to designation of the second date 132X14 in the screen example (C), the terminal device 10 displays a screen illustrated in the screen example (D)

As illustrated in the screen example (D), the terminal device 10 displays a notification 132X11, a sleep measuring device designating section 132X16, and a recommendation presenting section 132X15 on the display 132.

The sleep measuring device designating section 132X16 accepts designation of a sleep measuring device to be used in the game for a specific date from the user. In the screen example (D), the terminal device 10 displays sleep information 182 of the first sleep measuring device 132X17 and the second sleep measuring device 132X18.

As above, in a case in which the user measures the sleep information 182 using a plurality of sleep measuring devices, and measurement results are recorded over a plurality of dates, a sleep measuring device of which a measurement result is applied can be selected by the user for every unit of one-time sleep (one day). The terminal device 10 or the server 20 stores a sleep measuring device of which a measurement result is associated for each date, and, for a user with whom a measurement result of a sleep measuring device is not associated, association of the sleep measuring device is accepted from the user.

In addition, in a case in which the sleep information 182 of the user is measured using the terminal device 10 as a smartphone and in a case in which the sleep information 182 is measured using any other sleep measuring device, a privilege granted to the user, and a predetermined effect set for the user may be configured to be different. For example, by using the sleep measuring device other than the smartphone, the privilege and the predetermined effect described above may be configured to be increased for the user. In accordance with this, by using the smartphone, a game using the sleep information 182 can be caused to progress, and in a case in which there is a sleep measuring device that is more appropriate for the acquisition of the sleep information 182 than the smartphone in the user or the like, the user can be encouraged to use the sleep measuring device.

In addition, in a case in which a smartphone is appropriate for the acquisition of the sleep information 182 (for example, breathing of the user can be measured using a microphone, the accuracy with which the sleep information 182 is measured using various sensors is relatively high, and the like), the user may be encouraged to measure the sleep information 182 using the smartphone.

(9) The game program is assumed to be a game raising a game object such as a game character in accordance with a sleep state of the user. Before the user goes to bed, a game object that is a target to be raised by the user may be configured to be able to be selected by the user. In addition, in a game based on the game program, another game object other than a raising target selected by the user is assumed to appear in accordance with a result of sleep (a sleep time or the like) of the user. In this case, when the result of sleep of the user reaches a predetermined value, a notification for advance announcement of appearance of another game object may be given to the user. Such a notification may be performed while the user is executing the game program, and in a case in which the game program is not executed by the user, a notification may be given by brightening the terminal device 10 and the like, outputting a voice, giving a push notification, or the like.

In addition, in a case in which the user operates the terminal device 10 after going to bed, there may be an adverse effect on the raise of the game object (for example, the game parameter is adjusted such that the raise ends in failure). In accordance with this, the user can be encouraged to improve the quality of sleep.

Summary

According to the embodiment described above, an application such as a game program performs a process on a premise that a plurality of sleep measuring devices can be used.

(1) In accordance with this, a provider of the game program or the like may encourage the user to use a specific sleep measuring device. For example, in order to improve enjoyment of a game or the like, the user may be encouraged to use a sleep measuring device that has been newly released.

(2) An environment that is appropriate for sleep is different for each person. Depending on a user, even when a specific sleep measuring device is used, it may be difficult to take sleep. According to the embodiment described above, the user can be encouraged to use a sleep measuring device that is appropriate for sleep of the user. In other words, by providing a different value to the user in accordance with the sleep measuring device, the user is unable to adapt to the use foam of the specific sleep measuring device, and even in the case of not being appropriate, the user may be encouraged to test another sleep measuring device. In accordance with this, withdrawal from the game is prevented using the sleep information 182, and an environment in which game play can be easily performed continuously can be provided.

Sixth Embodiment

In the first embodiment, an example in which, in accordance with a user achieving an object of sleep, various rewards in the game are given to the user has been described. In a sixth embodiment, a technology for causing a game to progress in accordance with taking sleep in at least one time frame (in the following description, referred to as a "core time") among a specific time frame that is a part of a time frame designated by the user as an object of sleep, a specific time frame set in relation to the time frame designated by the user as an object of sleep, and a specific time frame of sleep recommended by the game program will be described.

The game is caused to progress in accordance with taking sleep in the core time includes (i) for example, the game progress is caused to be more advantageous to a user than in a case in which sleep is not taken in the core time. The terminal device 10, for example, performs a process of setting predetermined parameters to a game character operated by a user or a non-player character (NPC) that is not an operation target of the user, disposing game objects having an influence on game progress such as a recovery item in a game unit (quest) that is a target for game play of the user, giving game items as rewards in a case in which a predetermined condition such as game clear or login is satisfied, and the like as game control. In a case in which a user takes sleep in the core time, the terminal device 10 performs control such that the setting of these parameters, disposition of game objects, and game items and the like given as rewards become more advantageous than in a case in which sleep is not taken in the core time. In addition, in accordance with a user taking sleep in the core time, the terminal device 10 may be configured to give a reward in the game to the user.

(ii) In addition, in a case in which a user taking sleep in the core time, although it cannot be determined that game progress becomes advantageous to the user, the terminal device 10 performs control that is not performed in a case in which the user does not take sleep in the core time. For example, in accordance with a user taking sleep in the core time, for a predetermined game character, a special motion, a special voice, a special story, and the like may be released.

In accordance with this, also in a case in which a user cannot take sleep in accordance with an object of the sleep although the user sets the object, by taking sleep in the core time, a predetermined effect can be exhibited in the game progress. In this way, while enhancement of a sleep habit is aimed with achievement of an object set by the user in advance set as an object at a normal time, even when it becomes difficult to achieve the object of sleep set in advance in accordance with a sudden schedule or the like, in a case in which sleep is taken during the core time, the influence on the game becomes small, and thus the user can be encouraged to continue the habit of sleep.

The core time is at least one of a time frame that is a part of a sleep time frame set by a user as an object or a time frame of sleep recommended by the game program. For example, the core time may be a predetermined time frame counting from a time acquired by delaying a sleep time of the object set by the user by a predetermined time, may be a predetermined time frame acquired by reversely counting from a time that is acquired by leading a getting-up time of the object by a predetermined time, may be a time frame of a predetermined ratio of the sleep time frame of the object, or may be an appropriate time frame based on health researches. In addition, the core time may have a time width of a predetermined time or more such that the user takes sleep at least a predetermined time. In other words, the core time may have a time length of a lowest limit.

In the sixth embodiment, as an example, even when the user cannot achieve the object of the sleep, an example in which, in accordance with taking sleep in the core time, various rewards are given to the user in the game will be described.

In accordance with this, by allowing variations in the sleep time according to variations in the user's lifestyle habit, while the user is encouraged to take sleep at least in the core time, a psychological burden for achievement of the object is reduced, and enjoyment of the game can be further improved.

<Configuration>

The configuration of the game system according to the sixth embodiment is similar to the configuration of the game system illustrated in FIGS. 1, 2, and 3, and thus repeated description will not be presented.

<Data Structure>

FIG. 21 is a diagram illustrating a data structure of sleep result information 6283 stored by the server 20. Data structures of a user information database 281 and a friend list 282 are similar to the data structures illustrated in FIG. 4, and thus repeated description will not be presented.

As illustrated in FIG. 21, the sleep result information 6283 further includes item "core time" in addition to the items of the sleep result information 283 illustrated in FIG. 4.

The item "core time" is at least one time frame among a specific time frame that is a part of a time frame designated by the user as an object of sleep, a specific time frame set in relation to the time frame designated by the user as an object of sleep, and a specific time frame of sleep recommended by the game program.

For example, a user sets going-to-bed at 23:00 and getting up at 06:00 as an object, a time frame from 01:00 to 05:00 that is a part thereof is set as a core time by the server 20. In accordance with the user taking sleep in the core time, the server 20 gives various rewards in the game to the user.

The item "evaluation parameter of sleep" is an evaluation parameter acquired by evaluating a result of sleep of the user in accordance with whether or not the user is taking sleep in the core time on the basis of the sleep result of the user. For example, in accordance with taking sleep in the core time, the quality of sleep being good, and the like, the value of the evaluation parameter may be caused to be good. The evaluation parameter may be visualization of the value of a so-called sleep debt in accordance with a result of sleep of the user.

The server 20 receives information about a result of sleep from the terminal device 10 of each user and calculates the evaluation parameter for each user. The server 20 provides game play using the evaluation parameter for the user. For example, in order to encourage the user to take sleep in the core time, in a case in which the evaluation parameter is not good (the sleep of the user is not appropriate, insufficient sleep is sensed, or the like), the server 20 or the terminal device 10 adjusts various parameters such that the efficiency of game play of the user is lowered, and a notification for encouraging the user to appropriately take sleep is given to the user.

<Operation>

Figure 22:
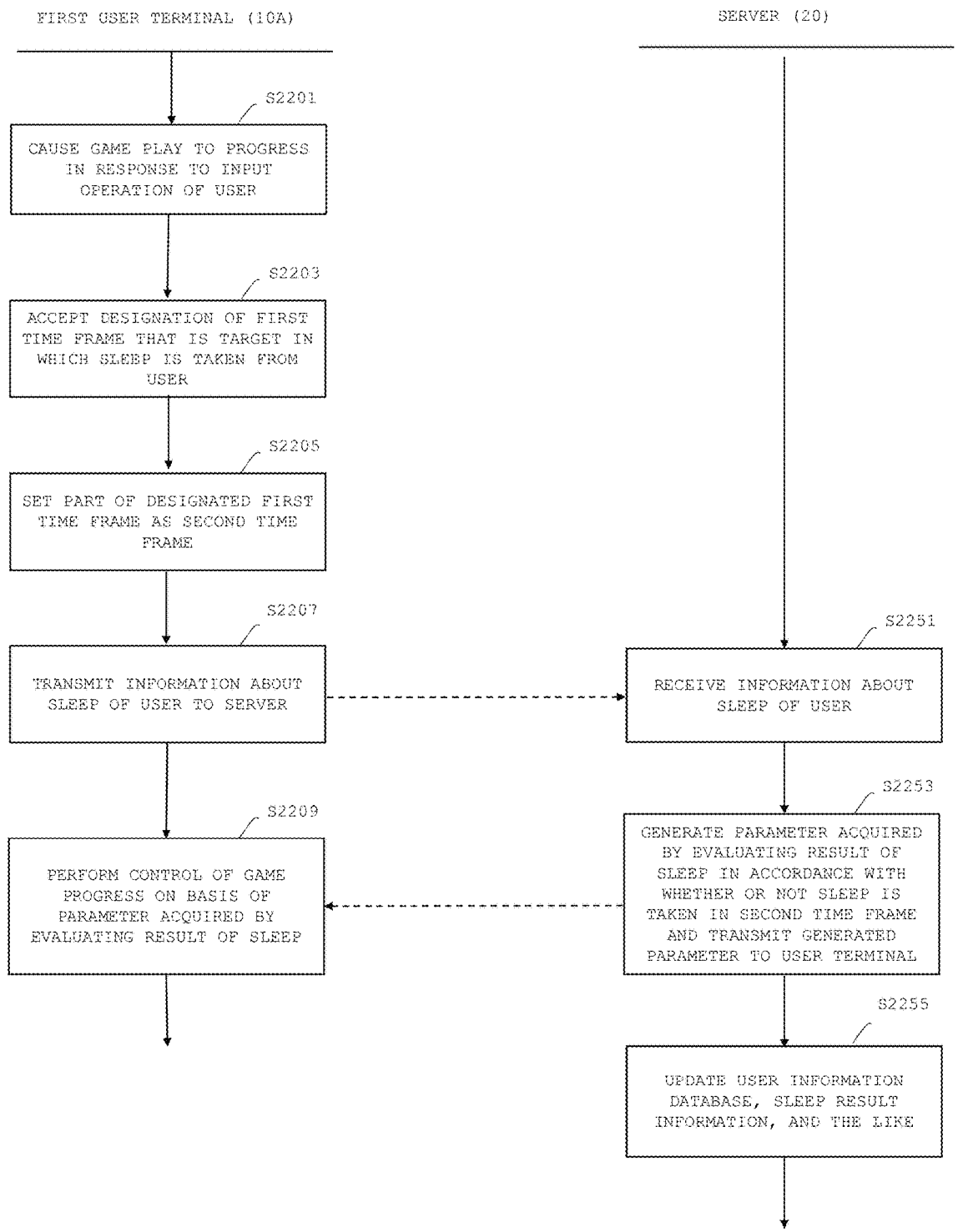
FIG. 22 is a flowchart illustrating a process of performing game control in accordance with whether or not a user is taking sleep in a core time.

FIG. 22 is a flowchart illustrating a process of performing game control in accordance with whether or not a user is taking sleep in a core time.

In Step S2201, the terminal device 10 causes game play of a quest designated by the user to progress in accordance with a user's input operation.

In Step S2203, the terminal device 10 accepts designation of a first time frame that is a target for taking sleep from the user. The first time frame may be an arbitrary time frame designated by the user or a time frame of a predetermined time or more. In addition, the terminal device 10 may perform the process of Step S2203 at an arbitrary timing regardless of the user performing the game play of the quest or may perform the process in accompaniment with the game play of the quest. For example, in accordance with the user performing game clear of a predetermined quest, designation of the first time frame may be accepted from the user using the process of Step S2203.

In Step S2205, the terminal device 10 sets the second time frame for a part of the designated first time frame as a core time.

The second time frame (the core time) may be a predetermined time frame counting from a time acquired by delaying a sleep time of the object set by the user by a predetermined time, may be a predetermined time frame acquired by reversely counting from a time that is acquired by leading a getting-up time of the object by a predetermined time, may be a time frame of a predetermined ratio of the sleep time frame of the object, or may be an appropriate time frame based on health researches. In addition, while counting from a time acquired by delaying a bed time of an object set by the user by a predetermined time, a time acquired by delaying the getting-up time of the object by a predetermined time may be a predetermined time frame to be set.

In one or more aspects of the disclosed subject matter, the second time frame (the core time) is a time frame of a predetermined time or more that is automatically set by the terminal device 10 for a part of the first time frame. In other words, while the terminal device 10 accepts designation of the first time frame from the user, the second time frame (the core time) may be set on the basis of the first time frame without being dependent on the user's operation for designating the second time frame.

In one or more aspects of the disclosed subject matter, the second time frame (the core time) may be a time frame determined in accordance with designation of the user for a part of the first time frame. In such a case, the terminal device 10 may set a restriction on the start time, the length, and the like of the second time frame (the core time). In addition, the user's designation of the second time frame includes user's designation of a ratio set as the second time frame in the first time frame in addition to the operation of user's designation of a start time or an end time of the second time frame.

In Step S2207, the terminal device 10 transmits information about sleep of the user to the server 20. The terminal device 10 transmits information of a time at which the user has gone to bed, a time at which the user has started to fall asleep, a time at which the user has awoken, a time at which the user has gotten up, and quality of sleep to the server 20 as information about sleep of the user.

In Step S2251, the server 20 receives the information about sleep of the user from the terminal device 10.

In Step S2253, the server 20 generates a parameter acquired by evaluating the result of sleep in accordance with whether or not the user taking sleep in the second time frame (the core time) regardless of whether the result of the sleep of the user is appropriate for the first time frame on the basis of the information about the sleep of the user and transmits the generated parameter to the user terminal.

In Step S2209, the terminal device 10 controls game progress on the basis of the parameter acquired by evaluating the result of the sleep.

In one or more aspects of the disclosed subject matter, in a case in which a predetermined condition is satisfied in the game play, a reward is given to the user. For example, in a case in which the user takes sleep in the second time frame (the core time), a predetermined game item is given. In a case in which sleep is not taken in the second time frame (the core time), the game item is not given.

In Step S2255, the server 20 updates the user information database 281, the sleep result information 283, and the like on the basis of the information of the result about sleep of the user that is received from the terminal device 10, progress information of the game, and the evaluation parameter generated in Step S2253.

As above, even when a user could not achieve an object of sleep set in advance in accordance with variations in the lifestyle habit, in a case in which sleep is taken in the core time, various rewards in the game are given to the user. For this reason, while the user is encouraged to take sleep at least in the core time, a psychological burden for achievement of the object is reduced, and enjoyment of the game can be further improved.

<Screen Example>

Figure 23:
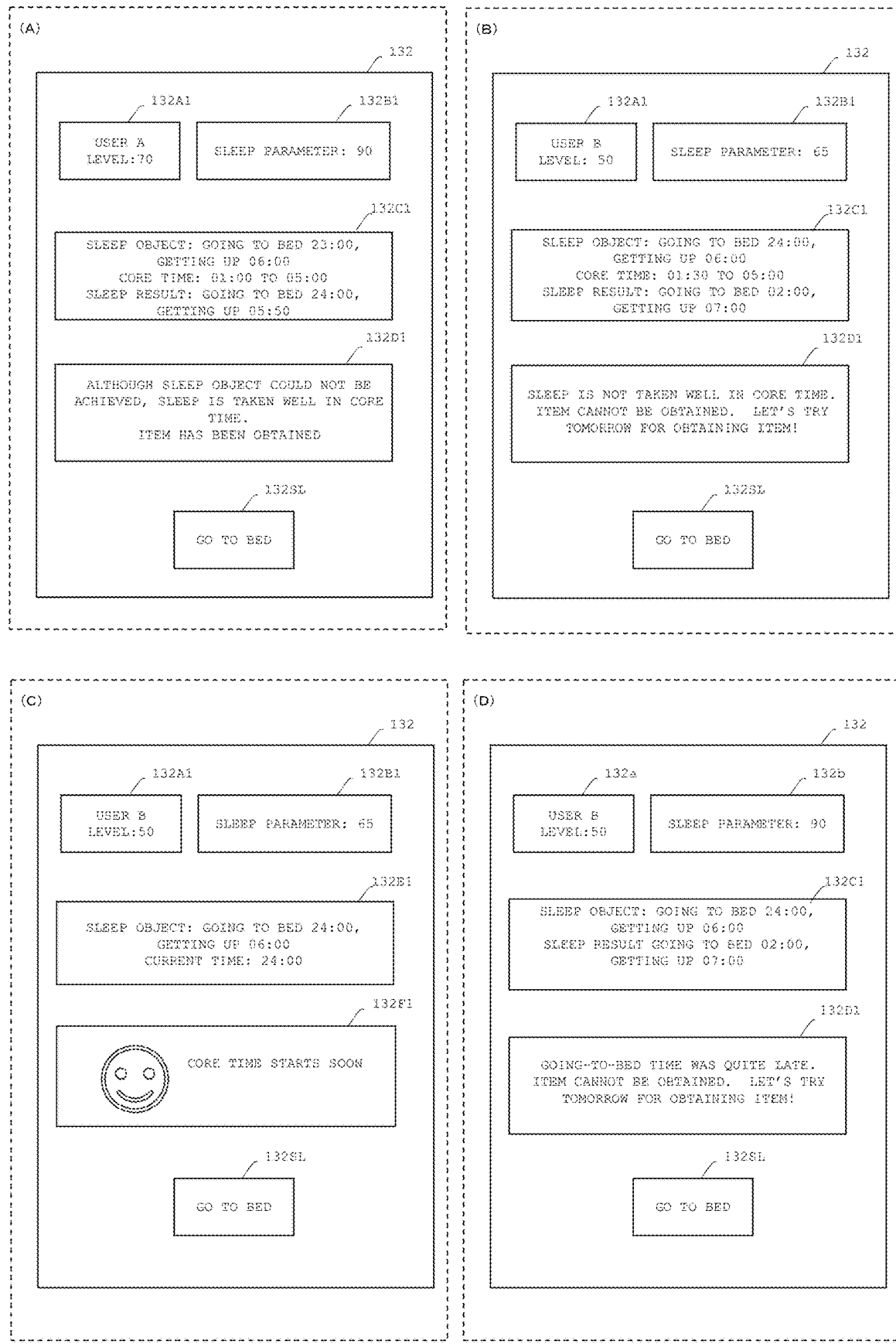
FIG. 23 is a diagram illustrating an example of a screen of a terminal device 10 according to Embodiment 6.

FIG. 23 is a diagram illustrating a screen example of the terminal device 10 and is a diagram illustrating a phase in which an evaluation parameter is generated by evaluating a result of sleep of the user in accordance with whether or not the user takes sleep in the core time, and game play using the evaluation parameter is performed.

As illustrated in screen examples (A) and (B) in FIG. 23, the terminal device 10 displays a user level 132A1, an evaluation parameter 132B1, a time presenting section 132C1, a notification display section 132D1, and a going-to-bed start button 132SL on the display 132.

The user level 132A1 represents a level of the user performing game play as a player. In accordance with the user performing game play, the terminal device 10 assigns an experience value (a player experience value) not to the game character but to the user. In accordance with the level as the player being leveled up, the terminal device 10 recovers the stamina value or raises a maximum value of the stamina value.

The evaluation parameter 132B1 is a region for displaying the evaluation parameter acquired by evaluating the result of sleep of the user in accordance with whether the user takes sleep in the core time on the basis of the information about the sleep of the user.

The time presenting section 132C1 is a region for displaying a sleep object of the user, a time frame of the core time, and information about a sleep result.

The notification display section 132D1 is a region for notifying the user of evaluation of the sleep of the user and details (giving of rewards and the like) controlling the game progress.

The going-to-bed start button 132SL accepts an operation of instructing start of going-to-bed from the user. For example, before going to bed, the user performs an input operation on the going-to-bed start button 132SL and then goes to bed. In response to the user's input operation on the going-to-bed start button 132SL, the terminal device 10 restricts a user's input operation on the terminal device 10 for a predetermined time in accordance with user's going-to bed. For example, an input operation for game play may not be accepted until a predetermined time such as a time set as an object of the getting-up time by the user, a time after elapse of the core time, or the like regardless of the user's input operation for the terminal device 10.

The screen example (A) illustrates a display example of a screen displayed in a case in which the user takes sleep in the core time. Since sleep is taken in the core time, an indication representing that a reward is given is notified to the user.

The screen example (B) illustrates a display example of a screen displayed in a case in which the user does not take sleep in the core time. Since sleep is not taken in the core time, an indication representing that a reward is not given is notified to the user.

As above, by displaying the going-to-bed start button 132SL, the terminal device 10 accepts an input operation when the user goes to bed. In the screen examples (A) and (B), when the user goes to bed, the time frame of the core time is displayed in the time presenting section 132C1. In accordance with this, the user can be encouraged to go to bed before the core time.

<Modification>

(1) In description of FIGS. 23(A) and 23(B), and the like, an example in which the time frame of the core time is presented to the user, and the user is encouraged to go to bed has been described. Other than this, the time frame of the core time may not be clearly represented. In addition, a character suggesting that it approaches the core time may be presented to the user without clearly representing the core time. For example, in a going-to-bed time in the first time frame designated by the user or a time that is a predetermine time before the going-to-bed time in the core time, the terminal device 10 may cause a character suggesting that the core time approaches to appear on the screen.

FIG. 23(C) is a diagram illustrating a screen example of the terminal device 10 according to this modification and is a diagram illustrating a screen example of the terminal device 10 before the user goes to bed. The terminal device 10 displays a user level 132A1, an evaluation parameter 132B1, an object presenting section 132E1, and a core time suggesting section 132F1 on the display 132. The object presenting section 132E1 is a region for displaying a sleep object set by the user and the current time. The core time suggesting section 132F1 is a region for presenting the character suggesting that it approaches the core time to the user. In the core time suggesting section 132F1, a message for encouraging the user to take sleep may be displayed to the user. For example, a message for encouraging start of sleep before start of the core time (for example, a message for encouraging only taking sleep "Now, it is time to go to bed!," a message suggesting that a reward is given to the user by taking sleep "Something may be given if you sleep now," a message suggesting a predetermined effect is exhibited in game progress by taking sleep "If sleeping now, maybe, a new character is encountered," or the like) may be displayed in the character.

In accordance with this, in accordance with the user not going to bed at a time set as an object, the user is prevented from getting up before the start time of the core time, and the user can be encouraged to go to bed before the core time. In accordance with this, although the object of sleep set by the user cannot be satisfied, in accordance with the user taking sleep in the core time, a predetermined effect is acquired in the game progress. For this reason, in accordance with the user being unable to achieve the object of sleep set in advance by the user, there is a motivation to not to give up formation of a habit of sleep, and the user can be encouraged to have an appropriate habit of sleep.

(2) In description of FIGS. 23(A) and 23(B), and the like, an example in which the user is encouraged to go to bed by presenting the time frame of the core time to the user has been described. Other than this, in a case in which the time frame of the core time is not presented to the user, and sleep has not been taken in the core time, a result acquired by causing the game progress to be more disadvantageous than in a case in which sleep is taken in the core time may be presented to the user.

FIG. 23(D) is a diagram illustrating a screen example of the terminal device 10 according to this modification and is a diagram illustrating a phase in which an evaluation parameter is generated by evaluating a result of sleep of the user in accordance with whether or not the user takes sleep in the core time, and game play using the evaluation parameter is performed. Different from FIGS. 23(A) and 23(B), the time frame of the core time is not displayed in the time presenting section 132c. In a case in which the user h does not take sleep in the core time, the bed time is delayed much than that of a schedule in the notification display section 132d, and thus an indication that a reward is not given is notified to the user.

In accordance with this, the user can be prevented from not going to be according to the object and getting up before the start time of the core time, and the user can be encouraged to have an appropriate habit of sleep.

(3) In Step S2203, designation of the first time frame that is an object for taking sleep is accepted from the user. In this example, on the display 132 of the terminal device 10, for example, an image representing time display of a time type, a bar type, or the like is displayed, and designation of the first time frame may be accepted from the user in the image.

Here, the terminal device 10 may set a time frame of the core time in advance without being dependent on a user's operation for designating the first time frame and present the set time frame to the user.

In addition, even when the user tries to decrease the width of the first time frame in the image, the terminal device 10 may perform image display such that a predetermined time or more is secured in the core time.

(4) In the example described in each of the embodiments described above, the core time has been described as being set on the basis of the first time frame (a time frame that is an object for taking sleep) in which designation is accepted from the user. Other than this, the terminal device 10 may reset the second time frame that is the core time in accordance with designation of the user or without being dependent on an instruction from the user.

For example, the lifestyle habit of the user may vary in accordance with a work performed by the user day by day, a user's method for enjoying a leisure time, and the like. For this reason, for example, the server 20 may acquire information indicating a past lifestyle habit of the user such as information of a time frame in which the user works (a work start time, a work end time, and the like), information of reservations made for user's spending a leisure time (reservation information of a leisure facility and the like), and the like and reset the second time frame (the core time) in the future that is set by the user.

(5) The server 20 may set a core time of one type for a user and not accept a setting of core times of two types or more. In addition, the set core time may be configured to be changeable, and cores times of two types or more may not be set at the same time.

(6) In the example described in each of the embodiments above, even when output results of the sleep measuring devices 11B and 11C in a time frame other than the second time frame set as the core time indicate that the user is sleeping, the game control may be performed by judging that the user does not sleep in a time frame other than the second time frame. In other words, the terminal device 10 may not reflect output results in a time frame other than the core time among the output results of the sleep measuring devices 11B and 11C in the game control and perform the game control in accordance with whether or not it is judged that the user is sleeping in the core time.

<Supplementary Note>

The matters described in each of the embodiments above will be presented below as a supplementary note.

(Supplementary note 1) A game program causing a processor in a computer (10, 20) including: the processor (19, 29) and a memory (15, 25) to execute: a first step (S2203) of accepting designation of a first time frame that is an object for taking sleep from a user; a second step (S2205) of setting a second time frame not coinciding with the first time frame in relation with the designated first time frame; a third step (S2207, S2251) of acquiring first information about sleep taken by the user; and a fourth step (S2209) of performing game control on the basis of the first information, in which, in the fourth step (S2209), the game control is performed in accordance with whether or not sleep is taken in the second time frame regardless of whether a result of sleep of the user is appropriate for the first time frame on the basis of the first information.

(Supplementary note 2) The game program described in ((Supplementary note 1), wherein, in the second step (S2205), the second time frame is set without being in accordance with an operation of the user designating the second time frame.

(Supplementary note 3) The game program described in (Supplementary note 1), wherein, in the second step (S2205), the second time frame is set in a part of the first time frame in accordance with an operation of the user designating the second time frame.

(Supplementary note 4) The game program described in (Supplementary note 2) or (Supplementary note 3), wherein, in the second step (S2205), the second time frame is re-set in accordance with designation of the user or on the basis of information of a lifestyle habit of the user.

(Supplementary note 5) The game program described in any one of (Supplementary note 1) to (Supplementary note 4), wherein, after execution of the second step and before execution of the third step, information (132C1) representing the second time frame or information (132F1) suggesting the second time frame to the user is presented to the user.

(Supplementary note 6) The game program described in (Supplementary note 5), wherein the presenting of the suggestion information (132F1) to the user includes displaying a character object on a screen and operating the character object such that the user is encouraged to take sleep in the second time frame.

(Supplementary note 7) The game program described in (Supplementary note 5), wherein the game program causes the processor to further execute: a fifth step of accepting (132SL) an input operation for instructing the user to start to take sleep, and the presenting of the information representing the second time frame or the suggestion information to the user includes causing a display unit (132) to display a screen used for accepting (132SL) the input operation in the fifth step and displaying the information (132C1) representing the second time frame or the suggestion information (132F1) on the screen.

(Supplementary note 8) The game program described in any one of (Supplementary note 1) to (Supplementary note 4), wherein the game control is performed without presenting the second time frame or the information suggesting the second time frame to the user also in any one of the first to fourth steps.

(Supplementary note 9) The game program described in (Supplementary note 8), wherein, in the fourth step, in a case in which a result of the sleep of the user is not appropriate for the second time frame, progress of a game is caused to be more disadvantageous to the user than in a case in which the result is appropriate for the second time frame.

(Supplementary note 10) The game program described in any one of (Supplementary note 1) to (Supplementary note 9) wherein, in the fourth step, a reward is given to the user in a case in which a predetermined condition is satisfied in the game play, and, in a case in which the user is taking sleep in the second time frame, the reward given to the user becomes more advantageous to the user than in a case in which the user does not take sleep in the second time frame.

What is claimed is:

1. A non-transitory computer-readable game program causing a processor in a computer comprising the processor and a memory to execute:
  accepting designation of a first time frame from a user;
  setting a second time frame not coinciding with the first time frame in relation with the designated first time frame;
  acquiring first information about sleep taken by the user;
  performing game control based on the first information, wherein the game control is performed in accordance with whether or not sleep is taken in the second time frame regardless of whether a result of sleep of the user is appropriate for the first time frame based on the first information; and
  after setting the second time frame and before acquiring the first information, presenting information representing the second time frame or information suggesting the second time frame to the user,
  wherein the presenting of the suggestion information to the user includes displaying a character object on a screen and operating the character object such that the user is encouraged to take sleep in the second time frame.

2. The non-transitory computer-readable game program according to claim 1, wherein the second time frame is set without being in accordance with an operation of the user designating the second time frame.

3. The non-transitory computer-readable game program according to claim 1, wherein the second time frame is set in a part of the first time frame in accordance with an operation of the user designating the second time frame.

4. The non-transitory computer-readable game program according to claim 2, wherein the second time frame is re-set in accordance with designation of the user or based on information of a lifestyle habit of the user.

5. The non-transitory computer-readable game program according to claim 1,
wherein the non-transitory computer-readable game program causes the processor to further execute:
accepting an input operation for instructing the user to start to take sleep, and
wherein the presenting of the information representing the second time frame or the suggestion information to the user includes causing a display to display a screen used for accepting the input operation and displaying the information representing the second time frame or the suggestion information on the screen.

6. The non-transitory computer-readable game program according to claim 1, wherein the game control is performed without presenting the second time frame or the information suggesting the second time frame to the user.

7. The non-transitory computer-readable game program according to claim 6, wherein in a case in which a result of the sleep of the user is not appropriate for the second time frame, progress of a game is caused to be more disadvantageous to the user than in a case in which the result is appropriate for the second time frame.

8. The non-transitory computer-readable game program according to claim 1,
wherein a reward is given to the user in a case in which a predetermined condition is satisfied in the game play, and
wherein, in a case in which the user is taking sleep in the second time frame, the reward given to the user becomes more advantageous to the user than in a case in which the user does not take sleep in the second time frame.

9. A method executed by a computer comprising a processor and a memory, by causing the processor to read and execute a game program stored in the memory, the method comprising:
accepting designation of a first time frame that is a target for taking sleep from a user;
setting a second time frame not coinciding with the first time frame in relation with the designated first time frame;
acquiring first information about sleep taken by the user;
performing game control based on the first information,
wherein the game control is performed in accordance with whether or not sleep is taken in the second time frame regardless of whether a result of sleep of the user is appropriate for the first time frame based on the first information; and
after setting the second time frame and before acquiring the first information, presenting information representing the second time frame or information suggesting the second time frame to the user,
wherein the presenting of the suggestion information to the user includes displaying a character object on a screen and operating the character object such that the user is encouraged to take sleep in the second time frame.

10. An information processing device, comprising:
processing circuitry; and
a memory,
wherein the processing circuitry, by operating on the basis of a game program stored in the memory, is configured to
accept designation of a first time frame that is a target for taking sleep from a user,
set a second time frame not coinciding with the first time frame in relation with the designated first time frame,
acquire first information about sleep taken by the user,
perform game control based on the first information,
wherein the game control is performed in accordance with whether or not sleep is taken in the second time frame regardless of whether a result of sleep of the user is appropriate for the first time frame based on the first information, and
after setting the second time frame and before acquiring the first information, present information representing the second time frame or information suggesting the second time frame to the user,
wherein the processing circuitry for presenting of the suggestion information to the user is further configured to display a character object on a screen and operating the character object such that the user is encouraged to take sleep in the second time frame.

11. The information processing device of claim 10, wherein the second time frame is set without being in accordance with an operation of the user designating the second time frame.

12. The information processing device of claim 10, wherein the second time frame is set in a part of the first time frame in accordance with an operation of the user designating the second time frame.

13. The information processing device of claim 11, wherein the second time frame is re-set in accordance with designation of the user or based on information of a lifestyle habit of the user.

14. The information processing device of claim 10, wherein the processing circuitry is further configured to
accept an input operation for instructing the user to start to take sleep, and
wherein the circuitry for presenting of the information representing the second time frame or the suggestion information to the user is further configured to cause a display to display a screen used for accepting the input operation and displaying the information representing the second time frame or the suggestion information on the screen.

15. The information processing device of claim 10, wherein the game control is performed without presenting the second time frame or the information suggesting the second time frame to the user.

16. The information processing device of claim 15, wherein in a case in which a result of the sleep of the user is not appropriate for the second time frame, progress of a game is caused to be more disadvantageous to the user than in a case in which the result is appropriate for the second time frame.

* * * * *